United States Patent
Li et al.

(10) Patent No.: US 11,254,700 B2
(45) Date of Patent: Feb. 22, 2022

(54) GSK-3β INHIBITORS AND USE THEREOF IN METHODS OF TREATMENT

(71) Applicant: UNIVERSITY OF HAWAII, Honolulu, HI (US)

(72) Inventors: Qing X. Li, Honolulu, HI (US); Zhibin Liang, Honolulu, HI (US)

(73) Assignee: UNIVERSITY OF HAWAII, Honolulu, HI (US)

( * ) Notice: Subject to any disclaimer, the term of this patent is extended or adjusted under 35 U.S.C. 154(b) by 0 days.

(21) Appl. No.: 16/760,700

(22) PCT Filed: Nov. 30, 2018

(86) PCT No.: PCT/US2018/063208
§ 371 (c)(1),
(2) Date: Apr. 30, 2020

(87) PCT Pub. No.: WO2019/108877
PCT Pub. Date: Jun. 6, 2019

(65) Prior Publication Data
US 2020/0331948 A1 Oct. 22, 2020

Related U.S. Application Data

(60) Provisional application No. 62/593,500, filed on Dec. 1, 2017.

(51) Int. Cl.
*C07H 7/06* (2006.01)
*C07C 49/835* (2006.01)

(52) U.S. Cl.
CPC ............ *C07H 7/06* (2013.01); *C07C 49/835* (2013.01)

(58) Field of Classification Search
None
See application file for complete search history.

(56) References Cited

U.S. PATENT DOCUMENTS

| | | |
|---|---|---|
| 2006/0276416 A1 | 12/2006 | Sinclair |
| 2011/0183942 A1* | 7/2011 | Worley ............... A61K 31/445 514/114 |
| 2016/0009692 A1* | 1/2016 | Borate ............... A61K 31/4196 514/254.05 |

OTHER PUBLICATIONS

Wolff, Manfred E. "Burger's Medicinal Chemistry, 5ed, Part I", John Wiley & Sons, 1995, pp. 975-977 (Year: 1995).*
Banker, G.S. et al., "Modern Pharmaceutics, 3ed.", Marcel Dekker, New York, 1996, p. 596 (Year: 1996).*
Luong et al., Helvetica Chimica Acta, 1980, vol. 63(1), pp. 244-249 (Year: 1980).*
Sim et al., ChemMedChem, 2011, 6(4), pp. 713-724. (Year: 2011).*
Zhang et al., Biomedical Pharmacology, 1997, vol. 54(9), pp. 1047-1053. (Year: 1997).*
Hsieh et al., Pharmaceutical Research, vol. 15(1), 1998, pp. 39-46. (Year: 1998).*
International Preliminary Report on Patentability in PCT/US2018/063208 dated Jun. 11, 2020.
International Search Report and Written Opinion in PCT/US2018/063208 dated Mar. 25, 2019.
Liang, Z., B. Zhang, W.W. Su, P.G. Williams & Q.X. Li (2016) "C-Glycosylflavones Alleviate Tau Phosphorylation and Amyloid Neurotoxicity through GSK3β Inhibition," ACS Chem. Neurosci. 7(7):912-923.
Song, Y, H.-D. Kim, M.-K. Lee, I.-H. Hong, C.-K. Won, H.-W. Bai, S.S. Lee, S. Lee, B.Y. Chung & J.-H. Cho. (2017) "Maysin and Its Flavonoid Derivative from Centipedegrass Attenuates Amyloid Plaques by Inducting Humoral Immune Response with Th2 Skewed Cytokine Response in the Tg (APPswe, PS1dE9) Alzheimer's Mouse Model," PLoS ONE 12(1): e0169509.

* cited by examiner

*Primary Examiner* — Traviss C McIntosh, III
(74) *Attorney, Agent, or Firm* — Licata & Tyrrell P.C.

(57) ABSTRACT

Isoorientin analogues and related compounds that inhibit glycogen synthase kinase-3β activity are provided as are methods of using these compounds in the treatment of cognitive, neurodegenerative or neurological diseases or conditions, as well as cancer, obesity, diabetes, inflammatory or autoimmune disease, cardiovascular disorder, metabolic syndrome X, hair loss, severe acute respiratory syndrome coronavirus, cocaine addiction, dental caries, bone loss and glaucoma.

8 Claims, 6 Drawing Sheets

GSK-3β INHIBITORS AND USE THEREOF IN METHODS OF TREATMENT

INTRODUCTION

This application is a U.S. National Stage Application of PCT/US2018/063208 filed Nov. 30, 2018 and claims benefit of priority to U.S. Provisional Patent Application Ser. No. 62/593,500, filed Dec. 1, 2017, the contents of each of which are incorporated therein by reference in their entirety.

This invention was made with government support under grant no. NA/HAW05032-R awarded by the United States Department of Agriculture National Institute of Food and Agriculture. The government has certain rights in the invention.

BACKGROUND

Glycogen synthase kinase-3β (GSK-3β) is a key protein kinase in the cascade leading to aberrant tau hyperphosphorylation. Elevated GSK-3β activity has been implicated in Alzheimer's disease and other tauopathies. Overactive GSK-3β hyperphosphorylates over 70% of the potential phosphorylation sites on tau proteins in Alzheimer's disease brains, which impairs the healthy interactions of tau proteins with microtubules. The development of selective GSK-3β inhibitors modulating aberrant tau phosphorylation is therefore a promising strategy for Alzheimer's disease chemotherapy.

Traditional GSK-3β inhibitors target the highly conserved ATP site. However, the limited selectivity of those inhibitors raises safety concerns owing to off-target effects and, therefore, remains a major challenge in GSK-3β-based drug development. Despite substantial efforts in developing GSK-3β inhibitors for Alzheimer's disease in the past decades, only lithium carbonate and tideglusib (a TDZD compound) have been studied in clinical trials. However, these two compounds have drawbacks, namely lithium carbonate shows a weak inhibition ($IC_{50}$, 2 mM) and tideglusib ($IC_{50}$, 100 nM) irreversibly inhibits GSK-3β thereby undermining normal functions of the enzyme. In recent years, strategies have been employed to search for selective GSK-3β inhibitors, particularly those are not ATP-site directed. It is known that the substrate domain of GSK-3β is less conserved and exhibits a unique folding pattern compared to other kinases. Inhibitors targeting this site are thought to be more specific and selective than the ATP-competitive inhibitors. Yet few substrate-competitive inhibitors of GSK-3β have been reported.

Isoorientin, a 6-C-glycosylflavone, has been shown to alleviate tau phosphorylation and amyloid neurotoxicity through GSK-3β inhibition (Liang, et al. (2016) *ACS Chem. Neurosci.* 7(7):912-923). In addition, isoorientin and related natural flavones attenuate Aβ burden and neuroinflammation in an APPswe/PSEN1dE9 mouse model of Alzheimer's disease (Song, et al. (2017) *PLoS ONE* 12:30169509). However, the lack of druggable potency commonly suffered by bioactive natural products makes it challenging in pharmaceutical applications.

SUMMARY OF THE INVENTION

This invention is a compound of Formula I, or a pharmaceutically acceptable salt, solvate or prodrug thereof:

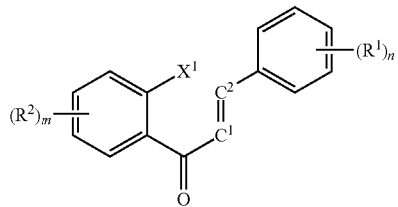

Formula I wherein n is 0 or an integer from 1 to 3; m is an integer from 1 to 3; $R^1$ is substituted anywhere on the ring, wherein each $R^1$ is independently a hydrogen, hydroxyl, alkylamino, or alkoxyl group; $R^2$ is substituted anywhere on the ring, wherein each $R^2$ is independently a hydrogen, hydroxyl, substituted or unsubstituted alkyl, substituted or unsubstituted alkoxyl, substituted or unsubstituted heterocyclyl, substituted or unsubstituted aryl, or substituted or unsubstituted heteroaryl group; and $X^1$ is a hydrogen or $X^1$ is an oxygen, nitrogen or sulfur bonded to carbon $C^1$ or $C^2$ to form a 5- or 6-membered heteroaryl ring, respectively.

In some embodiments, the compound of this invention has the structure of Formula II:

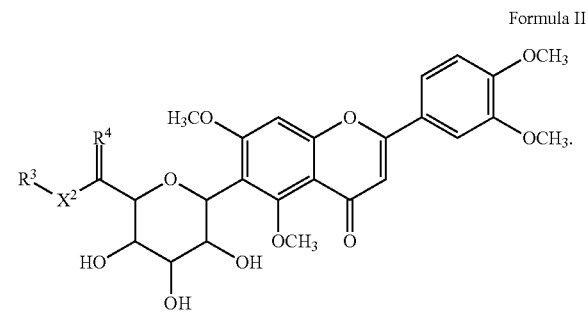

Formula II wherein $R^3$ is a hydrogen, substituted or unsubstituted alkyl, substituted or unsubstituted alkoxyl, substituted or unsubstituted cycloalkyl, substituted or unsubstituted heterocyclyl, substituted or unsubstituted aryl, or substituted or unsubstituted heteroaryl group; $R^4$ is a $H_2$ or O; and $X^2$ is O, NH or $CH_2$. In particular embodiments of Formula II, $R^3$ is a substituted or unsubstituted alkyl, substituted or unsubstituted alkoxyl, substituted or unsubstituted cycloalkyl, or substituted or unsubstituted heterocyclyl; $R^4$ is O; and $X^2$ is NH.

In some embodiments, the compound of this invention has the structure of Formula III:

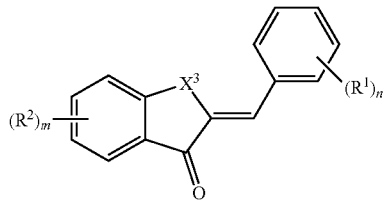

Formula III wherein $X^3$ is —O—, —NH, —S— or —O—C—. In particular embodiments of Formula III, n is 2; m is 2; each $R^1$ is independently a hydroxyl or alkoxyl group; each $R^2$ is independently a hydroxyl or substituted heterocyclyl group and $X^3$ is —O— or —O—C—.

In further embodiments, the compound of this invention has the structure of Formula IV:

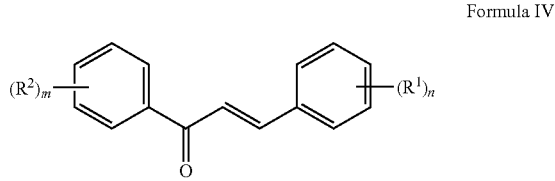

Formula IV

In particular embodiments of Formula IV, n is 1 or 2; m is 1; each $R^1$ is independently a hydroxyl or alkoxyl group; and $R^2$ a hydroxyl group.

This invention also provides a pharmaceutical composition containing a compound of Formula I (including Formula II, III and IV) and at least one pharmaceutically acceptable carrier, adjuvant, or vehicle. Moreover, this invention provides methods for treating a cognitive, neurodegenerative or neurological disease or condition (e.g., Alzheimer's disease), as well as cancer, obesity, diabetes, an inflammatory or autoimmune disease, cardiovascular disorder, metabolic syndrome X, hair loss, severe acute respiratory syndrome coronavirus, cocaine addiction, dental caries, bone loss or glaucoma by administering to a subject in need of treatment a therapeutically effective amount of a compound of this invention.

DETAILED DESCRIPTION OF THE INVENTION

Figure 1:
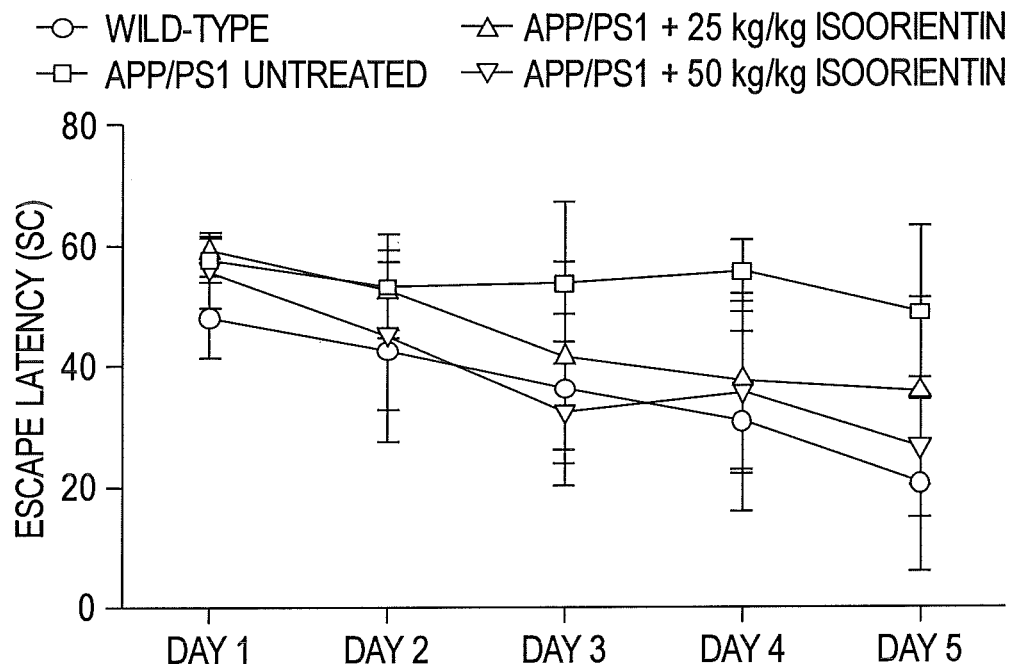
FIG. 1 shows the escape latency of wild-type and APP/PS1 transgenic mice in a Morris water maze trial. $*P<0.05$. n=10.

GSK-3β plays a central role in signaling pathways of neurodegenerative diseases such as Alzheimer's disease, as well as inflammatory diseases, cancer, and diabetes. Discovery of selective inhibitors targeting the substrate site of GSK-3β has emerged as a rational and feasible strategy for inhibiting this enzyme. Unlike inhibitors targeting the ATP binding site, inhibitors targeting the substrate site on GSK-3β have fewer off-target effects. A new structural class of substrate-competitive inhibitors of GSK-3β have now been developed based upon the structure of isoorientin (1), which contains a 6-C-glycosylflavone scaffold.

1

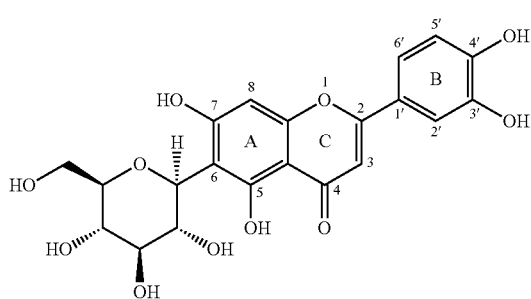

The structure-activity relationship analysis, in vitro enzymatic kinetics, and in silico docking studies described herein indicate that both the presence and position of C-glycone on the flavone core are features that facilitate binding to the substrate site on GSK-3β. A flavone core alone is promiscuous and tends to bind the ATP site and thus lose the required selectivity. The presence of a C-glycone at 8-position ($IC_{50}$, >5 mM) rather than 6-position ($IC_{50}$, 185 µM) results in an unfavorable binding pose to the substrate site likely due to the loss of key hydrogen bonds with Gln89, Asp90, Asn95, and Arg96. Based upon the structure-activity relationship analysis, a semi-synthetic series isoorientin analogues that selectively inhibit GSK-3β at the substrate site were generated. Data indicate that the new lipophilic amide analogues disclosed herein increase the potency against GSK-3β by 3- to 310-fold and passive membrane permeability by 2.6- to 4.4-fold relative to isoorientin. In addition, systematic modifications of the carbon-chain length and ring size and bioisosteric replacement in the $R_2$-group on the C-glycone of isoorientin infers a dramatic GSK-3β potency improvement. The structural modifications contribute hydrophobic affinities with Phe67, Val87 and Leu88 in the substrate site of GSK-3β, which is concurrently supported by the Ligand-lipophilic efficiency (LiPE) analysis (LiPE highlights potency changes to the net of lipophilicity). Moreover, the analogues described herein alleviate tau hyperphosphorylation and Aβ neurotoxicity through GSK-3β inhibition in the human SH-SY5Y neuronal model of Alzheimer's disease.

Accordingly, this invention provides a GSK-3β inhibitor of Formula I, or a pharmaceutically acceptable salt, solvate or prodrug thereof:

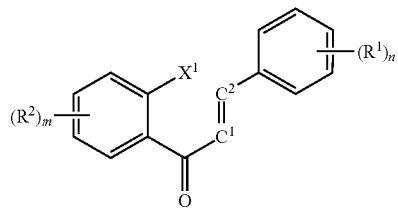

Formula I wherein
n is 0 or an integer from 1 to 3;
m is an integer from 1 to 3;
$R^1$ is substituted anywhere on the ring, wherein each $R^1$ is independently a hydrogen, hydroxyl (—OH), alkylamino, or alkoxyl group;
$R^2$ is substituted anywhere on the ring, wherein each $R^2$ is independently a hydrogen, hydroxyl, substituted or unsubstituted alkyl, substituted or unsubstituted alkoxyl, substituted or unsubstituted heterocyclyl, substituted or unsubstituted aryl, or substituted or unsubstituted heteroaryl group; and
$X^1$ is a hydrogen or $X^1$ is an oxygen, nitrogen or sulfur bonded to carbon $C^1$ or $C^2$ thereby forming a 5- or 6-membered heteroaryl ring, respectively.

In particular embodiments, the GSK-3β inhibitor of Formula I is not isoorientin, isovitexin, orientin, luteolin or other natural products such as hispidol, a compound having the following structure:

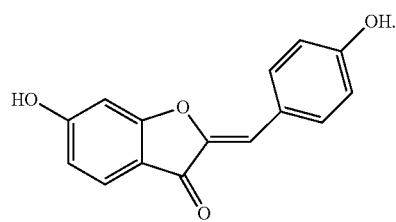 [SMILES: O=C1/C(=C/c2ccc(O)cc2)Oc2cc(O)ccc21]

In some embodiments, the GSK-3β inhibitor of this invention is a compound of Formula II, or a pharmaceutically acceptable salt, solvate or prodrug thereof:

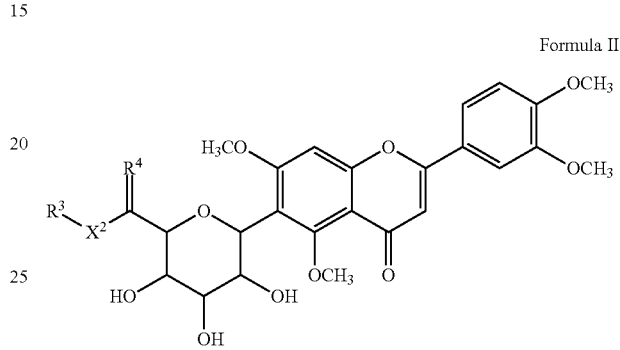

Formula II wherein
$R^3$ is a hydrogen, substituted or unsubstituted alkyl, substituted or unsubstituted alkoxyl, substituted or unsubstituted cycloalkyl, substituted or unsubstituted heterocyclyl, substituted or unsubstituted aryl, or substituted or unsubstituted heteroaryl group;
$R^4$ is a $H_2$ or O; and
$X^2$ is O, $CH_2$ or NH.

In certain embodiments, $R^3$ is a substituted or unsubstituted alkyl, substituted or unsubstituted alkoxyl, substituted or unsubstituted cycloalkyl, or substituted or unsubstituted heterocyclyl; $R^4$ is O; and $X^2$ is NH.

In other embodiments, the GSK-3β inhibitor of this invention is a compound of Formula IIa, or a pharmaceutically acceptable salt, solvate or prodrug thereof:

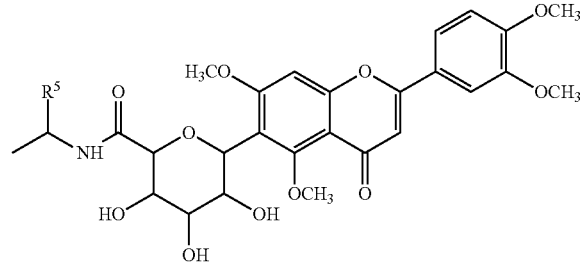

Formula IIa wherein
$R^5$ is a hydrogen, substituted or unsubstituted alkyl or substituted or unsubstituted cycloalkyl group.

In particular embodiments, the GSK-3β inhibitor of this invention is a compound of Formula IIa, wherein $R^5$ is a substituted or unsubstituted alkyl.

In some embodiments, the GSK-3β inhibitor of this invention is a compound of Formula III, or a pharmaceutically acceptable salt, solvate or prodrug thereof:

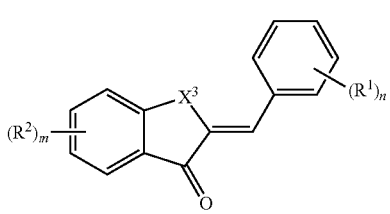

Formula III wherein n, m, $R^1$ and $R^2$ are as previously defined in Formula I and $X^3$ is —O—, —NH—, —S— or —O—C. In certain embodiments, n is 2; m is 2; each $R^1$ is independently a hydroxyl or alkoxyl group; each $R^2$ is independently a hydroxyl or substituted heterocyclyl group and $X^3$ is —O—, —NH—, —S— or —O—C—.

In other embodiments, the GSK-3β inhibitor of this invention is a compound of Formula IIIa, or a pharmaceutically acceptable salt, solvate or prodrug thereof:

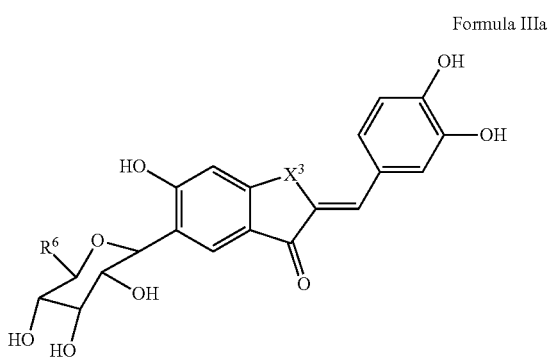

Formula IIIa wherein $X^3$ is —O—, —NH—, —S— or —O—C— and $R^6$ is a substituted alkyl group.

In some embodiments, the GSK-3β inhibitor of this invention is a compound of Formula IV, or a pharmaceutically acceptable salt, solvate or prodrug thereof:

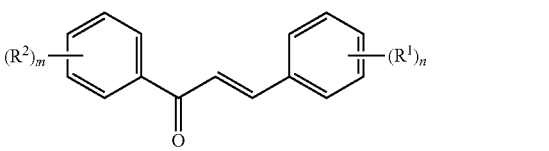

Formula IV wherein n, m, $R^1$ and $R^2$ are as previously defined in Formula I. In certain embodiments, n is 1 or 2; m is 1; each $R^1$ is independently a hydroxyl or alkoxyl group; and $R^2$ a hydroxyl group.

In other embodiments, the GSK-3β inhibitor of this invention is a compound of Formula IVa, or a pharmaceutically acceptable salt, solvate or prodrug thereof:

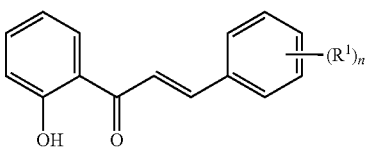

Formula IVa wherein n and $R^1$ are as previously defined in Formula I. In particular embodiments, the GSK-3β inhibitor of this invention is a compound of Formula IVa, wherein n is 1 or 2 and each $R^1$ is independently a hydroxyl group or alkoxyl group.

As used herein, an "alkyl" group refers to saturated or unsaturated aliphatic hydrocarbon group. The alkyl group may be a straight or linear chain and may optionally be substituted. The alkyl group may have 1 to 6 carbon atoms, i.e., $C_1$-$C_5$, wherein the numerical range "1 to 6" refers to each integer in the given range, e.g., "1 to 6 carbon atoms" means that the alkyl group may have 1 carbon atom, 2 carbon atoms, 3 carbon atoms, etc., up to and including 6 carbon atoms. By way of example, "$C_2$-$C_4$ alkyl" indicates that there are two to four carbon atoms in the alkyl chain, i.e., the alkyl chain is selected from among ethyl, n-propyl, i-propyl, n-butyl, and t-butyl. Thus, $C_2$-$C_4$ alkyl includes $C_2$-$C_3$ alkyl and $C_3$-$C_4$ alkyl. Alkyl groups of use in a compound of Formula I include methyl, ethyl, n-propyl, i-propyl, n-butyl, t-butyl, n-pentyl and hexyl groups.

"Alkoxy" groups are oxygen ethers formed from the previously described straight or linear alkyl groups. In particular embodiments, the alkoxyl is a $C_1$-$C_3$ alkoxy group, which may optionally be substituted. In certain embodiments, the alkoxy is a methoxy or ethoxy group.

"Alkylamino" refers to a —N(R)$_2$ radical, wherein R is alkyl.

"Cycloalkyl" is used herein to mean a cyclic alkyl group, which may optionally be substituted. The cycloalkyl group may have 3 to 10 carbon atoms, i.e., $C_3$-$C_{10}$, wherein the numerical range "3 to 10" refers to each integer in the given range, e.g., "3 to 10 carbon atoms" means that the cycloalkyl group may have 3 carbon atom, 4 carbon atoms, 5 carbon atoms, etc., up to and including 10 carbon atoms. Cycloalkyl groups of use in a compound of Formula I include, but not limited to, cyclopropyl, cyclobutyl, cyclopentyl, cyclohexyl, cycloheptyl, cyclooctyl, cyclodecanyl and adamantly groups.

"Heterocyclyl" refers to a saturated monocyclic or polycyclic group which is composed of carbon atoms and at least one heteroatom (e.g., 1 to 5 heteroatoms). As with cycloalkyl, the heterocyclyl may have 3 to 10 ring atoms and may optionally be substituted. In certain embodiments, the heterocycle is a monocyclic or bicyclic group, wherein the ring includes 2 to 6 carbon atoms and 1 to 3 heteroatoms, wherein each heteroatom is independently a nitrogen, carbon or sulfur atom. Examples of heterocyclyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means a polyunsaturated, aromatic, hydrocarbon group, which can be a single ring or multiple rings (preferably from 1 to 3 rings) that are fused together (i.e., a fused ring aryl). The term "heteroaryl" refers to aryl groups that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). Aryl and heteroaryl groups of this invention are preferably monocyclic or bicyclic and include between 3 and 10 ring atoms (i.e., $C_{3-10}$ aryl; and $C_{2-6}$ heteroaryl with 1 to 3 heteroatoms), one or more of which may optionally be substituted. Nonlimiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

Examples of substituents of the alkyl, alkoxy, cycloalkyl, heterocyclyl, aryl, and heteroaryl groups independently include (1) halogen atoms (e.g., fluorine atom, chlorine atom, bromine atom, iodine atom, etc.), (2) nitro, (3) cyano, (4) hydroxy or oxo, (5) $C_{1-6}$ alkoxy optionally having 1 to 3 halogen atoms (e.g., fluorine, chlorine, bromine, iodine) (e.g., methoxy, ethoxy, propoxy, isopropoxy, butoxy, isobutoxy, sec-butoxy, pentyloxy, hexyloxy, fluoromethoxy, etc.), (6) $C_{6-14}$ aryloxy (e.g., phenyloxy, naphthyloxy, etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy, etc.), (8) mercapto, (9) $C_{1-6}$ alkylthio optionally having 1 to 3 halogen atoms (e.g., fluorine, chlorine, bromine, iodine) (e.g., methylthio, difluoromethylthio, trifluoromethylthio, ethylthio, propylthio, isopropylthio, butylthio, 4,4,4-trifluorobutylthio, pentylthio, hexylthio, etc.), (10) $C_{6-14}$ arylthio (e.g., phenylthio, naphthylthio, etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio, etc.) (12) amino, (13) mono-$C_{1-6}$ alkylamino (e.g., methylamino, ethylamino etc.), (14) mono-$C_{6-14}$ acylamino (e.g., phenylamino, 1-naphthylamino, 2-naphthylamino, etc.), (15) mono-$C_{7-16}$ aralkylamino (e.g., benzylamino, etc.), (16) di-$C_{1-6}$ alkylamino (e.g., dimethylamino, diethylamino, etc.), (17) di-$C_{6-14}$ arylamino (e.g., diphenylamino, etc.), (18) di-$C_{7-16}$ aralkylamino (e.g., dibenzylamino, etc.), (19) formyl, (20) $C_{1-6}$ alkyl-carbonyl (e.g., acetyl, propionyl, etc.), (21) $C_{6-14}$ arylcarbonyl (e.g., benzoyl, 1-naphthoyl, 2-naphthoyl, etc.), (22) carboxyl, (23) $C_{1-6}$ alkoxy-carbonyl (e.g., methoxycarbonyl, ethoxycarbonyl, propoxycarbonyl, tert-butoxycarbonyl, etc.), (24) $C_{6-14}$ aryloxy-carbonyl (e.g., phenoxycarbonyl, etc.), (25) carbamoyl, (26) thiocarbamoyl, (27) mono-$C_{1-6}$ alkyl-carbamoyl (e.g., methylcarbamoyl, ethylcarbamoyl, etc.), (28) di-$C_{1-6}$ alkyl-carbamoyl (e.g., dimethylcarbamoyl, diethylcarbamoyl, ethylmethylcarbamoyl, etc.), (29) $C_{6-14}$ aryl-carbamoyl (e.g., phenylcarbamoyl, 1-naphthylcarbamoyl, 2-naphthylcarbamoyl, etc.), (30) $C_{1-6}$ alkylsulfonyl (e.g., methylsulfonyl, ethylsulfonyl, etc.), (31) $C_{6-14}$ arylsulfonyl (e.g., phenylsulfonyl, 1-naphthylsulfonyl, 2-naphthylsulfonyl, etc.), (32) $C_{1-6}$ alkylsulfinyl (e.g., methylsulfinyl, ethylsulfinyl, etc.), (33) $C_{6-14}$ arylsulfinyl (e.g., phenylsulfinyl, 1-naphthylsulfinyl, 2-naphthylsulfinyl, etc.), (34) formylamino, (35) $C_{1-6}$ alkyl-carbonylamino (e.g., acetylamino, etc.), (36) $C_{6-14}$ aryl-carbonylamino (e.g., benzoylamino, naphthoylamino, etc.), (37) $C_{1-6}$ alkoxy-carbonylamino (e.g., methoxycarbonylamino, ethoxycarbonylamino, propoxycarbonylamino, butoxycarbonylamino, etc.), (38) $C_{1-6}$ alkylsulfonylamino (e.g., methylsulfonylamino, ethylsulfonylamino, etc.), (39) $C_{6-14}$ arylsulfonylamino (e.g., phenylsulfonylamino, 2-naphthylsulfonylamino, 1-naphthylsulfonylamino, etc.), (40) $C_{1-6}$ alkyl-carbonyloxy (e.g., acetoxy, propionyloxy, etc.), (41) $C_{6-14}$ aryl-carbonyloxy (e.g., benzoyloxy, naphthylcarbonyloxy, etc.), (42) $C_{1-6}$ alkoxy-carbonyloxy (e.g., methoxycarbonyloxy, ethoxycarbonyloxy, propoxycarbonyloxy, butoxycarbonyloxy, etc.), (43) mono-$C_{1-6}$ alkyl-carbamoyloxy (e.g., methylcarbamoyloxy, ethylcarbamoyloxy, etc.), (44) di-$C_{1-6}$ alkyl-carbamoyloxy (e.g., dimethylcarbamoyloxy, diethylcarbamoyloxy, etc.), (45) $C_{6-14}$ aryl-carbamoyloxy (e.g., phenylcarbamoyloxy, naphthylcarbamoyloxy, etc.), (46) a 5- to 7-membered saturated cyclic amino optionally containing, besides one nitrogen atom and carbon atom, 1 or 2 kinds of 1 to 4 heteroatoms selected from a nitrogen atom, a sulfur atom and an oxygen atom (e.g., pyrrolidin-1-yl, piperidino, piperazin-1-yl, morpholino, thiomorpholino, hexahydroazepin-1-yl, etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), (48) $C_{1-3}$ alkylenedioxy (e.g., methylenedioxy, ethylenedioxy, etc.), (49) $C_{3-7}$ cycloalkyl (e.g., cyclopropyl, cyclobutyl, cyclopentyl, cyclohexyl, cycloheptyl, etc.) and combinations thereof. In certain embodiments, the number of the substituents is 1 to 3, e.g., 1, 2 or 3. In particular embodiments, cycloalkyl, heterocyclyl, aryl, and heteroaryl groups are substituted at one or more of the para, meta and/or ortho positions.

Preferred compounds of the invention are selected from the following compounds:

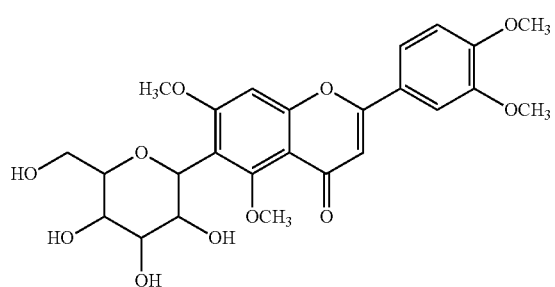

5

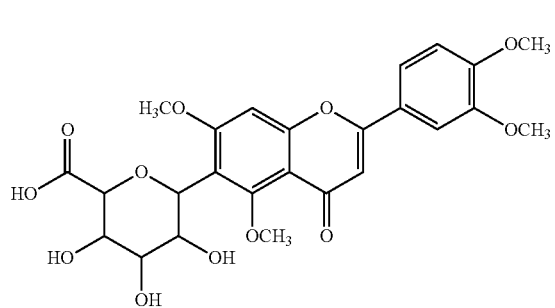

6

7
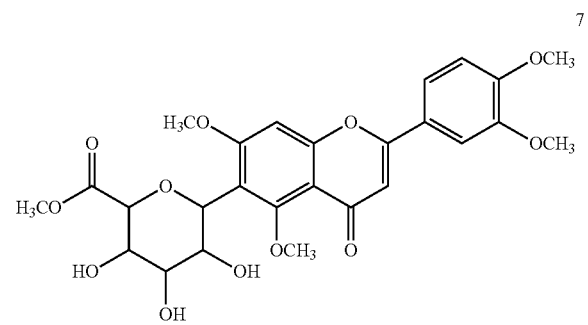
8
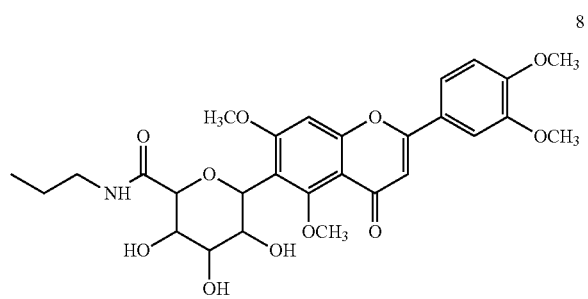
9
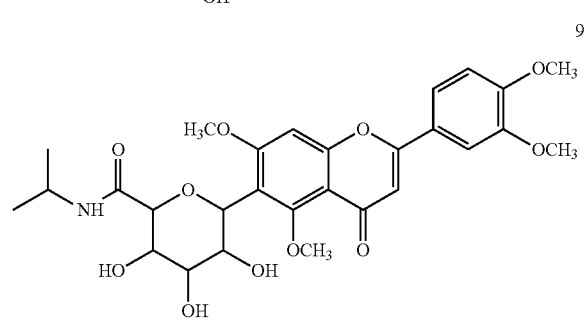
10
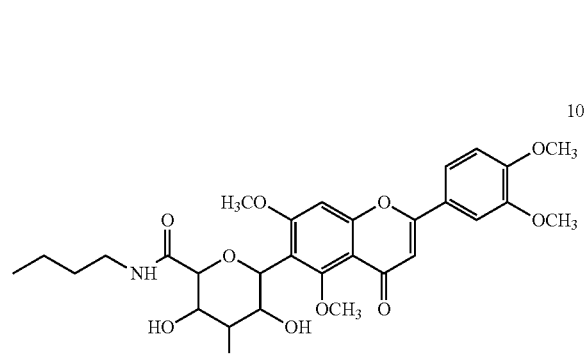
11
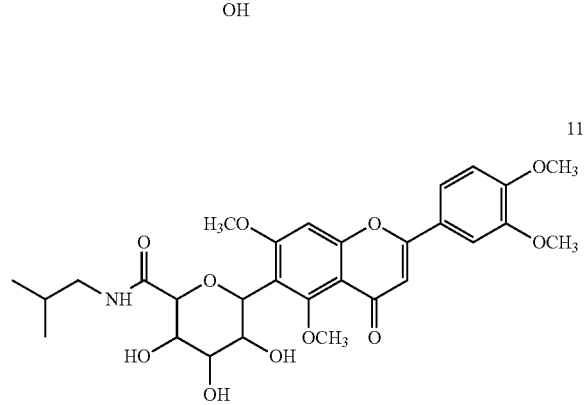
12
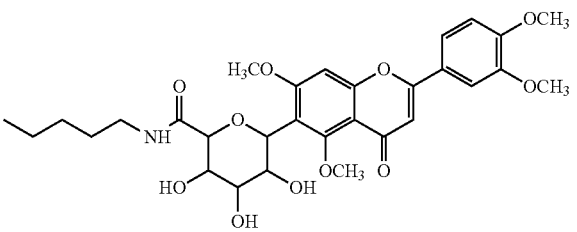
13
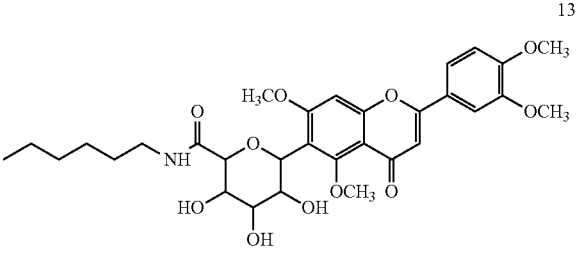
14
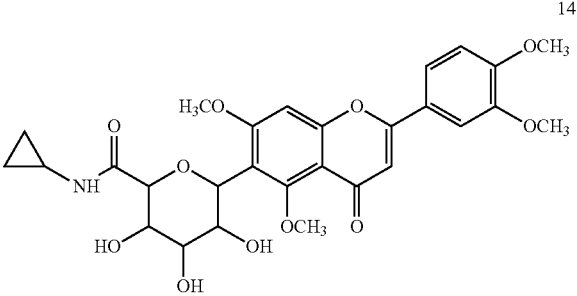
15
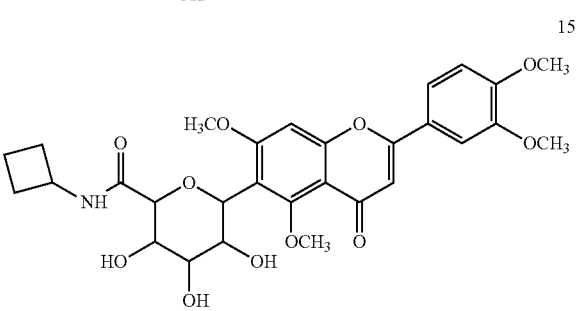
16
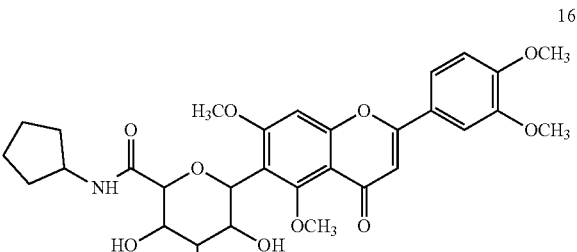
17
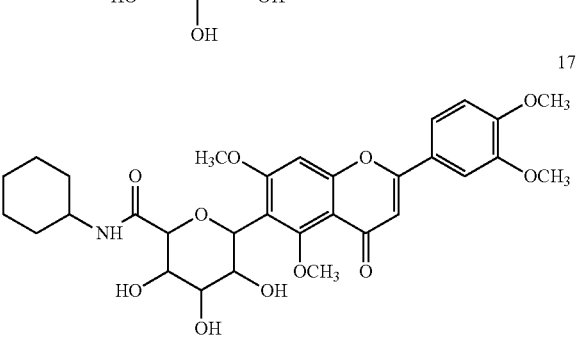

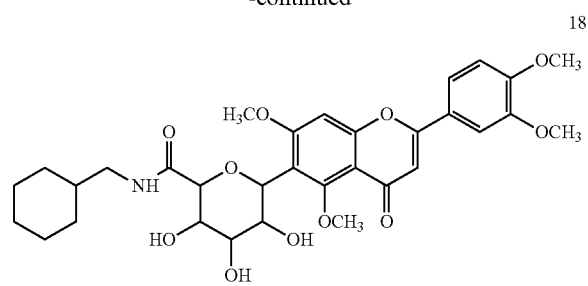
18
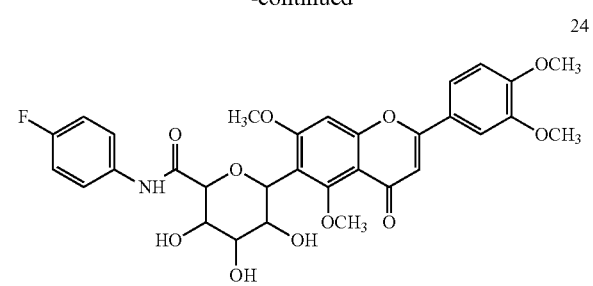
24
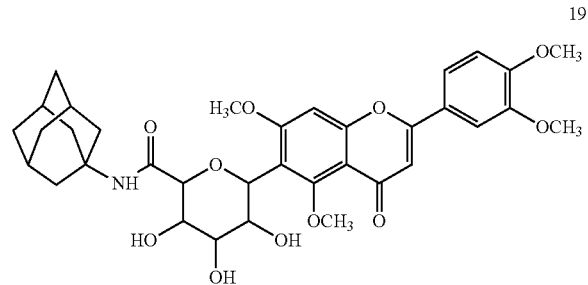
19
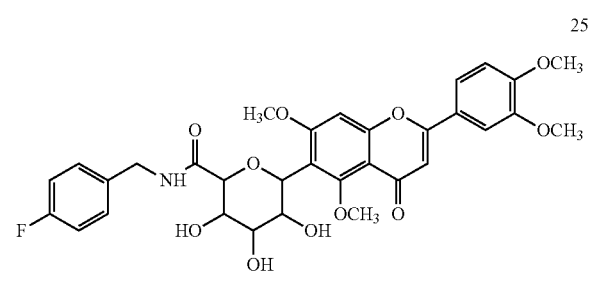
25
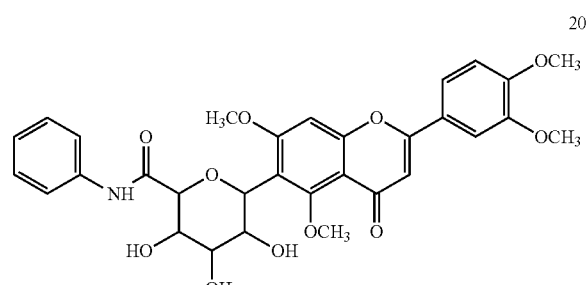
20
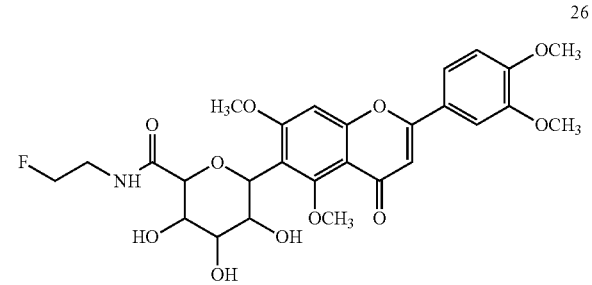
26
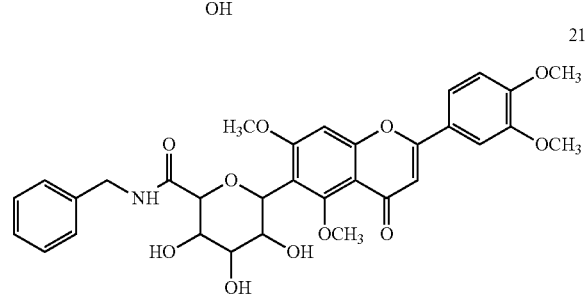
21
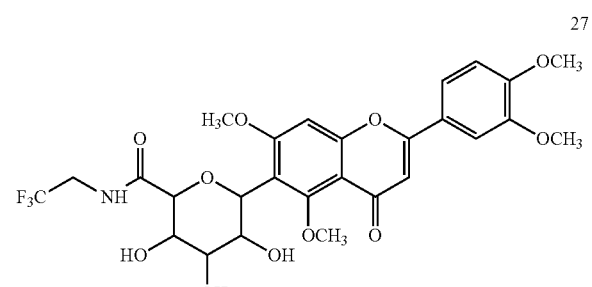
27
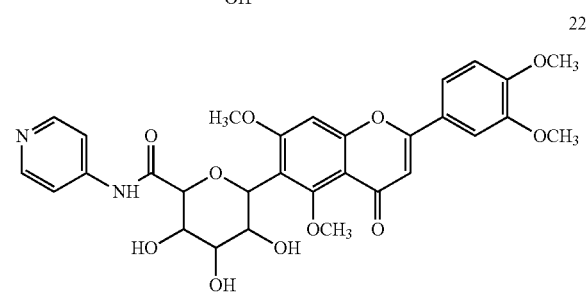
22
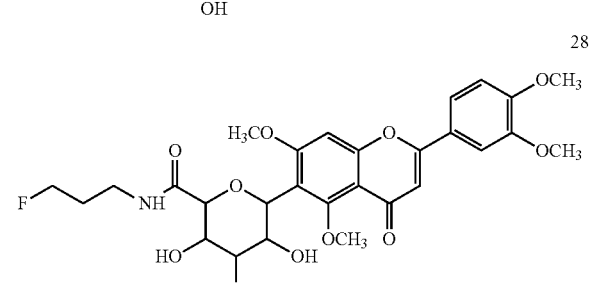
28
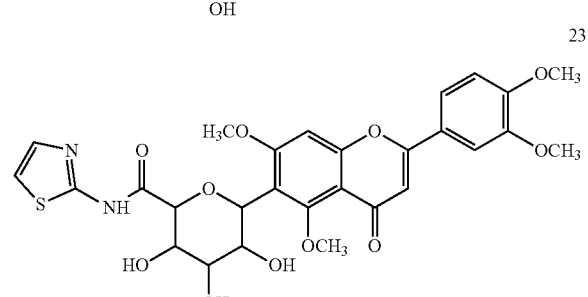
23
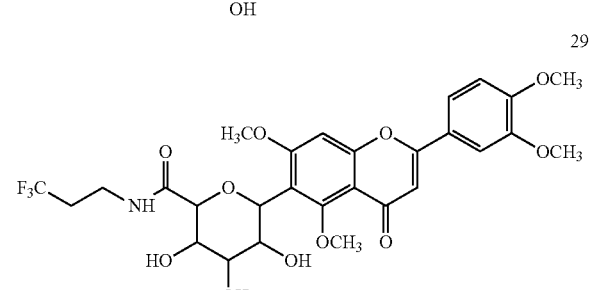
29

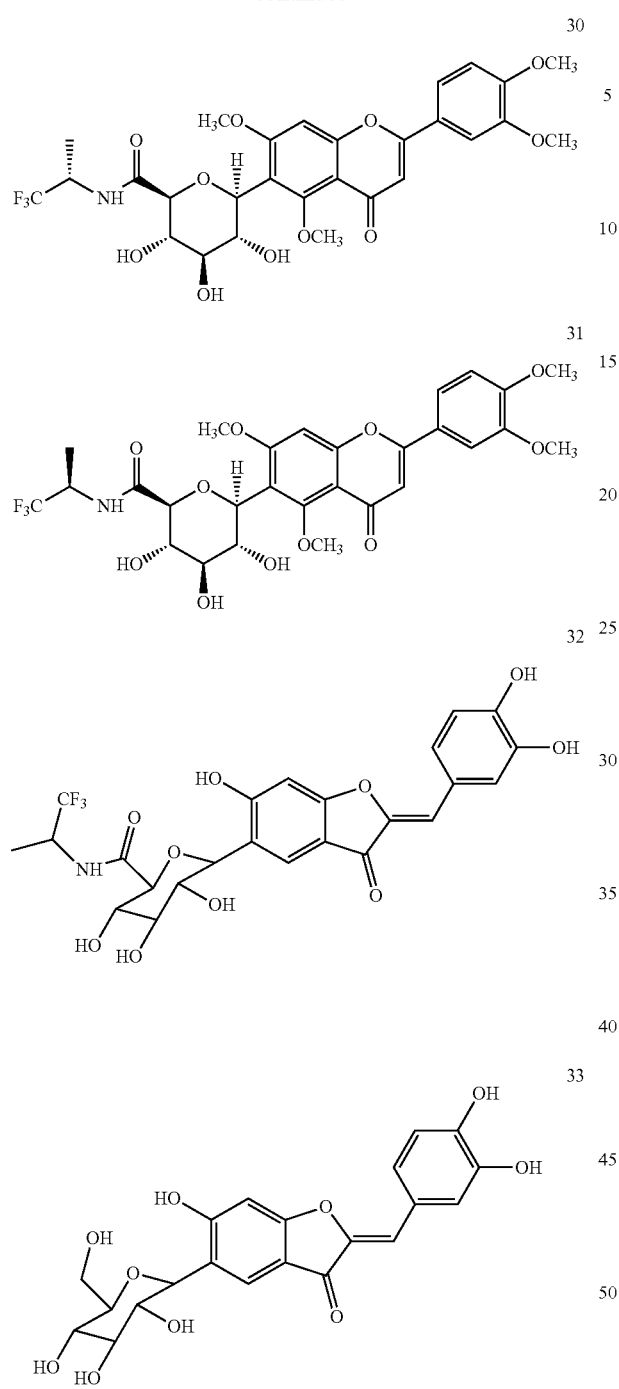

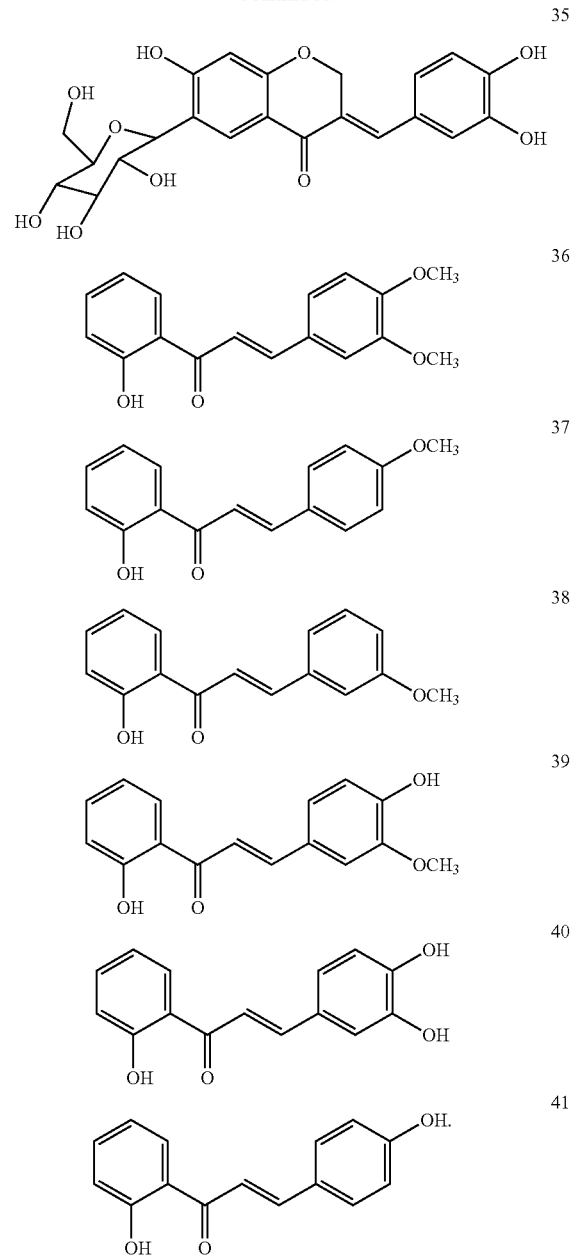

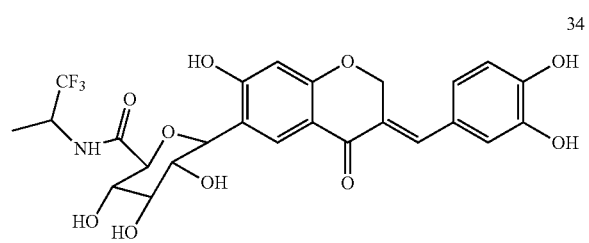

The term "pharmaceutically acceptable salt" refers to a salt which, upon administration to a recipient is capable of providing (directly or indirectly) a compound as described herein. The preparation of salts can be carried out by methods known in the art. Preferably, "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminum and lithium salts, and organic alkali salts such as, for example, ethylenediamine, ethanolamine, N,N-dialkylenethanolamine, triethanolamine, glucamine and basic amino acids salts.

The term "solvate" according to this invention is to be understood as meaning any form of the active compound according to the invention which has another molecule (ideally a polar solvent) attached to it via a non-covalent bonding. Examples of such solvates include hydrates and alcoholates, e.g., methanolates.

The term "prodrug" as used herein refers to a chemical compound having undergone a chemical derivation such as substitution or addition of a further chemical group to change (for pharmaceutical use) any of its physico-chemical properties, such as solubility or bioavailability, e.g., ester and ether derivatives of an active compound that yield the active compound per se after administration to a subject. Examples of well-known methods of producing a prodrug of a given acting compound are known to those skilled in the art and can be found in, e.g., Krogsgaard-Larsen, et al. (2002) *Textbook of Drug design and Discovery*, Taylor & Francis.

Particularly favored prodrugs are those that increase the bioavailability of the compounds of this invention when such compounds are administered to a subject (e.g., by allowing an orally administered compound to be more readily absorbed into the blood) or which enhance delivery of the parent compound to a biological compartment (e.g., the brain or lymphatic system) relative to the parent species.

The preparation of salts, solvates and prodrugs can be carried out by methods known in the art. It will be appreciated that non-pharmaceutically acceptable salts, solvates or prodrugs also fall within the scope of the invention since those may be useful in the preparation of pharmaceutically acceptable salts, solvates or prodrugs.

The compounds of the invention may be in crystalline form either as free compounds or as solvates (e.g., hydrates) and it is intended that both forms are within the scope of the present invention. Methods of solvation are generally known within the art. Suitable solvates are pharmaceutically acceptable solvates. In a particular embodiment the solvate is a hydrate.

The compounds of the present invention may exhibit tautomerism. Tautomers are one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{11}$C-, $^{13}$C- or $^{14}$C-enriched carbon, $^{15}$N-enriched nitrogen or $^{18}$F-enriched fluorine are within the scope of this invention.

The compounds of the invention can be synthesized by available procedures. In a particular embodiment, certain compounds of Formula I are prepared following the procedure depicted in Scheme 1, which involves chemoselective methylation of isoorientin followed by one or more of chemoselective oxidation, methyl esterification and/or amidation.

Given the role of GSK-3β in neurodegenerative diseases, inflammatory diseases, cancer, and diabetes, this invention also provides a method for using a GSK-3β inhibitor of this invention, i.e., a compound of Formula I, Formula II, Formula IIa, Formula III, Formula IIIc, Formula IV, Formula IVa, or a combination thereof, for the therapeutic treatment of a disease or condition resulting from or associated with the dysregulation of GSK-3β activity. In accordance with this method of the invention, a subject in need of treatment is administered a therapeutically effective amount of a compound of Formula I, Formula II, Formula IIa, Formula III, Formula IIIc, Formula IV, Formula IVa, or a combination, pharmaceutically acceptable salt, solvate or prodrug thereof so that the subject's disease or condition is treated.

Generally, a "therapeutically effective amount" of the compound of the invention or a pharmaceutical composition thereof will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The term "treatment" or "to treat" in the context of this invention means administration of a compound or formulation according to the invention to prevent, ameliorate or eliminate the disease or one or more symptoms associated with said disease. "Treatment" also encompasses preventing, ameliorating or eliminating the physiological sequelae of the disease. The term "ameliorate" is understood as meaning any improvement in the situation of the subject that has been treated, either subjectively (feeling of the subject) or objectively (measured parameters).

Dysregulation of GSK-3β activity has been associated a number of cognitive, neurodegenerative or neurological diseases or conditions. Accordingly, the GSK-3β inhibitors of this invention are of particular use in the treatment of cognitive, neurodegenerative or neurological diseases or conditions such as Alzheimer's disease (Hernandez, et al. (2009) *Brain Res. Bull.* 80(4-5):248-50), mild cognitive impairment (Forlenza, et al. (2011) *J. Psychiatr. Res.* 45(2): 220-4), Parkinson's disease (Masahiro & Hideaki (2009) *Neurosci. Lett.* 449(2):103-107), frontotemporal dementia (Schaffer, et al. (2008) *Arch. Neurol.* 65:1368-74), frontotemporal lobar degeneration associated with Pick bodies (Hanger & Noble (2011) *Int. J. Alzheimer's Dis.* 2011: 352805, Pick's disease, progressive supranuclear palsy, subacute sclerosing panencephalitis, postencephalitic parkinsonism, chronic traumatic encephalopathy (CTE, formerly dementia pugilistica), guam parkinsonism-dementia complex, corticobasal degeneration, argyrophilic grain disease, familial frontotemporal dementia and parkinsonism linked to chromosome 17 due to mutations in the tau gene (FTDP-17-tau) and other tauopathies (Buée, et al. (2000) *Brain Res. Rev.* 33:95-130), AIDS-associated dementia (Dewhurst, et al. (2007) *J. Neuroimmune Pharmacol.* 2(1):93-96), Huntington's disease (Carmichael, et al. (2002) *J. Biol. Chem.*

277(37):33791-8), Lewy body disease (Tanji, et al. (2003) *Neuropathology* 23β):199-202), bipolar disorder (Roew, et al. (2007) *Neurosci. Biobehav. Rev.* 31(6):920-931; Li, et al. (2002) *Bipolar Disord.* 4(2):137-144), depression (Wada (2009) *J. Pharmacol. Sci.* 110(1):14-28), schizophrenia (Koros & Dorner-Ciossek (2007) *Drug News Perspect.* 20(7): 437-45; Lovestone, et al. (2007) *Trends Neurosci.* 30(4): 142-9), epilepsy (Chen, et al. (1999) *J. Neurochem.* 72(3): 1327-30), mood disorders (Jope & Roh (2006) *Curr. Drug Targets* 7(11):1421-34), autism (Beaulieu, et al. (2008) *Proc. Natl. Acad. Sci. USA* 105(4):1333-8), attention deficit hyperactivity disorder (Beaulieu, et al. (2004) *Proc. Natl. Acad. Sci. USA* 101(14):5099-104), Down's syndrome (Liu, et al. (2008) *FASEB J.* 22(9):3224-33), fragile X syndrome (FXS) (Yuskaitis, et al. (2010) *Biochem. Pharmacol.* 79(4):632-46), diseases associated with ischemia/reperfusion and shock (Dugo, et al. (2007) *Shock* 27(2):113-23), brain injury (Sasaki, et al. (2001) *Neurol. Res.* 23(6):588-92), multiple sclerosis (Beurel, et al. (2010) *Trends Immunol.* 31(1):24-31) and other autoimmune and inflammatory diseases afflicting the central nervous system (De Sarno, et al. (2008) *J. Immunol.* 181(1):338-45), spinocerebellar ataxia type 1 (Watase, et al. (2007) *PLoS Med.* 4(5):836-847), cerebral bleeding for example, due to solitary cerebral amyloid angiopathy (Han, et al. (2008) *Neuroscience* 153(2):414-27), amyotrophic lateral sclerosis (Yang, et al. (2008) *Brain Res.* 1196:131-139), prion disease (Pérez, et al. (2003) *Biochem J.* 15:372 (Pt 1):129-36), Gerstman-Sträussler-Scheinker disease (Wang, et al. (2010) *BMC Infect Dis.* 10:86), Hallervorden-Spatz disease and multiple systems atrophy (Yuan, et al. (2008) *Cell Mol. Neurobiol.* 28(1):21-33), anxiety disorder or myotonic dystrophy (Jin, et al. (2009) *Cell Cycle* 8(15):2356-9).

Dysregulation of GSK-3β activity in inflammatory and autoimmune diseases or conditions has also been described. Accordingly, the GSK-3β inhibitors of this invention are of use in the treatment of chronic inflammatory diseases including rheumatoid arthritis, inflammatory bowel disease and psoriasis (Cohen (2001) *Eur. J. Biochem.* 268(19):5001-10), arthritis (Cuzzocrea, et al. (2006) *Clin. Immunol.* 120: 57-67), peritonitis (Hu, et al. (2006) *Immunity* 24:563-574), systemic inflammation, renal dysfunction and hepatotoxicity in endotoxemia (Dugo, et al. (2005) *Crit. Care Med.* 33:1903-1912), asthma (Bentley, et al. (2009) *Am. J. Physiol. Lung Cell Mol. Physiol.* 296(2):L176-84), sepsis (Evenson, et al. (2005) *J. Biochem. Cell. Biol.* 37:2226-2238), colitis (Whittle, et al. (2006) *Br. J. Pharmacol.* 147:575-582), inflammation-induced organ injury caused by hemorrhage and resuscitation (Dugo, et al. (2006) *Shock* 25:485-491), inflammatory injury in chronic renal allograft disease (Gong, et al. (2008) *Am. J. Transplant.* 8(9):1852-63) or lupus (Lenz, et al. (1995) *Int. J. Immunopharmacol.* 17:581-592).

Cardiovascular disorders that can be treated in accordance with the methods of this invention include heart disease (Hardt & Sadoshima (2002) *Circ. Res.* 90:1055-63), atherosclerosis (Bowes, et al. (2009) *Am. J. Pathol.* 174(1):330-42), hypertension (Badorff, et al. (2002) *J. Clin. Invest.* 109(3):373-381), restenosis (Ma, et al. (2010) *Cardiovasc Res.* 86(2):338-45) or leukopenia.

Additional pathologies associated with GSK-3β, which can be treated with the inhibitors described herein, are cancer, obesity, diabetes, metabolic syndrome X (Wagman, et al. (2004) *Curr. Pharm. Des.* 10(10):1105-37), hair loss (Lyubimova, et al. (2010) *J. Clin. Invest.* 120(2):446-56), severe acute respiratory syndrome coronavirus (Wu, et al. (2009) *J. Biol. Chem.* 284(8):5229-39), cocaine addiction (Xu, et al. (2009) *J. Neurochem.* 111(6):1357-68), bone loss (Wang, et al. (2009) *Life Sci.* 85(19-20):685-92), or glaucoma (Wang, et al. (2008) *J. Clin. Invest.* 118(3):1056-64). In addition, collagen sponges infused with GSK3 inhibitors have been shown to promote the formation of dentine, leading to repair of dental caries (Neves, et al. (2017) *Sci. Reports* 7:39654). Accordingly, the GSK-3β inhibitors of this invention also find use in regenerative endodontics.

The present invention further provides pharmaceutical compositions including a compound of Formula I, Formula II, Formula IIa, Formula III, Formula IIIa, Formula IV, Formula IVa, or a combination, pharmaceutically acceptable salt, solvate or prodrug thereof, and at least one pharmaceutically acceptable carrier, adjuvant, and/or vehicle, for administration to a subject. The term "excipient" refers to components of a formulation other than the active ingredient. They preferably include a "carrier, adjuvant and/or vehicle". "Carriers" are forms to which substances are incorporated to improve the delivery and the effectiveness of drugs. Drug carriers are used in drug-delivery systems such as the controlled-release technology to prolong in vivo drug actions, decrease drug metabolism, and reduce drug toxicity. Carriers are also used in designs to increase the effectiveness of drug delivery to the target sites of pharmacological actions. An "adjuvant" is a substance added to a drug product formulation that affects the action of the active ingredient in a predictable way. A "vehicle" is an excipient or a substance, preferably without therapeutic action, used as a medium to give bulk for the administration of medicines. Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like, excipients, wetting agents or diluents. Suitable pharmaceutical carriers are described in "*Remington's Pharmaceutical Sciences*" by E. W. Martin.

According to some embodiments, the pharmaceutical composition may further include a therapeutically effective amount of one or more conventional agents used for the treatment and/or prophylaxis of cognitive, neurodegenerative or neurological diseases or conditions. Conventional agents used for the treatment and/or prophylaxis of cognitive, neurodegenerative or neurological diseases or conditions include, but are not limited to, beta secretase inhibitors or modulators including BACE1 protein inhibitors; amyloid beta-protein inhibitors including immunoglobulins, anti-amyloid monoclonal antibodies and vaccines; amyloid beta-protein precursor inhibitors; gamma secretase inhibitors or modulators; muscarinic receptor modulators; acetylcholinesterase inhibitors; butyrilcholinesterase inhibitors; choline acetyltransferase stimulants; HMG-CoA reductase inhibitors; non-steroidal anti-inflammatory agents; cyclo-oxygenase 2 inhibitors; N-methyl-D-aspartate receptor antagonists; vitamin E; nicotinic acetylcholine receptor modulators; serotonin receptor modulators; cannabinoid receptor agonists; CB1 receptor inverse agonists or CB1 receptor antagonists; AMPA receptor modulators; GABA receptor modulators; inhibitors of amyloid aggregation; glycogen synthase kinase beta inhibitors; promoters of alpha secretase activity; phosphodiesterase 9A and 10 inhibitors; type 4 cyclic nucleotide phosphodiesterase inhibitors; estrogen and cholesterol absorption inhibitors; 11-beta hydroxysteroid dehydrogenase type 1 inhibitors; adenosine receptor antagonists; adrenergic receptor modulators; advanced glycosylation end-product receptor antagonists; alpha-synuclein inhibitors; antioxidants; free radical scavengers; apolipoprotein A stimulants; apolipoprotein E agonists;

apoptosis inhibitors; calcium channel modulators; sodium channel modulators; calpain inhibitors; cathepsin B inhibitors; cell-replacements including stem-cell-therapies; glial cell line-derived neurotrophic factor agonists; nerve growth factor stimulants; chelating agents; complement factor D inhibitors; cyclic AMP response element-binding protein stimulants; D amino acid oxidase inhibitors; dopamine receptor agonists and dopamine uptake inhibitors; endopeptidase inhibitors; fibroblast growth factor stimulants; G protein-coupled receptor antagonists; gene expression stimulants; glucose stimulants; metabotropic glutamate receptor modulators; histamine H3 receptor antagonists or inverse agonists; histone deacetylase inhibitors; mitochondrial-permeability-transition pore-modulators; monoamine oxidase B inhibitors; neuropeptide stimulants; neurotransmitter modulators; plasminogen activator inhibitor-1 inhibitors; protein kinase C stimulants; rho-associated kinase inhibitors; ribonucleotide reductase inhibitors; signal transduction pathway inhibitors; superoxide dismutase stimulants; tau protein modulators; tubulin polymerization promoters; toll-like receptor agonists; transglutaminase inhibitors and Wnt protein modulators.

According some embodiments, the pharmaceutical composition may further include a therapeutically effective amount of one or more conventional agents used for the treatment and/or prophylaxis of diabetes, inflammatory and autoimmune diseases, cardiovascular disorders, and pathologies selected from metabolic syndrome X, hair loss, severe acute respiratory syndrome coronavirus, cocaine addiction, bone loss and glaucoma.

Examples of pharmaceutical compositions include any solid (tablets, pills, capsules, granules etc.), or liquid (solutions, suspensions or emulsions) composition for oral, topical or parenteral administration, among others.

Pharmaceutical dosage forms include but are not limited to parenteral preparations (such as injections, powders for injections, implants, etc.), liquid preparations for oral use (such us syrups, solutions, suspensions, emulsions, powders and granules for suspension and for solution, oral drops, etc.), oromucosal preparations (such as lozenges, sublingual and buccal tablets, oromucosal drops and sprays, etc.) solid preparations for oral use (oral powders, effervescent powders, tablets—uncoated, coated, effervescent, soluble, dispersible, orodispersible, modified release, gastro-resistant-, oral lyophilizates, capsules—hard, soft, modified release, gastro-resistant-, granules—coated, effervescent, modified release, gastro-resistant-), transdermal patches, powders for inhalation, nasal preparations and rectal preparations.

In certain embodiments, the pharmaceutical compositions are in oral form because of the convenience for the subject and the chronic character of many of the diseases to be treated. Said oral pharmaceutical compositions may contain conventional excipients known in the art including binders, such as maize starch, pregelatinized maize starch, povidone, gelatine, etc.; diluents or fillers, such as microcrystalline cellulose, lactose, sodium phosphate, calcium phosphate dibasic dihydrate, calcium phosphate dibasic anhydrous, etc.; disintegrants, such as sodium croscarmeilose, sodium starch glycolate, cross-linked povidone, gums, etc.; glidants, such as talc or colloidal silica; lubricants, such as magnesium stearate, stearic acid, sodium stearyl fumarate, etc.; film-formers, such as hydroxypropylcellulose, Hypromellose, hydroxy-propylmethylcellulose, etc.; opacifiers, such as titanium dioxide; coloring agents, such as sunset yellow, iron oxides, indigo carmine, erythrosine, etc.; plasticizers, such as polyethylene glycol, triacetin, etc.; acidifying agents, such as citric acid; buffering agents, such as citric acid and sodium citrate; sweetening agents, such as sucralose, aspartame, acesulfame, sodium saccharine, etc.; flavoring agents, such as strawberry flavor, lemon flavor, cola flavor, orange flavor, etc.; thickening or stabilizers such as modified celluloses (hydroxipropylcellulose, carboxymethylcellulose sodium), povidones, gums, etc.; antimicrobial and solvent agents, such as ethanol, propyleneglycol, etc.; antimicrobial preservatives, such as sodium benzoate, potassium sorbate; coloring agents, such as tartrazine, curcumin, quinoline yellow, sunset yellow, etc.; and lubricants, such as talc, magnesium stearate, stearic acid, sodium stearyl fumarate, polyethylenglycols, etc.

Solid oral compositions may be prepared by conventional methods of blending, filling or tableting. Repeated blending operations may be used to distribute the active agent throughout those compositions employing large quantities of fillers. Such operations are conventional in the art. Tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, e.g., antimicrobial preservatives, such as methylparaben, prophylparaben, etc.; antioxidants, such as sodium metabisulfite, propyl gallate, etc.; stabilizing and suspending agents, such as soluble or swellable modified celluloses, e.g., carboxymethylcellulose sodium; tonicity agents, such as sodium chloride; and solubilizers, such as propyleneglycol or polyetheneglycols.

The following non-limiting examples are provided to further illustrate the present invention.

Example 1: Therapeutic Effects of Isoorientin on Alzheimer's Disease

This example describes the therapeutic effects of isoorientin 1 on Alzheimer's based on three pathological indicators, i.e., senile plaques, hyperphosphorylated tau protein, and neuroinflammation.

Materials and Methods

Wild-Type and Transgenic Alzheimer Mice.

The backgrounds of all mice (APP/PS1 dual transgenic mice and wild-type mice with littermates) were C57/B6. Transgenic mice were randomly divided into three groups (n=20 for each group), and wild-type mice were used as controls (n=20). The control group and one group of transgenic mice (model group) were given sterilized ultrapure water, and the other two groups of transgenic mice received low- and high-dose Isoorientin (20 and 50 mg/kg, respectively) via intragastric administration for 60 days. Throughout the study-period, animals were housed in a controlled environment (temperature, 22° C.; humidity, 50-60%, 12-hour light/12-hour dark schedules), with free access to rodent chow and water. After a Morris water maze test, mice were perfused with cold phosphate-buffered saline (PBS), brain tissues were dissected and kept frozen at −80° C. until further analysis. Brain tissues were fixed in 4% paraformaldehyde for immunohistochemical analysis.

Chemicals and Preparation.

Isoorientin was dissolved in sterilized, ultrapure water, sonicated for 20 minutes at a concentration of 5 mg/ml and 2.5 mg/ml, and stored at 4° C. Isoorientin was administered by oral gavage. The required amount of solution was returned to room temperature before intragastric administration. The animals were treated with 5 mg/kg and 2.5 mg/kg body weight (0.125 mg/25-gram mouse and 0.0625 mg/25-gram mouse, respectively).

Morris Water Maze Test.

The maze was composed of a circular pool (120 cm in diameter) filled with water (22±2° C.) to a height of 30 cm. The objective for the mouse was to find the platform (8 cm in diameter), which was placed 1 cm below the water surface in the middle of one quadrant of the pool, 20 cm from the wall. Mice were given day of adaptive training followed by trials on six consecutive days. Each trial started by gently placing the mouse into the water with its head toward the pool wall of any of the three quadrants without the platform. If an animal found the platform within 60 seconds, it was left on the platform for 20 seconds. If an animal did not find the platform, they were gently guided to the platform by the experimenter and left there for also 20 seconds. On the last day of Morris water maze test, the platform was removed and the number of times that the mice crossed the location of the original platform was quantified. Between trials, all mice were placed back in their home cages using a spoon-net to avoid direct contact with the experimenter. All trials were tracked automatically by a digital tracking system (Feidi Biological Technology) assessing path length, swimming speed, and latency to escape from the water.

Quantification of Anti-Aβ Immunoglobulins by Enzyme-Linked Immunosorbent Assay.

Blood was collected from mice. After incubating blood at 4° C. for 30 minutes, the blood was centrifuged at 10,000 g for 10 minutes, and serum was subsequently collected and stored at −80° C. until it was used. The anti-Aβ immunoglobulin (IgG) was measured using an enzyme-linked immunosorbent assay (ELISA) kit according to the manufacturer's protocol (see also, Song, et al. (2017) *PLoS One* 12(1):e0169509). Briefly, microtiter immune plates were coated with peptide Aβ 1-42 (5 µg/ml) in 50 mM carbonate buffer pH 9.6 overnight at 4° C. and rinsed four times with washing buffer (PBS containing 0.05% TWEEN®-20 (polysorbate 20)). Microtiter immune plate were treated with blocking buffer (5.0% goat serum, 1% BSA and 0.05% TWEEN®-20 (polysorbate 20) in PBS) for 1 hour at room temperature (25~27° C.). The serum samples were diluted with PBS and added to each well in the microtiter immune plate. After incubation for 2 hours at room temperature with gentle shaking, the plates were washed six times with the washing buffer and incubated for 1 hour with an appropriate horseradish peroxidase (HRP)-conjugated detection antibody. The detection antibodies were diluted in the blocking buffer at 1:2000 for anti-mouse IgG. After washing, plates were incubated with chromogenic substrate (3,3',5,5-tetramethylbenzidine, TMB) for 15 minutes and the reaction was stopped with the addition of 1N $H_2SO_4$. The optical densities at 450 nm were analyzed using a microreader (TECAN, Switzerland) and linear regression was confirmed by ab126468, polyclonal anti-amyloid fibril antibody, as positive internal control. Thus, the concentrations (µg/ml) of the serum titers presented reflect the concentrations of ab126468 antibody. Comparison of treatment groups was performed by ANOVA and two-tailed Student's t-test. P<0.05 indicates statistically significant.

Quantification of Cytokines.

T-cell-specific cytokines (Interferon-γ (IFN-γ), interleukin (IL)-2, IL-4, and IL-10) in mouse serum were also measured. Mouse Th17 Magnetic Bead Panel 96-Well Plate Assay was purchased from Millipore. The assay was performed in a 96-well plate and all reagents were prepared according to the Millipore instructions. Briefly, 200 µL of Wash Buffer was added into each well to pre-wet plate, Wash Buffer was decanted thoroughly and the plate was mixed on a plate shaker for 10 minutes at room temperature (25-27° C.). In accordance with the instructions of the kit, the appropriate reagents were added to the wells and the plate was sealed and incubated overnight at 4° C. in the dark. Plates were put on the magnetic support and each well was washed twice with 200 µl of wash buffer via a plate shaker at 450 rpm for 2 minutes at room temperature. After adding 5 µl of detection antibody to each well, the plate was sealed and incubated with agitation on a plate shaker for 1 hour at room temperature. Streptavidin-Phycoerythrin solution (25 µl) was added to each well and the plate was incubated in the dark for 30 minutes at room temperature with agitation. The plate was subsequently washed twice, 150 µl of Sheath Fluid was added to all wells, and the plate was mixed for 5 minutes to resuspend the beads. Binding was assessed using a LUMINEX-200 instrument and xPONENT software.

Quantification of Cytokines by ELISA.

Serum samples were analyzed for IL4 and TNFα using a Mouse IL4 ELISA Kit and a Mouse TNFα ELISA Kit, respectively, according to the manufacturer's instructions. Comparison of treatment groups was performed by ANOVA and two-tailed Student's t-test. P<0.05 indicates statistically significant.

Quantification of Aβ42 by ELISA.

For quantitation purposes, a highly specific and sensitive mouse Aβ42 ELISA kit was used (Invitrogen Corporation, Carlsbad, Calif.). Brain tissue protein was extracted by homogenizing about 100 mg brain tissue with an 8-fold mass quantity of cold 5 M guanidine-HCl and 50 mM Tris (pH 8.0), and incubating the homogenate at room temperature for 3.5 hours. The sample was subsequently diluted ten-fold with cold PBS containing 1× Halt™ Protease and Phosphatase Inhibitor followed by centrifugation at 16,000 g for 20 minutes at 4° C. The supernatant was aspirated and frozen at −80° C.

Soluble and insoluble brain samples including cortex and hippocampus were analyzed for Aβ levels using the mouse Aβ42 ELISA kit, according to the manufacturer's instructions. The supernatant was diluted with a standard dilution buffer at 1:4000 (Aβ42, transgenic mice groups) or 1:20 (Aβ42, wild-type mice control group). The obtained values were corrected for the wet weight of each brain sample and expressed as µg/mg brain.

Thioflavin-S Staining.

All mice were deeply anaesthetized with an overdose of sodium pentobarbital (intraperitoneally) and transcardially perfused with 0.1 M PBS, followed by 4% paraformaldehyde (diluted in 0.1 M PBS at pH 7.4) to fix the brains. The brains were then rapidly removed, suspended in 4% paraformaldehyde for 24 hours at 4° C., then transferred to graded sucrose solutions (10, 20, and 30%) dissolved in 0.1 M PBS, and stored at 4° C., until the brain was completely immersed in the solution. The brain tissue was then embedded in an OCT agent and placed at −80° C. for storage until use. The OCT block was sectioned with a cryostat (Lecia) at 10 µm thickness. The Thio-S staining procedure was according to known methods (Maiti, et al. (2016) *Histochem. Cell Biol.* 146(5):609-625). Briefly, Thio-S solution at 0.1% (w/v) was prepared by dissolving 0.1 gram of Thioflavin-S (Sigma-Aldrich) in 50% ethanol (v/v). The tissue sections were washed three times with PBS for five minutes each time. The sections were incubated with 0.1% Thio-S for 10 minutes, dipping them three times in 50% ethanol (v/v) for 10 minutes each time, and finally washing once in PBS, before being mounted, as described above. The sections were visualized using a fluorescence microscope (Leica, Germany), with excitation/emission filters (480/550 nm).

Immunofluorescence Labeling (Aβ+IBA1).

Double-labelling procedures were performed to determine the relationship between Iba1-positive and Aβ-positive plaques. Prior to immunofluorescence staining, 10 µm thick brain tissue frozen sections were washed with TBS pH 7.4, then subjected to heat-mediated antigen retrieval for 12 minutes in 10 mM sodium citrate buffer (pH 6.0) containing 0.05% TWEEN®-20 (polysorbate 20). Sections were then blocked with 5% BSA in 0.01% TRITON X-100 in TBS (TBST) for 1 hour at room temperature. Coverslips were incubated with a solution of rabbit anti-Aβ antibody (1:150; Abcam) or goat anti-Iba1 (1:200; Santa Cruz) overnight, washed three times with PBS, and incubated with a solution of ALEXA® 594 (fluorescent dye) donkey anti-goat (1:500; Abcam) in 5% BSA in TBST for minutes at room temperature in the dark. After three washes with TBS, samples were incubated with ALEXA®488 (fluorescent dye) goat anti-rabbit (1:250; Invitrogen) for minutes at room temperature in the dark. Finally, coverslips were washed three times with TBS and then counterstained with DAPI, following a series of washings, samples were mounted with 90% glycerin. Slides were stored in the dark at 4° C. until imaging. Representative images were obtained by fluorescence microscope (Leica).

Results and Discussion

Isoorientin Reduces Spatial Learning and Memory Deficits in Transgenic Alzheimer Mice.

Figure 2:
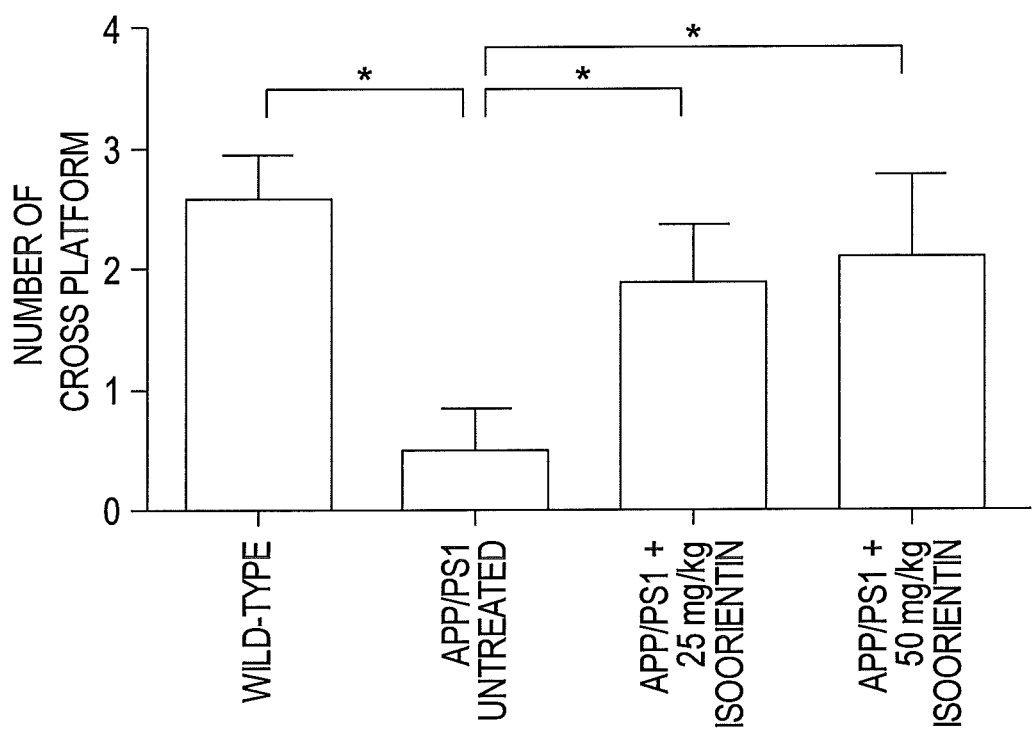
FIG. 2 shows the number of target platform crossings recorded in the Morris water maze trial. $*P<0.05$. n=10.

A Morris water navigation test was performed to evaluate spatial memory in mice. Mice were trained daily for six days and the time taken to reach a hidden platform (escape latency) was recorded. As presented in FIG. 1, APP/PS1 mice exhibited a significantly longer escape latency, compared with wild-type mice (P<0.05), and all doses of isoorientin groups significantly reduced the escape latency in APP/PS1 mice, relative to untreated APP/PS1 mice (P<0.05). In addition, the significantly lower platform cross frequencies in APP/PS1 mice, relative to wild-type mice (P<0.05), were significantly increased by all doses of isoorientin groups, relative to untreated APP/PS1 mice (P<0.05; FIG. 2). These data indicate that oral administration of isoorientin (25-mg/kg) caused significant alleviation of cognitive deficit in APP/PS1 mice.

Isoorientin Improves the Immune Response to Aβ42 in the Body.

Figure 3:
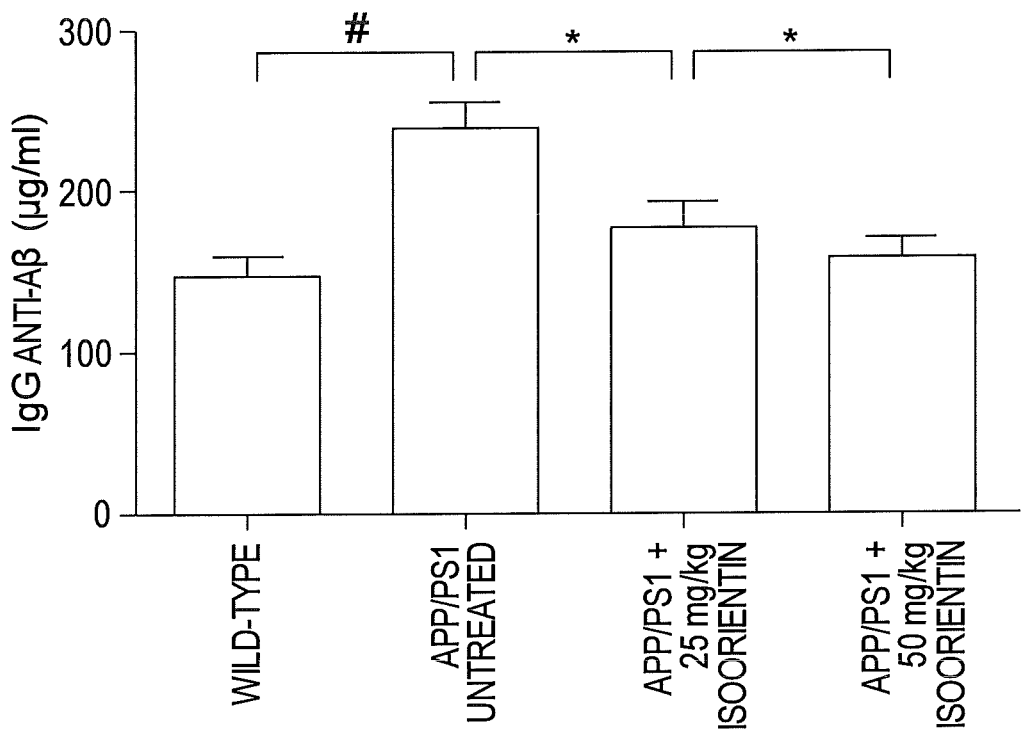
FIG. 3 shows that the secretion of IgG anti-Aβ42 in serum of APP/PS1 mice is reduced by isoorientin treatment. IgG in the serum was analyzed by ELISA. IgG is expressed as µg/ml serum. IgG was significantly increased in untreated APP/PS1 animals compared to the age-matched wild-type littermates control animals. Isoorientin treatment in turn prevented this effect. (one-way ANOVA with Tukey's multiple comparison post-hoc test). Data represent mean±SEM; n=10; # $p<0.01$, $*p<0.01$ as indicated.

To determine whether isoorientin induces a humoral immune response, IgG antibody production was measured as a representative indicator of the immune response. After completion of the 60-day intragastric administration, the mice were sacrificed and blood samples were collected and centrifuged. The IgG levels were determined via ELISA to identify the immune response against the Aβ1-42 peptide using an HRP-conjugated secondary antibody specific for mouse IgG. As shown in FIG. 3, compared with the control group, the IgG content of the model group was higher, P<0.01. Interestingly, the immune response of IgG in the sera decreased in the in the isoorientin-fed mice compared with the model group. These results indicated that after treatment with isoorientin, the immune response in vivo shifted to a steady state.

Isoorientin Significantly Reduces Aβ42 Levels in the Brain.

Figure 4:
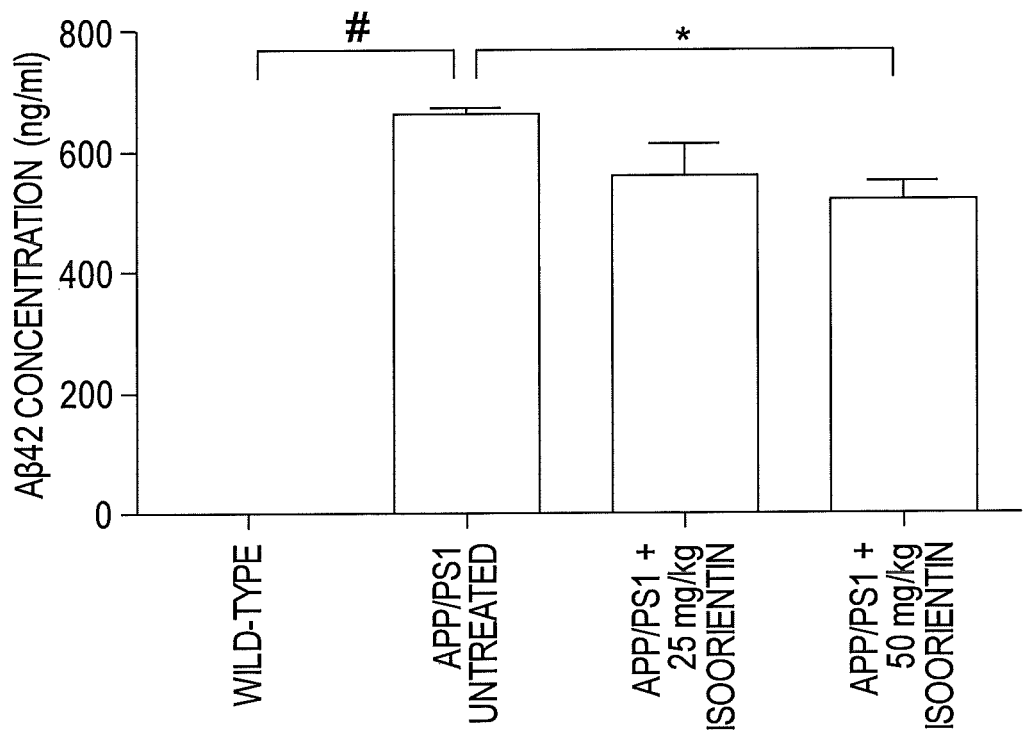
FIG. 4 shows that oral administration of isoorientin for 60 days decreases Aβ42 in APP/PS1 transgenic mouse brain. A significant decrease in brain (cortex+hippocampus) Aβ42 was observed in high dose group at 50 mg/kg (# $p<0.01$, model group vs. control group; $*p<0.05$, high-dose group vs. model group). n=6.
Figure 5:
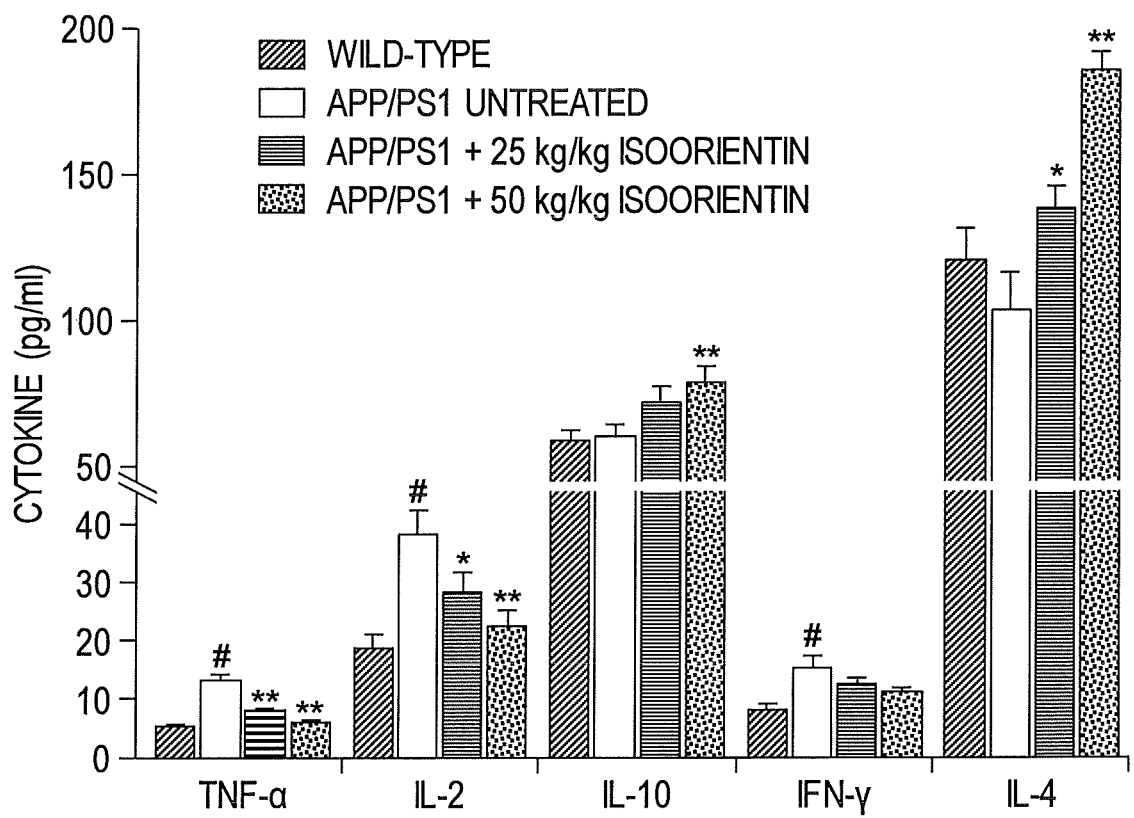
FIG. 5 shows a comparison of cytokine profiles in APP/PS1 transgenic mouse untreated or treated with isoorientin. The T cell-mediated inflammatory responses, including Th1 (TNFα, IL-2 and IFN-γ) and Th2 (IL-4 and IL-10) cytokines, were measured in mouse serum using ELISA. Differences between the isoorientin-treated (APP/PS1+25 mg/kg; APP/PS1+50 mg/kg) and vehicle (sterilized water)-treated control (wild-type; APP/PS1) mice are shown. The values were presented as the means±S.E.M (n=6 mice per group). # $p<0.01$. model group vs. control group; $P<0.05$, $p<0.01$ isoorientin-treated groups vs. model group.

To determine the effect of isoorientin on Aβ load, the total amounts of Aβ42 in the hippocampus and cortex areas of mice brains were analyzed using Aβ42 ELISA kits. As shown in FIG. 4, Aβ42 levels were significantly higher in the model group than in the control group (p<0.01). Interestingly, Aβ42 loads were significantly lower in the high-dose group compared to the model group (p<0.05). At the same time, there was no statistically significant difference between the low-dose group and the model group. Based on the reduction in Aβ42 levels in the APP/PS1 transgenic brains after 2 months of treatment with isoorientin, it was concluded that the burden of cerebral amyloid load (i.e., hippocampus and cortex) could be altered using isoorientin.

Isoorientin Reduces the Levels of Pro-Inflammatory Factors in the Serum of Transgenic Mice and Improves the Levels of Anti-Inflammatory Factors.

To test whether isoorientin can affect the level of inflammation in the mouse body and exert neuroprotective effects, the levels of inflammatory factors such as IL-2, IFNγ, IL-10, TNFα and IL-4 were determined. Overall, the levels of various pro-inflammatory factors (including TNFα, IFNγ, and IL-2) in serum were slightly lower than those in the model group, and there was no statistical difference in the decrease in IFNγ. Meanwhile, after treatment with isoorientin, anti-inflammatory factor levels (including IL-4 and IL-10) in transgenic mouse serum were significantly elevated with significant statistical differences. Thus, these results indicate that isoorientin can regulate the of inflammation in the mouse body and induce the secretion of anti-inflammatory factors.

Isoorientin Reduces Senile Plaques in Brain Tissue.

Given that another key neuropathologic feature associated with Alzheimer's disease is an accumulation of amyloid plaques in the brain, plaques in brains of mice were visualized by thioflavin-S staining. It was observed that plaques were almost exclusively found only in the slices from transgenic APP/PS1 mice compared to wild-type mice. However, thioflavin-S-positive plaques were reduced in the isoorientin-treated groups, and the trend of decreasing the number of positive plaques was more pronounced with increasing dose of isoorientin (25 mg/kg and 50 mg/kg).

Isoorientin Reduces Aβ Deposition, and Activation and Aggregation of Microglia Caused by Aβ Deposition.

Cells positive for Iba1 staining in Alzheimer's disease tissue are found in close proximity to Aβ-positive senile plaques. Closer magnification shows that Iba1-positive cells found within the coronal region of the Aβ plaques are microglia based on cellular morphology and prior research demonstrating Iba1 accumulation predominantly in Alzheimer's disease microglia. Immunofluorescence double staining showed that the number of core dense Aβ plaques in the cortex and hippocampus of the model group was the highest in all groups, and the aggregation of Iba1-positive cells around the plaques was more obvious. In the transgenic mice groups, Aβ plaques were reduced after isoorientin treatment, and the typical activated aggregated Iba1-positive cells around the plaques were also reduced.

Having demonstrated the therapeutic effects of isoorientin 1 on Alzheimer's based on three pathological indicators, i.e., senile plaques, hyperphosphorylated tau protein, and neuroinflammation, analogs of isoorientin, i.e., compounds of Formulae I, II, IIa, III, IIIa, IV and IVa, are also expected to reduce spatial learning and memory associated with Alzheimer's disease, reduce Aβ42 levels in the brain, reduce the levels of pro-inflammatory factors, reduce senile plaques, and reduce Aβ deposition, and activation and aggregation of microglia caused by Aβ deposition.

Example 2: Selective, Substrate-Competitive and Passive Membrane Permeable GSK-3β Inhibitors Materials and Methods Chemicals and Reagents.

All solvents and reagents were from commercial sources and were used without further purification. Natural flavones (isoorientin 1, isovitexin 2, orientin 3, and luteolin 4), staurosporine, TDZD-8, theophylline, atenolol, desipramine, TMSCHN$_2$, [TEMPO]$^+$[BF$_4$]$^-$, HCTU, organic amines, and protease inhibitor cocktail were from Sigma-Aldrich (Saint Louis, Mo.).

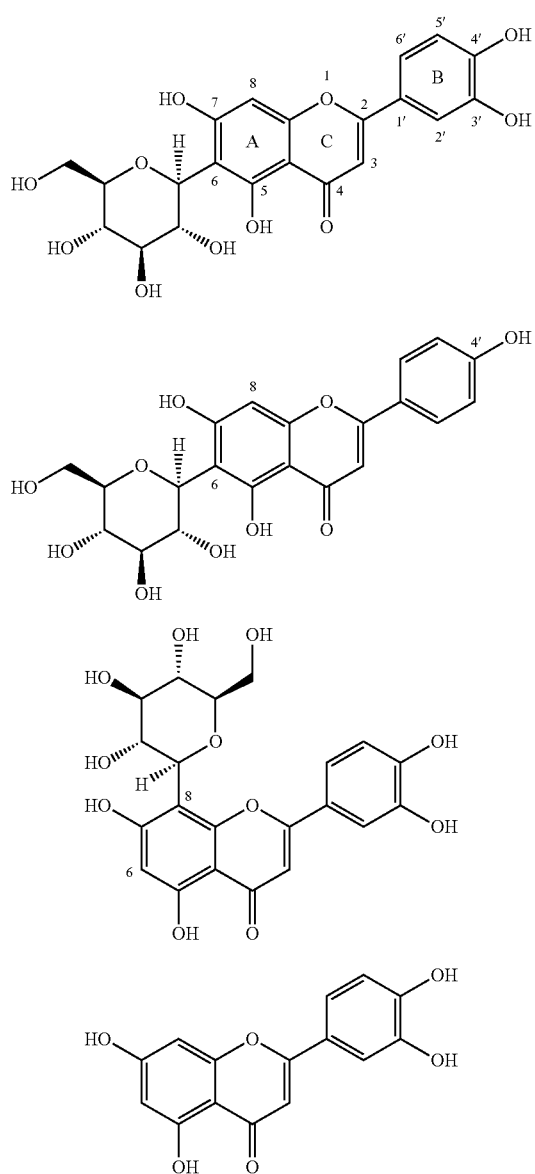

β-Amyloid fragment peptide 1-42 (Aβ$_{42}$) was from AnaSpec (Fremont, Calif.). Kinase Selectivity Profiling Assay Kit, ADP-Glo Kinase Assay Kit, and CELLTITER 96® AQueous One Solution Cell Proliferation MTX Assay Kit were from Promega (Madison, Wis.). Human Tau pS396 ELISA Kit and Cell Extraction Buffer were from Invitrogen (Camarillo, Calif.). Pre-coated PAMPA plate system was from Corning (Tewksbury, Mass.).

General Experimental Procedures.

High-resolution mass spectrometric data were obtained on a Bruker maXis Impact nanoLC-QTOF-MS spectrometer in ESI positive mode. Accurate masses of all analytes were obtained from the pseudo-molecule [M+H]$^+$ and were within 5 ppm mass error. $^1$H, $^{13}$C and $^2$D NMR data were recorded with a Varian Unity Inova 500 MHz spectrometer. NMR spectra were referenced to the appropriate residual solvent signal ($\delta_H$ 2.50, $\delta_c$ 39.5 for DMSO-d$_6$) with chemical shifts reported in δ units (ppm). Resonance multiplicities are denoted s, d, t, q, m, and br for singlet, doublet, triplet, quartet, multiplet, and broad, respectively.

All reactions were monitored by LC-MS (Bruker nanoLC-QTOF-MS). Compounds in crude reaction mixtures were separated by flash column chromatography on HyperSep™ C18 (40-63 μm), and purified by semi-preparative reverse phase Agilent HPLC with a diode array detector (Waters XSELECT CSH Phenyl-Hexyl column, 150×10 mm, 5 μm, a linear gradient over 30 minutes from 10 to 50% aqueous acetonitrile containing 0.1% formic acid, flow rate 2.5 mL/min).

The purity of each compound was determined by analytical reverse phase Agilent HPLC with a diode array detector (Waters XSELECT CSH Fluoro-Phenyl column, 150×4.6 mm, 3.5 μm, isocratic elution with 35% aqueous acetonitrile containing 0.1% formic acid, detection at 210, 254, and 340 nm, flow rate of 0.8 mL/min). All the tested compounds were over 95% purity by HPLC-UV at 210 nm.

Luminescent measurement was performed on an Agilent Cary Eclipse fluorescence spectrophotometer. Optical absorbance was measured on a Multiskan GO Microplate spectrophotometer. Microscopic images were observed under a Nikon Diaphot inverted tissue culture microscope with Optronics MicroFire microscope camera.

Preparation of Compound 5.

To a stirred solution of (45 mg, 0.1 mmol) in a mixture of toluene (6 mL) and methanol (4 mL) was added TMSCHN$_2$ (2 M in hexane, 0.5 mL, 1 mmol). The reaction solution was stirred at room temperature for 8 hours and the solvent was evaporated. The residue was purified by RP-HPLC (Waters XSELECT CSH Fluoro-Phenyl column, 150×4.6 mm, 3.5 μm, isocratic elution with 35% aqueous acetonitrile containing 0.1% formic acid, detection at 210, 254, and 340 nm, flow rate of 0.8 mL/minute) to afford 5.

2-(3,4-Dimethoxyphenyl)-5,7-dimethoxy-6-((2S,3R,4R,5S,6R)-3,4,5-trihydroxy-6-(hydroxymethyl) tetrahydro-2H-pyran-2-yl)-4H-chromen-4-one (5)

Light yellow solid (80% yield). $^1$H NMR (DMSO-d$_6$) δ 7.65 (dd, J=8.6, 2.2 Hz, 1H), 7.54 (d, J=2.2 Hz, 1H), 7.12 (d, J=8.6 Hz, 1H), 7.09 (br s, 1H), 6.72 (br s, 1H), 4.65 (br d, J=9.7 Hz, 1H), 4.05 (dd, J=12.7, 9.2 Hz, 1H), 3.89 (s, 3H), 3.86 (s, 3H), 3.81 (s, 3H), 3.77 (s, 3H), 3.72 (dd, J=12.6, 12.5 Hz, 1H), 3.34-3.28 (m, 1H), 3.27-3.12 (m, 3H). $^{13}$C NMR (DMSO-d$_6$) δ 175.5, 163.4, 160.2, 158.9, 158.5, 151.8, 149.1, 123.2, 119.7, 111.9, 111.3, 109.4, 107.1, 107.0, 97.0, 82.0, 79.2, 73.1, 71.3, 70.9, 62.6, 62.0, 61.8, 56.4, 55.8. HRESI-TOFMS m/z [M+H]$^+$ 505.1710 (calcd for C$_{25}$H$_{29}$O$_{11}$$^+$, 505.1704, −1.1 ppm error). HPLC purity: 97.1% (210 nm).

Preparation of Compound 6.

To a stirred solution of (45 mg, 0.09 mmol) in a mixture of dichloromethane (6 mL) and pyridine (3 mL) was added [TEMPO]$^+$[BF$_4$]$^-$ (oxoammonium salt, 60 mg, 0.2 mmol).

The reaction mixture was stirred at room temperature for 5 hours. The reaction was quenched by adding drops of methanol and then evaporated to dryness. The residue was reconstituted in 5% MeOH/H$_2$O and then eluted on a HyperSep™ C18 column using the same solvents to remove the red-orange nitroxide. Elution was continued with 90% MeOH/H$_2$O and the eluate was collected as the crude product, which was further purified by RP-HPLC (Waters XSELECT CSH Fluoro-Phenyl column, 150×4.6 mm, 3.5 μm, isocratic elution with 35% aqueous acetonitrile containing 0.1% formic acid, detection at 210, 254, and 340 nm, flow rate of 0.8 mL/minute) to afford 6.

(2S,3S,4R,5R,6S)-6-(2-(3,4-Dimethoxyphenyl)-5,7-dimethoxy-4-oxo-4H-chromen-6-yl)-3,4,5-trihydroxytetrahydro-2H-pyran-2-carboxylic acid (6)

Light yellow solid (95% yield). $^1$H NMR (DMSO-d$_6$) δ 7.65 (dd, J 8.5, 2.0 Hz, 1H), 7.54 (d, J=2.0 Hz, 1H), 7.12 (d, J=8.5 Hz, 1H), 7.09 (br s, 1H), 6.76 (d, J=6.6 Hz, 1H), 4.60 (d, J=10.1 Hz, 1H), 4.02 (m, 1H), 3.89 (s, 3H), 3.85 (s, 3H), 3.82 (s, 3H), 3.75 (s, 3H), 3.30-3.16 (m, 3H). $^{13}$C NMR (DMSO-d$_6$) δ 175.5, 173.0, 162.2, 160.4, 158.9, 158.5, 151.9, 149.2, 123.2, 119.7, 111.9, 111.4, 109.4, 107.1, 107.0, 97.1, 79.0, 78.5, 74.1, 72.5, 71.3, 63.5, 62.6, 56.6, 56.1. HRESI-TOFMS m/z [M+H]$^+$ 519.1502 (calcd for C$_{25}$H$_{27}$O$_{12}$$^+$, 519.1497, −0.9 ppm error). HPLC purity: 97.8% (210 nm).

Preparation of Compound 7.

To a stirred solution of (1 mg, 2 μmol) in a mixture of toluene (1.5 mL) and methanol (1 mL) was added TMSCHN$_2$ (2 M in hexane, 2 μL, 4 μmol). The reaction solution was stirred at room temperature for 1 hour and the solvent was evaporated. The residue was purified by RP-HPLC (Waters XSELECT CSH Fluoro-Phenyl column, 150×4.6 mm, 3.5 μm, isocratic elution with 35% aqueous acetonitrile containing 0.1% formic acid, detection at 210, 254, and 340 nm, flow rate of 0.8 mL/minute) to afford 7.

Methyl (2S,3S,4R,5R,6S)-6-(2-(3,4-dimethoxyphenyl)-5,7-dimethoxy-4-oxo-4H-chromen-6-yl)-3,4,5-trihydroxytetrahydro-2H-pyran-2-carboxylate (7)

Light yellow solid (87% yield). $^1$H NMR (DMSO-d$_6$) δ 7.69 (dd, J=8.5, 2.1 Hz, 1H), 7.56 (d, J=2.1 Hz, 1H), 7.15 (br s, 1H), 7.12 (d, J=8.5 Hz, 1H), 6.80 (d, J=5.5 Hz, 1H), 4.57 (d, J=9.6 Hz, 1H), 4.00 (m, 1H), 3.89 (s, 3H), 3.85 (s, 3H), 3.80 (s, 3H), 3.73 (s, 3H), 3.63 (s, 3H), 3.29-3.13 (m, 3H). $^{13}$C NMR (DMSO-d$_6$) δ 175.6, 172.9, 162.1, 160.1, 159.0, 158.4, 151.8, 149.1, 123.2, 119.7, 111.9, 111.4, 109.4, 107.1, 107.0, 97.0, 79.0, 78.5, 74.1, 72.5, 71.3, 63.4, 62.6, 56.6, 56.0, 51.8. HRESI-TOFMS m/z [M+H]$^+$ 533.1656 (calcd for C$_{26}$H$_{29}$O$_{12}$$^+$, 533.1654, −0.5 ppm error). HPLC purity: 97.1% (210 nm).

Preparation of Compounds 8-31.

To a stirred solution of 6 (5 mg, 9.7 μmol) in a mixture of dimethylformamide (1 mL) and DIPEA (0.5 mL) was added HCTU (10 mg, 24 μmol) and then stirred for 10 minutes at room temperature. To this solution was added corresponding organic amines (each 50 μmol) and stirred at room temperature for 5 hours.

The reaction was quenched by adding 1 N HCl followed by evaporation of solvents to dryness. The residue was purified by RP-HPLC (Waters XSELECT CSH Fluoro-Phenyl column, 150×4.6 mm, 3.5 μm, isocratic elution with 35% aqueous acetonitrile containing 0.1% formic acid, detection at 210, 254, and 340 nm, flow rate of 0.8 mL/min) to afford the final products.

(2S,3S,4R,5R,6S)-6-(2-(3,4-Dimethoxyphenyl)-5,7-dimethoxy-4-oxo-4H-chromen-6-yl)-3,4,5-trihydroxy-N-propyltetrahydro-2H-pyran-2-carboxamide (8)

Light yellow solid (90% yield). $^1$H NMR (DMSO-d$_6$) δ 7.67 (d, J=8.7 Hz, 1H), 7.53 (d, J=2.2 Hz, 1H), 7.13 (s, 1H), 7.12 (d, J=8.7 Hz, 1H), 6.76 (d, J=5.9 Hz, 1H), 4.67 (br d, J=10.1 Hz, 1H), 4.06 (q, J=10.3 Hz, 1H), 3.87 (s, 3H), 3.83 (s, 3H), 3.77 (s, 3H), 3.71 (s, 3H), 3.60 (m, 1H), 3.50 (m, 1H), 3.23 (m, 1H), 2.99 (m, 2H), 1.36 (m, 2H), 0.78 (td, J=7.4, 2.2 Hz, 3H). $^{13}$C NMR (DMSO-d$_6$) δ 175.7, 168.7, 163.4, 160.5, 160.2, 158.4, 151.6, 149.3, 123.1, 120.4, 112.2, 111.9, 109.6, 107.2, 107.0, 96.8, 80.6, 79.0, 74.4, 71.6, 69.6, 63.9, 63.1, 56.7, 56.1, 40.8, 22.6, 11.5. HRESI-TOFMS m/z [M+H]$^+$ 560.2135 (calcd for C$_{28}$H$_{34}$NO$_{11}$$^+$, 560.2126, −1.6 ppm error). HPLC purity: 98.6% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-isopropyltetrahydro-2H-pyran-2-carboxamide (9)

Light yellow solid (90% yield). $^1$H NMR (DMSO-d$_6$) δ 7.67 (d, J=8.1 Hz, 1H), 7.55 (d, J=2.2 Hz, 1H), 7.14 (br s, 1H), 7.12 (d, J=9.7 Hz, 1H), 6.77 (d, J=5.1 Hz, 1H), 4.67 (d, J=9.7 Hz, 1H), 4.05 (m, 1H), 3.92 (s, 3H), 3.89 (s, 3H), 3.85 (s, 3H), 3.83 (m, 1H), 3.81 (s, 3H), 3.59 (m, 1H), 3.57 (m, 1H), 3.23 (m, 1H), 1.04 (d, J=6.4 Hz, 3H), 1.01 (d, J=6.8 Hz, 3H). $^{13}$C NMR (DMSO-d$_6$) δ 175.5, 168.7, 163.3, 161.7, 160.1, 158.7, 152.1, 149.2, 123.1, 119.5, 111.9, 111.3, 109.4, 107.1, 107.0, 97.0, 79.8, 78.5, 73.8, 71.4, 70.3, 63.4, 62.5, 56.6, 55.8, 40.3, 22.2, 22.2. HRESI-TOFMS m/z [M+H]$^+$ 560.2117 (calcd for C$_{28}$H$_{34}$NO$_{11}$$^+$, 560.2126, 1.7 ppm error). HPLC purity: 97.2% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-butyltetrahydro-2H-pyran-2-carboxamide (10)

Light yellow solid (90% yield). $^1$H NMR (DMSO-d$_6$) δ 7.68 (d, J=8.6 Hz, 1H), 7.55 (d, J=2.2 Hz, 1H), 7.14 (s, 1H), 7.12 (d, J=8.6 Hz, 1H), 6.81 (d, J=6.7 Hz, 1H), 4.67 (br d, J=10.2 Hz, 1H), 4.06 (m, 1H), 3.89 (s, 3H), 3.85 (s, 3H), 3.80 (s, 3H), 3.74 (s, 3H), 3.58 (m, 1H), 3.50 (m, 1H), 3.23 (m, 1H), 3.02 (m, 2H), 1.34 (m, 2H), 1.23 (m, 2H), 0.83 (m, 3H). $^{13}$C NMR (DMSO-d$_6$) δ 175.9, 168.8, 163.2, 160.3, 160.2, 158.3, 151.8, 149.1, 123.3, 119.7, 111.7, 111.5, 109.2, 107.2, 106.9, 96.5, 80.1, 78.8, 74.0, 71.5, 70.3, 63.8, 62.9, 56.7, 56.1, 38.2, 31.2, 19.6, 13.8. HRESI-TOFMS m/z [M+H]$^+$ 574.2289 (calcd for C$_{29}$H$_{36}$NO$_{11}$$^+$, 574.2283, −1.1 ppm error). HPLC purity: 97.4% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-isobutyltetrahydro-2H-pyran-2-carboxamide (11)

Light yellow solid (88% yield). $^1$H NMR (DMSO-d$_6$) δ 7.62 (d, J 8.8 Hz, 1H), 7.49 (d, J=1.9 Hz, 1H), 7.14 (s, 1H), 7.11 (d, J=8.6 Hz, 1H), 6.81 (d, J=6.9 Hz, 1H), 4.68 (br d, J=10.2 Hz, 1H), 4.07 (m, 1H), 3.89 (s, 3H), 3.84 (s, 3H), 3.80 (s, 3H), 3.75 (s, 3H), 3.62 (m, 1H), 3.49 (m, 1H), 3.24 (m, 1H), 2.87 (t, J=6.4 Hz, 2H), 1.66 (m, 1H), 0.79 (d, J=6.7 Hz, 6H). $^{13}$C NMR (DMSO-d$_6$) δ 176.2, 167.3, 163.5, 160.6, 160.7, 158.8, 153.1, 149.5, 123.7, 120.7, 113.0, 112.7, 112.4, 108.3, 107.4, 97.7, 81.0, 79.9, 75.2, 72.8, 71.5, 64.6, 64.1, 57.8, 56.9, 47.2, 29.4, 21.3, 21.3. HRESI-TOFMS m/z [M+H]$^+$ 574.2292 (calcd for C$_{29}$H$_{36}$NO$_{11}$$^+$, 574.2283, −1.6 ppm error). HPLC purity: 99.1% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-pentyltetrahydro-2H-pyran-2-carboxamide (12)

Light yellow solid (89% yield). $^1$H NMR (500 MHz, DMSO-d$_6$) δ 7.68 (d, J 8.6 Hz, 1H), 7.55 (d, J=2.1 Hz, 1H), 7.14 (s, 1H), 7.12 (d, J=8.6 Hz, 1H), 6.81 (d, J=6.3 Hz, 1H), 4.67 (br d, J=10.2 Hz, 1H), 4.06 (m, 1H), 3.89 (s, 3H), 3.85 (s, 3H), 3.80 (s, 3H), 3.74 (s, 3H), 3.58 (m, 1H), 3.50 (m, 1H), 3.22 (m, 1H), 3.03 (m, 2H), 1.35 (m, 2H), 1.23 (m, 2H), 1.20 (m, 2H), 0.83 (m, 3H). $^{13}$C NMR (DMSO-d$_6$) δ 175.9, 168.9, 163.2, 160.5, 160.3, 158.5, 151.9, 149.2, 123.4, 119.7, 111.8, 111.6, 109.3, 107.0, 106.8, 96.4, 80.1, 78.8, 73.5, 71.6, 70.4, 63.5, 62.7, 56.1, 55.9, 38.4, 28.7, 28.6, 21.9, 14.0. HRESI-TOFMS m/z [M+H]$^+$ 588.2456 (calcd for C$_{30}$H$_{38}$NO$_{11}$$^+$, 588.2439, −2.8 ppm error). HPLC purity: 98.2% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-hexyltetrahydro-2H-pyran-2-carboxamide (13)

Light yellow solid (90% yield). $^1$H NMR (DMSO-d$_6$) δ 7.68 (d, J=8.6 Hz, 1H), 7.55 (d, J=2.3 Hz, 1H), 7.14 (s, 1H), 7.12 (d, J=8.6 Hz, 1H), 6.81 (d, J=5.9 Hz, 1H), 4.66 (br d, J=10.5 Hz, 1H), 4.06 (q, J=8.6 Hz, 1H), 3.89 (s, 3H), 3.84 (s, 3H), 3.80 (s, 3H), 3.74 (s, 3H), 3.60 (m, 1H), 3.50 (m, 1H), 3.23 (m, 1H), 3.01 (m, 2H), 1.40-1.15 (m, 8H), 0.82 (m, 3H). $^{13}$C NMR (DMSO-d$_6$) δ 175.6, 168.8, 163.4, 160.3, 160.2, 158.6, 151.8, 149.1, 123.1, 119.6, 112.1, 111.8, 109.3, 107.1, 107.0, 97.1, 79.9, 78.7, 74.5, 71.5, 69.4, 63.5, 62.7, 56.6, 56.0, 38.5, 31.0, 28.9, 26.1, 22.1, 13.9. HRESI-TOFMS m/z [M+H]$^+$ 602.2572 (calcd for C$_{31}$H$_{40}$NO$_{11}$$^+$, 602.2596, 3.9 ppm error). HPLC purity: 98.5% (210 nm).

(2S,3S,4R,5R,6S)—N-Cyclopropyl-6-(2-(3,4-dimethoxyphenyl)-5,7-dimethoxy-4-oxo-4H-chromen-6-yl)-3,4,5-trihydroxytetrahydro-2H-pyran-2-carboxamide (14)

Light yellow solid (82% yield). $^1$H NMR (DMSO-d$_6$) δ 7.67 (dt, J=8.3, 2.2 Hz, 1H), 7.54 (d, J=2.2 Hz, 1H), 7.16 (s, 1H), 7.12 (d, J=8.3 Hz, 1H), 6.78 (d, J=5.7 Hz, 1H), 4.64 (br d, J=9.7 Hz, 1H), 4.06 (q, J=8.9 Hz, 1H), 3.88 (s, 3H), 3.84 (s, 3H), 3.79 (s, 3H), 3.73 (s, 3H), 3.51 (m, 1H), 3.50 (m, 1H), 3.19 (m, 1H), 2.62 (m, 1H), 0.79 (m, 2H), 0.58 (m, 2H). $^{13}$C NMR (DMSO-d$_6$) δ 175.3, 167.6, 163.4, 161.5, 160.3, 159.6, 152.5, 149.3, 123.4, 119.8, 111.8, 111.5, 109.4, 107.7, 107.0, 97.0, 80.2, 78.9, 74.1, 71.3, 70.3, 63.5, 62.8, 56.1, 55.8, 23.1, 10.8, 10.8. HRESI-TOFMS m/z [M+H]$^+$ 558.1967 (calcd for C$_{28}$H$_{32}$NO$_{11}$$^+$, 558.1970, 0.5 ppm error). HPLC purity: 98.2% (210 nm).

(2S,3S,4R,5R,6S)—N-Cyclobutyl-6-(2-(3,4-dimethoxyphenyl)-5,7-dimethoxy-4-oxo-4H-chromen-6-yl)-3,4,5-trihydroxytetrahydro-2H-pyran-2-carboxamide (15)

Light yellow solid (85% yield). $^1$H NMR (DMSO-d$_6$) δ 7.67 (dt, J=8.6, 2.1 Hz, 1H), 7.54 (d, J=2.1 Hz, 1H), 7.16 (s, 1H), 7.12 (d, J=8.6 Hz, 1H), 6.77 (d, J=7.2 Hz, 1H), 4.66 (br d, J=9.7 Hz, 1H), 4.16 (q, J=7.8 Hz, 1H), 4.05 (td, J=9.3, 5.7 Hz, 1H), 3.88 (s, 3H), 3.84 (s, 3H), 3.78 (s, 3H), 3.74 (s, 3H), 3.54 (m, 1H), 3.51 (m, 1H), 3.21 (m, 1H), 2.09 (m, 2H), 1.86 (m, 2H), 1.58 (m, 2H). $^{13}$C NMR (DMSO-d$_6$) δ 175.5, 167.4, 163.1, 161.4, 160.5, 159.3, 152.2, 149.1, 123.2, 119.6, 111.9, 111.6, 109.1, 107.5, 107.0, 97.1, 80.4, 78.5, 74.2, 71.2, 70.4, 63.3, 62.7, 55.9, 55.7, 43.6, 29.9, 29.9, 14.3. HRESI-TOFMS m/z [M+H]$^+$ 572.2120 (calcd for C$_{29}$H$_{34}$NO$_{11}$$^+$, 572.2126, 1.1 ppm error). HPLC purity: 98.3% (210 nm).

(2S,3S,4R,5R,6S)—N-Cyclopentyl-6-(2-(3,4-dimethoxyphenyl)-5,7-dimethoxy-4-oxo-4H-chromen-6-yl)-3,4,5-trihydroxytetrahydro-2H-pyran-2-carboxamide (16)

Light yellow solid (86% yield). $^1$H NMR (DMSO-d$_6$) δ 7.66 (d, J=8.4 Hz, 1H), 7.53 (d, J=2.1 Hz, 1H), 7.16 (s, 1H), 7.12 (d, =8.4 Hz, 1H), 6.75 (d, =6.5 Hz, 1H), 4.64 (br d, J=10.2 Hz, 1H), 3.95 (m, 1H), 3.87 (s, 3H), 3.82 (s, 3H), 3.79 (m, 1H), 3.77 (s, 3H), 3.71 (s, 3H), 3.53 (m, 1H), 3.51 (m, 1H), 3.21 (m, 1H), 1.79-1.40 (m, 8H). $^{13}$C NMR (DMSO-d$_6$) δ 175.4, 167.1, 163.6, 161.4, 160.3, 158.8, 152.1, 149.1, 123.0, 119.8, 112.1, 111.8, 109.2, 107.7, 107.1, 97.3, 80.2, 78.5, 74.2, 71.2, 68.6, 63.6, 62.8, 56.3, 55.9, 50.5, 32.1, 32.1, 23.6, 23.6. HRESI-TOFMS m/z [M+H]$^+$ 586.2291 (calcd for C$_{30}$H$_{36}$NO$_{11}$$^+$, 586.2283, −1.4 ppm error). HPLC purity: 96.6% (210 nm).

(2S,3S,4R,5R,6S)—N-Cyclohexyl-6-(2-(3,4-dimethoxyphenyl)-5,7-dimethoxy-4-oxo-4H-chromen-6-yl)-3,4,5-trihydroxytetrahydro-2H-pyran-2-carboxamide (17)

Light yellow solid (88% yield). $^1$H NMR (DMSO-d$_6$) δ 7.68 (d, J=8.4 Hz, 1H), 7.55 (d, J=2.1 Hz, 1H), 7.14 (s, 1H), 7.12 (d, J=8.4 Hz, 1H), 6.80 (d, J=6.5 Hz, 1H), 4.65 (br d, J=10.2 Hz, 1H), 4.04 (q, J=8.4 Hz, 1H), 3.88 (s, 3H), 3.84 (s, 3H), 3.79 (s, 3H), 3.74 (s, 3H), 3.58 (m, 1H), 3.51 (m, 1H), 3.49 (m, 1H), 3.21 (m, 1H), 1.74-1.47 (m, 6H), 1.27-0.99 (m, 4H). $^{13}$C NMR (DMSO-d$_6$) δ 175.5, 167.2, 163.2, 161.3, 160.3, 158.8, 152.0, 149.1, 123.1, 119.8, 112.0, 111.4, 109.4, 107.2, 107.0, 96.9, 80.5, 79.1, 74.1, 71.6, 70.6, 63.9, 62.7, 56.4, 56.0, 47.8, 32.6, 32.6, 29.1, 24.6, 24.6. HRESI-TOFMS m/z [M+H]$^+$ 600.2446 (calcd for C$_{31}$H$_{38}$NO$_{21}$$^+$, 600.2439, −1.1 ppm error). HPLC purity: 98.6% (210 nm).

(2S,3S,4R,5R,6S)—N-(Cyclohexylmethyl)-6-(2-(3,4-dimethoxyphenyl)-5,7-dimethoxy-4-oxo-4H-chromen-6-yl)-3,4,5-trihydroxytetrahydro-2H-pyran-2-carboxamide (18)

Light yellow solid (88% yield). $^1$H NMR (DMSO-d$_6$) δ 7.66 (d, J=8.7 Hz, 1H), 7.54 (d, J=2.0 Hz, 1H), 7.13 (s, 1H), 7.11 (d, J=8.7 Hz, 1H), 6.76 (d, J=6.2 Hz, 1H), 4.66 (br d, J=9.9 Hz, 1H), 4.05 (q, J=9.9 Hz, 1H), 3.87 (s, 3H), 3.83 (s, 3H), 3.78 (s, 3H), 3.73 (s, 3H), 3.61 (m, 1H), 3.48 (m, 1H), 3.23 (m, 1H), 2.87 (m, 2H), 1.69-1.47 (m, 6H), 1.33 (m, 1H), 1.08 (m, 2H), 0.80 (m, 2H). $^{13}$C NMR (DMSO-d$_6$) δ 176.0, 167.0, 163.7, 160.8, 160.6, 158.9, 152.0, 149.3, 123.4, 119.7, 112.0, 111.7, 109.3, 107.2, 107.1, 96.2, 80.3, 78.7, 74.7, 71.3, 69.9, 63.8, 63.1, 56.6, 56.2, 45.1, 37.1, 30.6, 30.6, 26.3, 25.7, 25.7. HRESI-TOFMS m/z [M+H]$^+$ 614.2597 (calcd for C$_{32}$H$_{40}$NO$_{11}$$^+$, 614.2596, −0.1 ppm error). HPLC purity: 98.3% (210 nm).

(2S,3S,4R,5R,6S)—N-(Adamantan-1-yl)-6-(2-(3,4-dimethoxyphenyl)-5,7-dimethoxy-4-oxo-4H-chromen-6-yl)-3,4,5-trihydroxytetrahydro-2H-pyran-2-carboxamide (19)

Light yellow solid (81% yield). $^1$H NMR (DMSO-$d_6$) δ 7.67 (d, J=8.4 Hz, 1H), 7.54 (d, J=2.1 Hz, 1H), 7.13 (s, 1H), 7.12 (d, J=8.4 Hz, 1H), 6.78 (d, J=6.8 Hz, 1H), 4.65 (br d, J=10.2 Hz, 1H), 4.03 (m, 1H), 3.88 (s, 3H), 3.84 (s, 3H), 3.80 (s, 3H), 3.74 (s, 3H), 3.57 (m, 1H), 3.52 (m, 1H), 3.49 (m, 1H), 1.96 (m, 3H), 1.88-1.57 (m, 12H). $^{13}$C NMR (DMSO-$d_6$) δ 175.3, 167.2, 163.3, 161.1, 160.2, 158.9, 152.1, 149.2, 123.2, 119.8, 112.1, 111.6, 109.5, 107.2, 107.0, 97.0, 80.7, 79.2, 74.2, 71.7, 70.5, 63.9, 62.5, 56.4, 56.0, 51.2, 41.2, 41.2, 41.2, 36.1, 36.1, 36.1, 28.9, 28.9, 28.9. HRESI-TOFMS m/z [M+H]$^+$ 652.2764 (calcd for $C_{35}H_{42}NO_{11}^+$, 652.2752, −1.8 ppm error). HPLC purity: 97.7% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-phenyltetrahydro-2H-pyran-2-carboxamide (20)

Light yellow solid (88% yield). $^1$H NMR (DMSO-$d_6$) δ 7.66 (dd, J=8.6, 2.2 Hz, 1H), 7.62 (dd, J=8.2, 2.5 Hz, 2H), 7.55 (d, J=2.2 Hz, 1H), 7.28 (td, J=8.1, 2.2 Hz, 2H), 7.16-7.10 (m, 2H), 7.03 (t, J=7.4 Hz, 1H), 6.77 (d, J=6.5 Hz, 1H), 4.75 (br d, J=9.7 Hz, 1H), 4.12 (td, J=9.7, 2.4 Hz, 1H), 3.94 (s, 3H), 3.89 (s, 3H), 3.85 (s, 3H), 3.84 (m, 1H), 3.79 (s, 3H), 3.66 (m, 1H), 3.29 (m, 1H). $^{13}$C NMR (DMSO-$d_6$) δ 175.4, 167.3, 163.4, 161.9, 160.3, 158.8, 151.8, 149.1, 138.8, 128.6, 128.6, 123.4, 123.1, 119.5, 119.3, 119.3, 112.0, 111.8, 109.4, 107.1, 106.9, 97.1, 81.0, 78.6, 73.7, 71.2, 69.6, 63.4, 62.7, 56.5, 56.0. HRESI-TOFMS m/z [M+H]$^+$ 594.1986 (calcd for $C_{31}H_{32}NO_{11}^+$, 594.1970, −2.8 ppm error). HPLC purity: 96.5% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-benzyltetrahydro-2H-pyran-2-carboxamide (21)

Light yellow solid (92% yield). $^1$H NMR (500 MHz, DMSO-$d_6$) δ 7.67 (d, J=10.2 Hz, 1H), 7.54 (d, J=2.1 Hz, 1H), 7.29-7.16 (m, 5H), 7.16-7.08 (m, 2H), 6.80 (d, J=6.7 Hz, 1H), 4.68 (dd, J=9.8, 6.7 Hz, 1H), 4.27 (m, 2H), 4.10 (m, 1H), 3.87 (s, 3H), 3.83 (s, 3H), 3.79 (s, 3H), 3.75 (s, 3H), 3.71 (m, 1H), 3.57 (m, 1H), 3.26 (m, 1H). $^{13}$C NMR (DMSO-$d_6$) δ 175.6, 169.1, 163.6, 162.0, 160.3, 158.9, 151.8, 149.1, 139.2, 128.2, 128.2, 127.3, 127.3, 126.7, 123.1, 119.6, 112.1, 111.7, 109.2, 107.1, 107.0, 97.1, 80.2, 78.8, 73.7, 71.6, 71.0, 63.5, 62.8, 56.6, 56.0, 42.0. HRESI-TOFMS m/z [M+H]$^+$ 608.2130 (calcd for $C_{32}H_{34}NO_{11}^+$, 608.2126, −0.5 ppm error). HPLC purity: 97.1% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-tetrahydro-2H-pyran-2-carboxamide (22)

Light yellow solid (81% yield). $^1$H NMR (500 MHz, DMSO-$d_6$) δ 8.40 (d, J=5.0 Hz, 2H), 7.68 (d, J=8.5 Hz, 1H), 7.60 (d, J=5.0 Hz, 2H), 7.55 (s, 1H), 7.15 (s, 1H), 7.12 (d, J=8.5 Hz, 1H), 6.81 (d, J=6.9 Hz, 1H), 4.72 (br d, J=9.7 Hz, 1H), 4.11 (td, J=9.2, 4.1 Hz, 1H), 3.94 (m, 1H), 3.88 (s, 3H), 3.84 (s, 3H), 3.83 (s, 3H), 3.76 (s, 3H), 3.62 (m, 1H), 3.29 (m, 1H). $^{13}$C NMR (DMSO-$d_6$) δ 175.6, 167.5, 163.3, 161.7, 160.2, 158.7, 152.0, 150.9, 150.9, 149.2, 145.3, 123.1, 119.9, 112.1, 113.9, 113.9, 111.5, 109.8, 107.5, 106.8, 97.1, 81.2, 78.8, 74.4, 71.5, 69.8, 63.9, 63.0, 56.5, 56.1. HRESI-TOFMS m/z [M+H]$^+$ 595.1921 (calcd for $C_{30}H_{31}N_2O_{11}^+$, 595.1922, 0.1 ppm error). HPLC purity: 97.8% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-(thiazol-2-yl)tetrahydro-2H-pyran-2-carboxamide (23)

Light yellow solid (80% yield). $^1$H NMR (DMSO-$d_6$) δ 7.68 (d, J 8.8 Hz, 1H), 7.56 (d, J=2.0 Hz, 1H), 7.53 (d, J=1.7 Hz, 1H), 7.18 (d, J=1.7 Hz, 1H), 7.17 (s, 1H), 7.12 (d, J 8.8 Hz, 1H), 6.82 (d, J=6.8 Hz, 1H), 4.67 (br d, J=10.5 Hz, 1H), 4.03 (m, 1H), 3.89 (s, 3H), 3.84 (s, 3H), 3.82 (s, 3H), 3.76 (s, 3H), 3.60 (m, 1H), 3.55 (m, 1H), 3.23 (m, 1H). $^{13}$C NMR (DMSO-$d_6$) δ 175.4, 168.5, 163.2, 162.3, 161.6, 160.5, 158.9, 151.9, 149.2, 137.2, 123.3, 119.8, 114.1, 111.9, 111.5, 109.5, 107.3, 105.8, 97.3, 80.0, 79.2, 74.3, 72.1, 70.3, 63.7, 62.9, 56.2, 56.0. HRESI-TOFMS m/z [M+H]$^+$ 601.1493 (calcd for $C_{28}H_{29}N_2O_{11}S^+$, 601.1487, −1.1 ppm error). HPLC purity: 96.8% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-(4-fluorophenyl) tetrahydro-2H-pyran-2-carboxamide (24)

Light yellow solid (88% yield). $^1$H NMR (DMSO-$d_6$) δ 7.70-7.61 (m, 3H), 7.54 (d, J=2.1 Hz, 1H), 7.18-7.08 (m, 4H), 6.78 (d, J=7.1 Hz, 1H), 4.72 (dd, J=12.0, 9.7 Hz, 1H), 4.11 (q, J=8.7 Hz, 1H), 3.92 (s, 3H), 3.88 (s, 3H), 3.84 (s, 3H), 3.83 (m, 1H), 3.76 (s, 3H), 3.61 (m, 1H), 3.28 (m, 1H). $^{13}$C NMR (DMSO-$d_6$) δ 175.6, 167.4, 162.8, 160.4, 160.1, 158.6, 156.9, 150.7, 149.2, 136.5, 121.2, 121.2, 123.5, 119.8, 115.5, 115.5, 113.5, 111.8, 109.3, 107.0, 105.7, 97.2, 81.2, 78.5, 74.7, 71.7, 70.4, 63.7, 63.0, 56.1, 55.9. HRESI-TOFMS m/z [M+H]$^+$ 612.1892 (calcd for $C_{31}H_{31}FNO_{11}^+$, 612.1876, −2.7 ppm error). HPLC purity: 97.1% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-(4-fluorobenzyl) tetrahydro-2H-pyran-2-carboxamide (25)

Light yellow solid (89% yield). $^1$H NMR (500 MHz, DMSO-$d_6$) δ 7.68 (d, J=8.5 Hz, 1H), 7.55 (d, J=2.1 Hz, 1H), 7.27 (ddd, J=8.1, 5.4, 2.2 Hz, 2H), 7.18-7.06 (m, 4H), 6.80 (d, J=6.8 Hz, 1H), 4.67 (t, J=9.3 Hz, 1H), 4.24 (dd, J=9.9, 9.0 Hz, 2H), 4.07 (m, 1H), 3.88 (s, 3H), 3.84 (s, 3H), 3.78 (s, 3H), 3.74 (s, 3H), 3.69 (m, 1H), 3.54 (m, 1H), 3.24 (m, 1H). $^{13}$C NMR (DMSO-$d_6$) δ 175.7, 169.1, 163.5, 162.0, 161.2, 160.4, 159.0, 151.9, 149.1, 135.4, 129.3, 129.3, 126.5, 119.7, 115.1, 115.1, 111.8, 111.3, 109.3, 107.1, 105.5, 97.2, 80.2, 78.8, 73.7, 71.9, 71.0, 63.6, 62.9, 56.6, 55.9, 41.3. HRESI-TOFMS m/z [M+H]$^+$ 626.2043 (calcd for $C_{32}H_{33}FNO_{11}^+$, 626.2032, −1.7 ppm error). HPLC purity: 97.4% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-(2-fluoroethyl)tetrahydro-2H-pyran-2-carboxamide (26)

Light yellow solid (84% yield). $^1$H NMR (DMSO-$d_6$) δ 7.68 (d, J=8.7 Hz, 1H), 7.56 (d, J=2.1 Hz, 1H), 7.17 (s, 1H), 7.12 (d, J=8.7 Hz, 1H), 6.82 (d, J=6.6 Hz, 1H), 4.67 (br d, J=10.5 Hz, 1H), 4.45 (m, 1H), 4.35 (m, 1H), 4.07 (t, J=9.2 Hz, 1H), 3.89 (s, 3H), 3.85 (s, 3H), 3.80 (s, 3H), 3.75 (s, 3H), 3.60 (m, 1H), 3.50 (m, 1H), 3.23 (m, 1H), 3.37 (m, 2H). $^{13}$C NMR (DMSO-d$_6$) δ 175.1, 168.6, 163.5, 161.6, 160.5, 158.9, 151.9, 149.2, 123.6, 119.7, 111.8, 111.4, 109.3, 107.2, 105.5, 97.3, 81.7, 79.9, 79.4, 74.3, 72.3, 70.3, 63.5, 62.9, 56.1, 55.9, 39.1. HRESI-TOFMS m/z [M+H]$^+$ 564.1892 (calcd for $C_{27}H_{31}FNO_{11}^+$, 564.1876, −2.9 ppm error). HPLC purity: 97.5% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-(2,2,2-trifluoroethyl) tetrahydro-2H-pyran-2-carboxamide (27)

Light yellow solid (85% yield). $^1$H NMR (DMSO-d$_6$) δ 7.68 (dd, J=8.5, 2.0 Hz, 1H), 7.56 (d, J=2.0 Hz, 1H), 7.17 (s, 1H), 7.12 (d, J=8.5 Hz, 1H), 6.81 (d, J=7.7 Hz, 1H), 4.68 (br d, J=9.7 Hz, 1H), 4.07 (q, J=9.1 Hz, 1H), 3.89 (s, 3H), 3.85 (s, 3H), 3.78 (s, 3H), 3.75 (s, 3H), 3.69 (m, 1H), 3.48 (m, 1H), 3.67 (m, 2H), 3.21 (m, 1H). $^{13}$C NMR (DMSO-d$_6$) δ 174.5, 169.5, 163.4, 161.3, 160.4, 158.9, 151.8, 149.1, 125.0, 123.4, 119.7, 112.1, 111.2, 109.4, 107.1, 105.4, 97.2, 80.4, 78.5, 74.8, 71.6, 69.5, 63.6, 62.7, 56.3, 55.9, 41.6. HRESI-TOFMS m/z [M+H]$^+$ 600.1700 (calcd for $C_{27}H_{29}F_3NO_{11}^+$, 600.1687, −2.2 ppm error). HPLC purity: 96.8% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-(3-fluoropropyl) tetrahydro-2H-pyran-2-carboxamide (28)

Light yellow solid (86% yield). $^1$H NMR (DMSO-d$_6$) δ 7.68 (d, J=8.7 Hz, 1H), 7.56 (d, J=2.1 Hz, 1H), 7.17 (s, 1H), 7.12 (d, J=8.7 Hz, 1H), 6.82 (d, J=6.4 Hz, 1H), 4.66 (br d, J=10.6 Hz, 1H), 4.46 (m, 1H), 4.37 (m, 1H), 4.07 (m, 1H), 3.89 (s, 3H), 3.85 (s, 3H), 3.80 (s, 3H), 3.74 (s, 3H), 3.59 (m, 1H), 3.50 (m, 1H), 3.22 (m, 1H), 3.12 (m, 2H), 1.83-1.68 (m, 2H). $^{13}$C NMR (DMSO-d$_6$) δ 175.1, 168.5, 163.4, 161.6, 160.6, 158.8, 151.9, 149.3, 123.7, 119.8, 111.9, 111.5, 109.6, 107.3, 105.5, 97.3, 81.9, 80.2, 78.8, 74.2, 71.8, 70.6, 63.6, 62.8, 56.2, 55.8, 34.9, 30.0. HRESI-TOFMS m/z [M+H]$^+$ 578.2041 (calcd for $C_{28}H_{33}FNO_{11}^+$, 578.2032, −1.6 ppm error). HPLC purity: 98.3% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N-(3,3,3-trifluoropropyl) tetrahydro-2H-pyran-2-carboxamide (29)

Light yellow solid (85% yield). $^1$H NMR (DMSO-d$_6$) δ 7.68 (d, J=8.4 Hz, 1H), 7.55 (d, J=2.2 Hz, 1H), 7.14 (s, 1H), 7.12 (d, J=8.4 Hz, 1H), 6.81 (d, J=5.5 Hz, 1H), 4.68 (br d, J=10.0 Hz, 1H), 4.07 (m, 1H), 3.89 (s, 3H), 3.85 (s, 3H), 3.80 (s, 3H), 3.74 (s, 3H), 3.61 (m, 1H), 3.49 (m, 1H), 3.28 (m, 2H), 3.21 (m, 1H), 2.40 (m, 2H). $^{13}$C NMR (DMSO-d$_6$) δ 174.6, 169.3, 163.4, 161.1, 160.3, 158.7, 151.8, 149.1, 125.7, 123.1, 119.6, 111.7, 110.9, 109.2, 107.0, 105.2, 97.4, 79.6, 78.3, 73.6, 71.6, 69.5, 63.4, 62.7, 56.0, 55.8, 32.8, 32.1. HRESI-TOFMS m/z [M+H]$^+$ 614.1857 (calcd for $C_{28}H_{31}F_3NO_{11}^+$, 614.1844, −2.2 ppm error). HPLC purity: 97.2% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N—((S)-1,1,1-trifluoropropan-2-yl)tetrahydro-2H-pyran-2-carboxamide (30)

Light yellow solid (82% yield). $^1$H NMR (500 MHz, DMSO-d$_6$) δ 7.67 (dd, J=8.5, 2.1 Hz, 1H), 7.55 (d, J=2.1 Hz, 1H), 7.15 (br s, 1H), 7.12 (d, J=8.5 Hz, 1H), 6.78 (d, J=6.2 Hz, 1H), 4.69 (d, J=9.6 Hz, 1H), 4.55 (m, 1H), 4.07 (m, 1H), 3.89 (s, 3H), 3.85 (s, 3H), 3.79 (s, 3H), 3.76 (s, 3H), 3.71 (m, 1H), 3.56 (m, 1H), 3.24 (m, 1H), 1.23 (d, J=6.8 Hz, 3H). $^{13}$C NMR (125 MHz, DMSO-d$_6$) δ 175.5, 168.8, 163.5, 161.7, 160.3, 158.6, 152.1, 149.1, 124.4, 123.1, 119.5, 111.8, 111.3, 109.4, 107.7, 106.9, 96.2, 79.8, 78.3, 73.8, 71.3, 70.3, 62.9, 62.7, 55.9, 55.6, 45.1, 13.3. HRESI-TOFMS m/z [M+H]$^+$ 614.1843 (calcd for $C_{28}H_{31}F_3NO_{11}^+$, 614.1844, 0.1 ppm error). HPLC purity: 98.1% (210 nm).

(2S,3S,4R,5R,6S)-6-(2-(3,4-Dimethoxyphenyl)-5,7-dimethoxy-4-oxo-4H-chromen-6-yl)-3,4,5-trihydroxy-N—((R)-1,1,1-trifluoropropan-2-yl) tetrahydro-2H-pyran-2-carboxamide (31)

Light yellow solid (86% yield). $^1$H NMR (500 MHz, DMSO-d$_6$) δ 7.66 (dd, J=8.5, 2.0 Hz, 1H), 7.55 (d, J−2.0 Hz, 1H), 7.14 (br s, 1H), 7.12 (d, =8.5 Hz, 1H), 6.77 (d, J=6.4 Hz, 1H), 4.68 (d, J=9.8 Hz, 1H), 4.54 (m, 1H), 4.06 (m, 1H), 3.88 (s, 3H), 3.84 (s, 3H), 3.79 (s, 3H), 3.75 (s, 3H), 3.71 (m, 1H), 3.55 (m, 1H), 3.24 (m, 1H), 1.23 (d, J=6.8 Hz, 3H). $^{13}$C NMR (125 MHz, DMSO-d$_6$) δ 175.3, 168.6, 163.4, 161.5, 160.2, 158.5, 152.1, 149.0, 124.2, 123.0, 119.4, 111.6, 111.1, 109.3, 107.6, 106.8, 96.4, 79.7, 78.5, 73.9, 71.2, 70.4, 63.1, 62.5, 55.7, 55.4, 45.1, 13.3. HRESI-TOFMS m/z [M+H]$^+$ 614.1847 (calcd for $C_{28}H_{31}F_3NO_{11}^+$, 614.1844, −0.5 ppm error). HPLC purity: 96.5% (210 nm).

Kinase Luminescent Assay.

Kinase inhibition was assessed with the ADP-Glo Kinase Assay. For screening, 5 ng/µL of kinase was assayed in a reaction containing 50 ng/µL substrate, 40 mM Tris, pH 7.5, 20 mM MgCl$_2$, 0.1 mg/mL bovine serum albumin, 50 µM dithiothreitol (DTT), 25 µM ATP, varying concentrations of test samples or 5% DMSO as vehicle. The reaction mixture was incubated for 1 hour at room temperature followed by the addition of the ADP-Glo' reagents according to the manufacturer's protocol. The kinase inhibitor staurosporine was used at 1 µM as a reference control. Each data point was collected in quadruplicate of two independent experiments.

To study GSK-3β kinetics, a reaction solution contained 5 ng/µL kinase, 40 mM Tris, pH 7.5, 20 mM MgCl$_2$, 0.1 mg/mL BSA, 50 µM DTT, and varying concentrations of ATP or substrate GS2 (residues 636-662 of human muscle glycogen synthase) versus test samples. The mixture was incubated for 5, 15, 30, and 60 minutes at room temperature followed by the addition of the ADP-Glo' reagents according to the manufacturer's protocol. The Lineweaver-Burk representation is derived from the double reciprocal plotting of the enzyme kinetic data.

Cell Culture.

Human neuroblastoma SH-SY5Y cell line (Sigma-Aldrich, Saint Louis, Mo.) was cultured in DMEM/F12 (v/v 1:1) media supplemented with 2 mM glutamine, 10% heat-inactivated fetal bovine serum (FBS) and 1% antibiotics including penicillin and streptomycin. After reaching 70-80% confluence, cells were then subcultured on poly-L-lysine plates with 10 µM retinoic acid in a reduced serum media (1% FBS) to promote neuronal maturation and differentiation as described (Agholme, et al. (2010) *J. Alzheimer's Dis.* 20: 1069-1082). Cell cultures were incubated at 37° C. in a fully humidified atmosphere containing 5% CO$_2$.

Whole-Cell Lysate GSK-3β Assay.

The assay procedure was followed as described (Liang, et al. (2016) *ACS Chem. Neurosci.* 7:912-923). SH-SY5Y cells were washed with phosphate-buffered saline (PBS) and lysed with cell extraction buffer containing 10 mM Tris, pH 7.4, 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% sodium dodecyl sulfate (SDS), 0.5% sodium deoxycholate, 1 mM phenylmethanesulfonyl fluoride (PMSF) and a protease inhibitor cocktail. Lysate was diluted with kinase buffer (40 mM Tris, pH 7.5, 20 mM $MgCl_2$, 50 µM DTT, 400 µM ATP) to afford a concentration of 5 µg/µL of total protein, and split into aliquots. Recombinant human GSK-3β was fortified into lysate aliquots to a final concentration of 0.25% (wt/wt) of total protein. A lysate aliquot fortified with heat-inactivated GSK-3β was used as a negative control. The fortified lysate aliquots were incubated with test sample or 5% DMSO vehicle at 37° C. for 2 hours followed by ELISA analysis. The GSK-3β inhibitor TDZD-8 was used at 10 µM as a reference control.

Human Tau pS396 ELISA.

The quantitative determination of phosphorylated human tau at GSK-3β specific pS396 site was conducted by taking 50 µL diluted cell lysate and using a specific antibody against human tau [pS396] in a sandwich ELISA according to the manufacturer's protocol. Tau phosphorylation was quantified by measuring the absorbance at 450 nm in a microtiter plate reader. The analysis was collected in quadruplicate of two independent experiments.

$A\beta_{42}$ Oligomer Preparation.

The toxic oligomers of $A\beta_{42}$ were prepared as described (Liang, et al. (2016) *ACS Chem. Neurosci.* 7:912-923). Briefly, lyophilized $A\beta_{42}$ peptide was dissolved in hexafluoroisopropanol, dried under vacuum, and stored at −20° C. Immediately prior to use, the peptide residue was reconstituted in DMEM/F12 media to make a stock solution at 0.1 mM and incubated at 4° C. for 24 hours to form diffusible oligomers. $A\beta_{42}$ oligomers at a final concentration of 10 µM were assayed for cell viability.

Anti-$A\beta_{42}$ Neurotoxicity Assay.

SH-SY5Y cells were seeded at a density of $3\times10^5$ cells/mL in a 96-well plate in DMEM/F12 media containing 10 µM retinoic acid and 1% FBS to suppress cell proliferation. Cells were incubated under regular culture conditions for attachment. After 24 hours of plating, the cells were pre-treated with different concentrations of test samples or the 0.2% DMSO as a vehicle control for 1 hour and then co-incubated with 10 µM $A\beta_{42}$ for 72 hours. After the experimental treatment, the cells were subject to a CELL-TITER® 96 AQueous One Solution Cell Proliferation MTX Assay according to the manufacturer's instruction. Staurosporine at 1 µM was used as a reference control for cytotoxicity, while 10 µM TDZD-8 was used as a reference control for GSK-3β inhibition. Each data point was collected in triplicate of two independent experiments.

PAMPA Studies.

A 96-well filter plate with 0.45 µm polyvinylidene fluoride (PVDF) membrane was pre-coated with tri-layer phospholipids. 300 µL of sample solutions (20 µM) in 5% DMSO-PBS at pH 7.4 were added to the donor wells. The accepter plate containing 200 µL 5% DMSO-PBS was then placed on top of the donor plate so that the artificial membrane was in contact with the solution below. The PAMPA system was covered with a lid and incubated for 5 hours at room temperature. The concentration of compound in the donor and acceptor wells was quantified by LC-ESI-QTOF-MS. Theophylline and atenolol known for their low permeability were used as negative controls, and desipramine known for its high permeability was used as a positive control. Samples were run in quadruplicate. $P_e$ values and R % were calculated according to the manufacturer's instruction.

Docking Studies.

Compounds of interest were docked with AutoDock Vina 1.1.2 (Trott & Olson (2010) *J. Comput. Chem.* 31:455-461; Forli, et al. (2016) *Nat. Protoc.* 11:905-919) using the X-ray crystallographic structures of GSK-3β (PDB codes 1PYX (Bertand, et al. (2003) *J. Mol. Biol.* 333:393-407) and 1H8F (Dajani, et al. (2001) *Cell* 105:721-32)). The PDB crystallographic structures were treated without water molecules according to the published GSK-3β docking protocols (Tapia-Rojas, et al. (2015) *Biochem. J.* 466:415-430; Forli, et al. (2016) *Nat. Protoc.* 11:905-919). Proteins were prepared by adding polar hydrogens and Gasteiger charges using AutoDockTools (Forli, et al. (2016) *Nat. Protoc.* 11:905-919). Ligands were optimized for their energy and geometry using MMFF94 and AM1 force fields prior to docking as described (Liang, et al. (2015) *J. Nat. Prod.* 78:543-547). All bonds of ligands were treated as rotatable except for the aromatic, alkenyl, carbonyl bonds and rings. The dimensions of the grid map were 30×30×30 points with a gild-point spacing of 1 Å. Docking was proceeded with an exhaustiveness value of 500 and a maximum output of 100 structures. Re-docking experiments were conducted using the ligands ANP and HEPES for 1PYX and 1H8F, respectively. ANP showed a binding pose at the ATP site of GSK-3β (PDB code 1PYX) with a RMSD of 0.33 Å as compared to its original crystal structure. HEPES showed a binding pose at the substrate site of GSK-3β (PDB code 1H8F) with a RMSD of 0.62 Å as compared to its original crystal structure. AutoDockTools was used to analyze the docking data of compounds of interest on molecular interactions including hydrogen bonds, hydrophobic contact, n-cation interactions, n-n interactions, and multipolar interactions.

Homology Modeling.

The GSK-3α homology model was built with the SWISS-MODEL server (Biasini, et al. (2015) *Nucl. Acids Res.* 42:W252-W258). The full sequence of human GSK-3α (UniProt code P49840) was obtained from the Universal Protein Resource. The target sequence was searched against BLAST and HHblits databases for evolutionary related protein structures. A total of 4470 templates were found. For each identified template, the template's quality was predicted from features of the target-template alignment. A template of the GSK-3β structure (PDB code 1PYX) showing the highest quality (sequence identity, 82.97%) in the template ranking was selected for model building. The model was built based on the target-template alignment using ProMod3. Coordinates that are conserved between the target and the template were copied from the template to the model. Insertions and deletions were remodeled using a fragment library. Side chains were then rebuilt. Finally, the geometry and energy minimization of the resulting model was performed using the OpenMM molecular mechanics force field. The model quality assessment was performed based on the global and per-residue model quality using the QMEAN scoring function.

Statistical Analysis.

Data were presented as the mean±SEM or ±SD. The data were analyzed by one-way ANOVA with Bonferroni's multiple comparison test, Tukey's multiple comparison post-hoc test, as well as Student t test. The p values less than 0.05 were considered statistically significant. Analyses were performed using Excel and GraphPad Prism.

Results and Discussion
Design and Synthesis.
A series of analogues of 1 were designed and synthesized (Table 1). The semi-synthesis of 6-C-glycosylflavones from 1 was carried out according to the route outlined in Scheme 1.
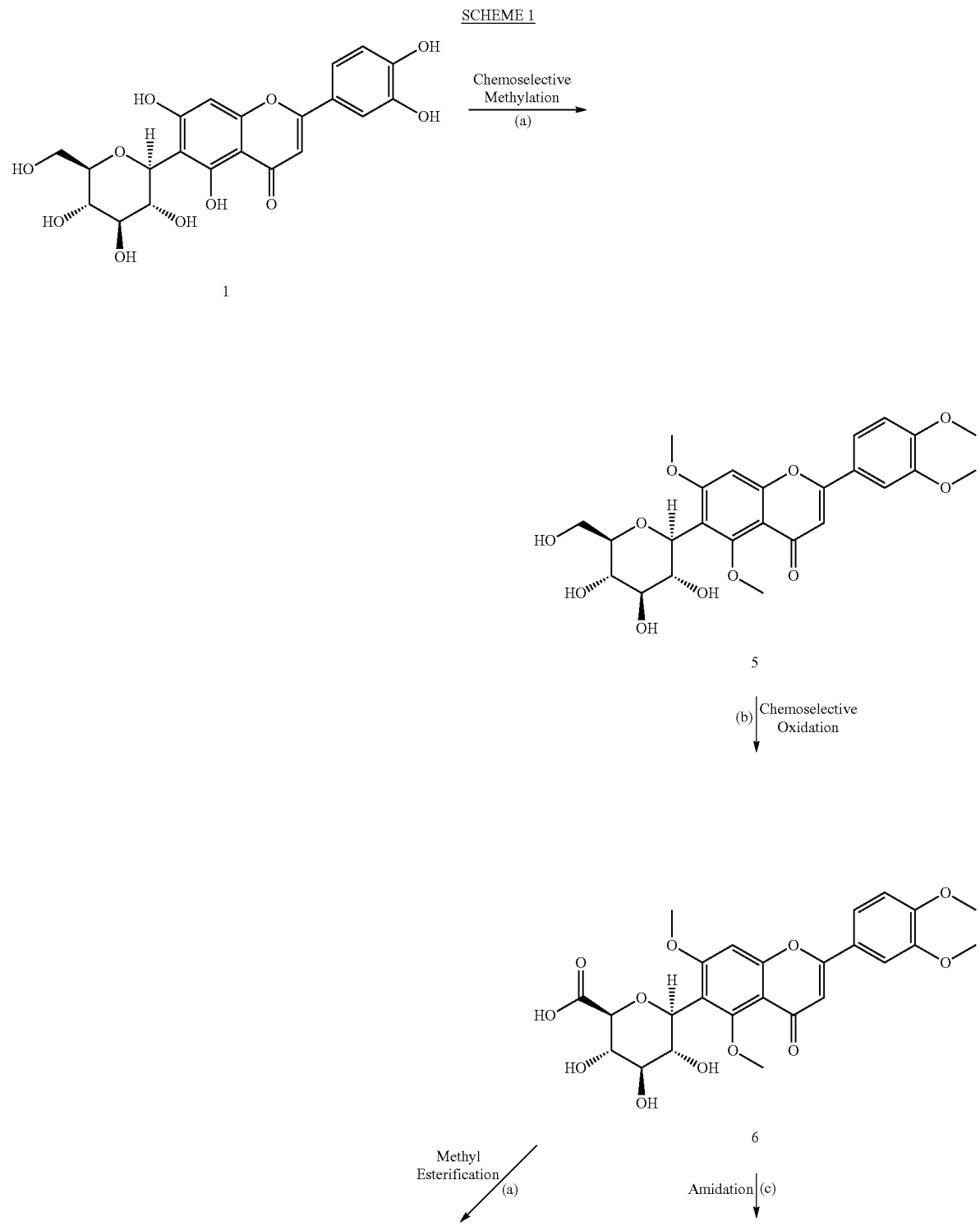

-continued

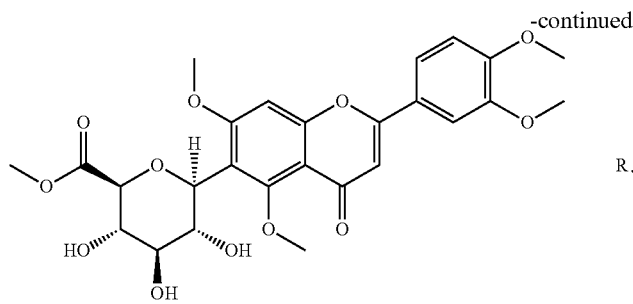

7

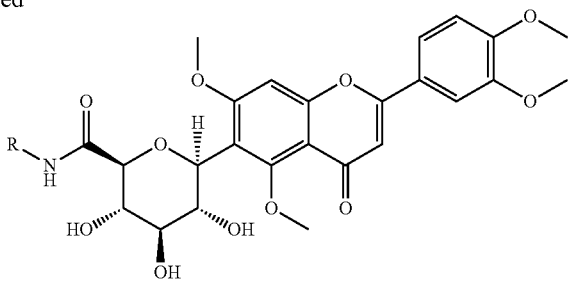

8-31

<sup>a</sup> Reagents and conditions: (a) TMSCHN$_2$, toluene, methanol, rt, 80%; (b) [TEMPO]$^+$[BF$_4$]$^-$, DCM, pyridine, rt, 95%; (c) R—NH$_2$, HCTU, DIPEA, DMF, DCM, rt, 80-90%.

The four phenolic hydroxyls on the flavone core of 1 were first selectively methylated by TMSCHN$_2$ in a methanolic toluene solution according to a previously described method (Liang, et al. (2011) *J. Org. Chem.* 76:3635-43). The resulting tetra-methylated product (5) then underwent an oxoammonium salt-mediated oxidation. An oxidation protocol (Bobbitt, et al. (2014) *J. Org. Chem.* 79:1055-67) was optimized using a [TEMPO]$^+$[BF$_4$]$^-$ salt in a pyridine base solution at room temperature, which chemoselectively transformed the primary alcohol to a carboxylic acid without affecting the secondary hydroxyls on the C-glycone. This method successfully afforded the desired product (6) in over 95% yield which was confirmed by ESI-TOF-MS and NMR analyses. The carboxylic acid derivative 6 was then subjected to methyl esterification to afford 7. In addition, a small library of hydrophobic amides (8-31) were generated by coupling 6 with a series of organic amines via HCTU catalysis. Aliphatic, alicyclic, aromatic and fluorinated amines were selected for the solution-phase amidation (Table 1). The resulting hydrophobic amides were evaluated on their structure-activity relationship, cytotoxicity, anti-Alzheimer's disease activity, and passive membrane permeability. All final products were characterized by NMR and HRMS, and were over 95% purity determined by HPLC-UV at 210 nm.

TABLE 1

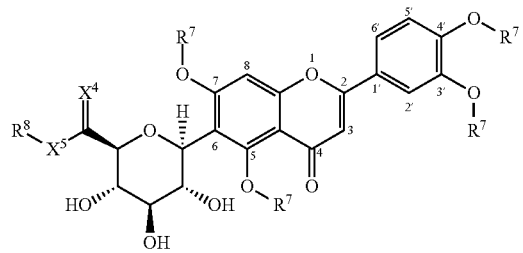

1, 5-31

| Compound | Functional group | | | |
|---|---|---|---|---|
| No. | R$^7$ | X$^4$ | X$^5$ | R$^8$ |
| 1 | H | H$_2$ | O | H |
| 5 | CH$_3$ | H$_2$ | O | H |
| 6 | CH$_3$ | O | O | H |
| 7 | CH$_3$ | O | O | CH$_3$ |

TABLE 1-continued

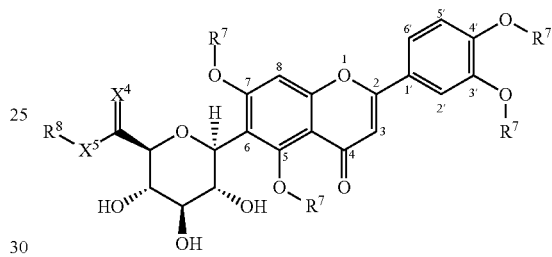

1, 5-31

| Compound | Functional group | | | |
|---|---|---|---|---|
| No. | R$^7$ | X$^4$ | X$^5$ | R$^8$ |
| 8 | CH$_3$ | O | NH | 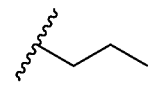 |
| 9 | CH$_3$ | O | NH | 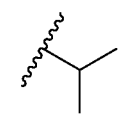 [SMILES: *C(C)C] |
| 10 | CH$_3$ | O | NH | 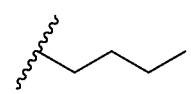 |
| 11 | CH$_3$ | O | NH | 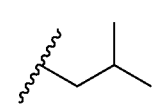 [SMILES: *CC(C)C] |
| 12 | CH$_3$ | O | NH | 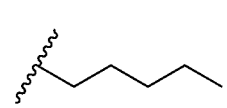 [SMILES: *CCCCC] |
| 13 | CH$_3$ | O | NH | 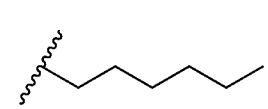 [SMILES: *CCCCCC] |
| 14 | CH$_3$ | O | NH | |

TABLE 1-continued

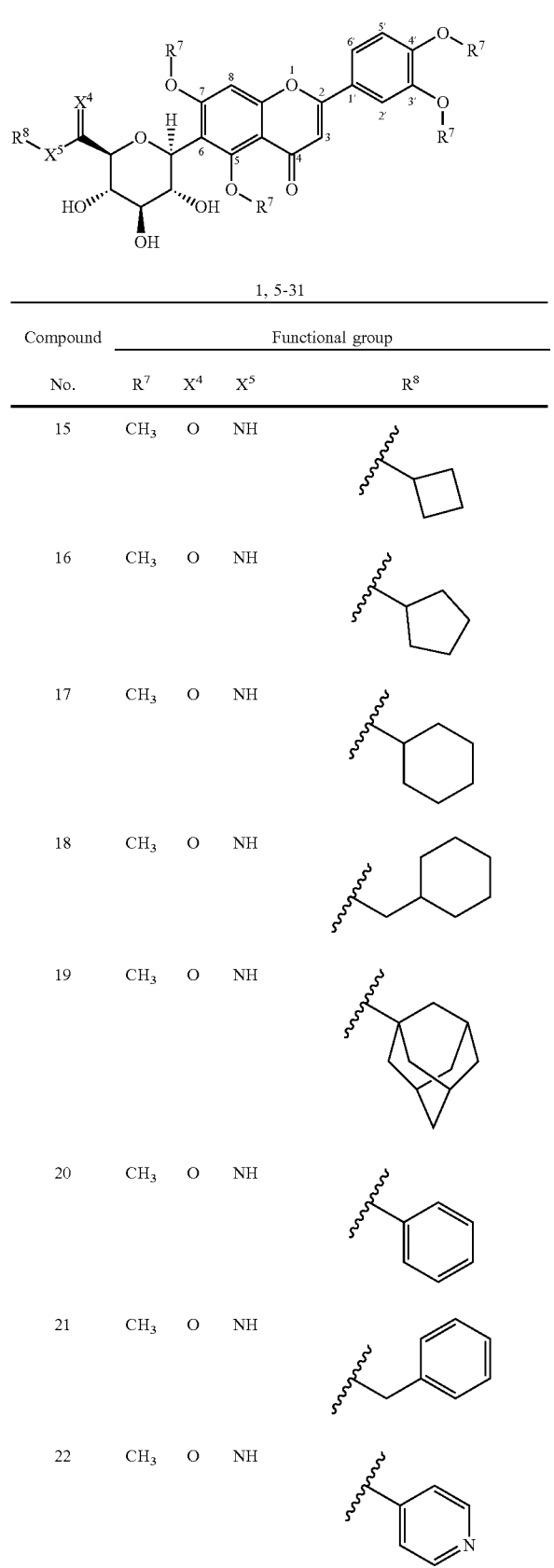

1, 5-31

| Compound No. | Functional group | | | |
|---|---|---|---|---|
| | R⁷ | X⁴ | X⁵ | R⁸ |
| 15 | CH₃ | O | NH | cyclobutyl |
| 16 | CH₃ | O | NH | cyclopentyl |
| 17 | CH₃ | O | NH | cyclohexyl |
| 18 | CH₃ | O | NH | CH₂-cyclohexyl |
| 19 | CH₃ | O | NH | adamantyl |
| 20 | CH₃ | O | NH | phenyl |
| 21 | CH₃ | O | NH | benzyl |
| 22 | CH₃ | O | NH | 4-pyridyl |

TABLE 1-continued

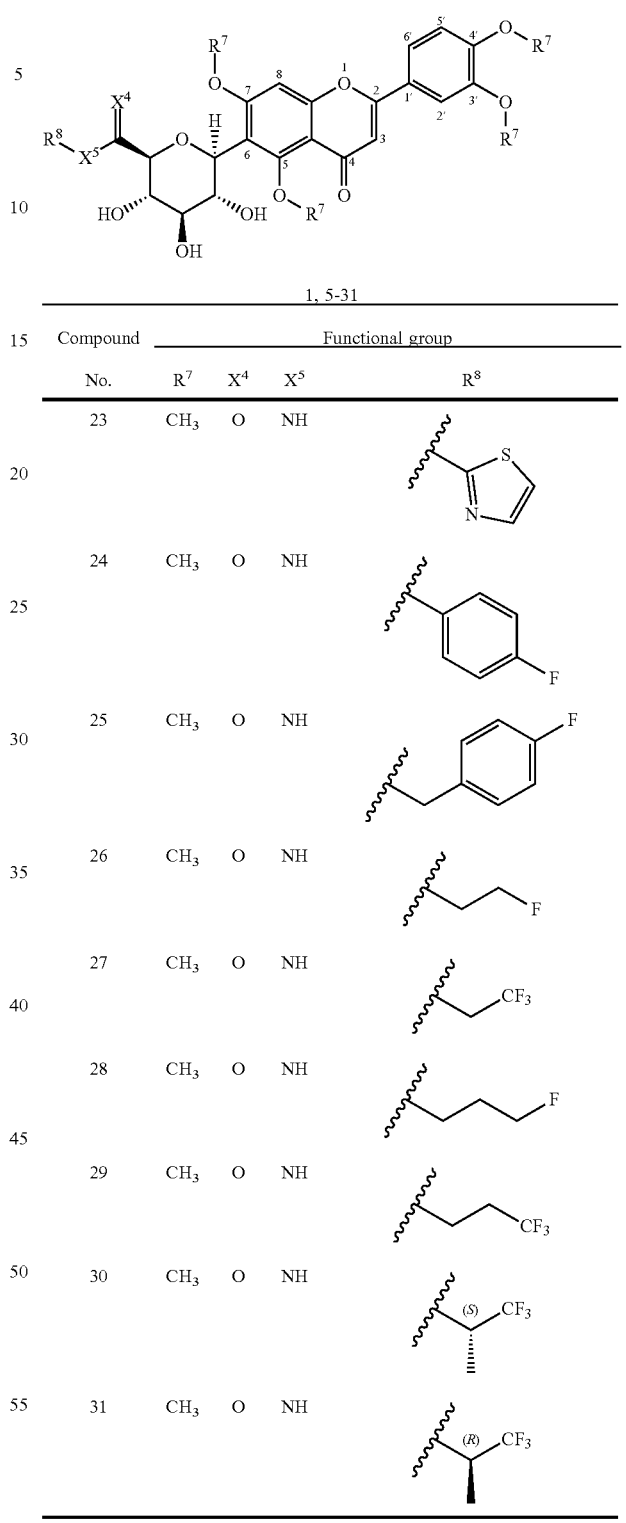

1, 5-31

| Compound No. | Functional group | | | |
|---|---|---|---|---|
| | R⁷ | X⁴ | X⁵ | R⁸ |
| 23 | CH₃ | O | NH | 2-thiazolyl |
| 24 | CH₃ | O | NH | 4-fluorophenyl |
| 25 | CH₃ | O | NH | 4-fluorobenzyl |
| 26 | CH₃ | O | NH | CH₂CH₂F |
| 27 | CH₃ | O | NH | CH₂CF₃ |
| 28 | CH₃ | O | NH | CH₂CH₂CH₂F |
| 29 | CH₃ | O | NH | CH₂CH₂CF₃ |
| 30 | CH₃ | O | NH | (S)-CH(CH₃)CF₃ |
| 31 | CH₃ | O | NH | (R)-CH(CH₃)CF₃ |

Structure-Activity Relationship and Ligand-Lipophilic Efficiency of C-Glycosylflavones to GSK-3β.

The semi-synthetic 6-C-glycosylflavones (5-31) were assayed on GSK-3 inhibition in comparison to four natural flavones with structural similarities (two 6-C-glycosylflavones isoorientin 1 and isovitexin 2, one 8-C-glycosylflavone orientin 3, and a flavone aglycone luteolin 4). Among the four flavones (1-4), 4 showed the highest potency against GSK-3β ($IC_{50}$, 3.1 μM) (Table 2), but it was nonspecific and promiscuous as previously noted (Liang, et al. (2016) *ACS Chem. Neurosci.* 7:912-923; Baell (2016) *J. Nat. Prod.* 79:616-628). By comparison, 1 and 2 with C-glycosides at position 6 showed a moderate potency against GSK-3β with an $IC_{50}$ value of 185 and 194 μM, respectively (Table 2). In contrast, 3, with an 8-C-glycoside, was inactive ($IC_{50}$, >5 mM). The results demonstrated that the presence and position of C-glycone on the flavone core are critical for GSK-3β inhibition.

TABLE 2

| Compound No. | $IC_{50}$ (μM) [a] | CLogP [b] |
|---|---|---|
| 1 | 184.9 ± 1.4 | 0.21 |
| 2 | 194.1 ± 1.0 | 0.80 |
| 3 | 5153 ± 31 | 0.21 |
| 4 | 3.1 ± 1.3 | 2.31 |
| 5 | 239.2 ± 1.2 | 1.28 |
| 6 | 237.3 ± 1.4 | 0.80 |
| 7 | 135.0 ± 1.3 | 1.21 |
| 8 | 29.2 ± 1.1 | 1.57 |
| 9 | 5.4 ± 0.1 | 1.35 |
| 10 | 33.3 ± 1.1 | 2.10 |
| 11 | 31.1 ± 1.2 | 1.97 |
| 12 | 28.0 ± 1.1 | 2.63 |
| 13 | 9.4 ± 0.9 | 3.16 |
| 14 | 25.8 ± 1.1 | 1.10 |
| 15 | 61.9 ± 1.9 | 1.43 |
| 16 | 13.1 ± 1.1 | 1.99 |
| 17 | 9.0 ± 1.3 | 2.55 |
| 18 | 26.0 ± 1.2 | 3.16 |
| 19 | 33.5 ± 0.8 | 3.17 |
| 20 | 19.7 ± 1.1 | 2.21 |
| 21 | 15.8 ± 1.2 | 2.34 |
| 22 | 35.6 ± 1.3 | 1.54 |
| 23 | 35.1 ± 1.0 | 1.45 |
| 24 | 56.2 ± 1.2 | 2.61 |
| 25 | 21.7 ± 1.2 | 2.48 |
| 26 | 34.8 ± 1.0 | 0.77 |
| 27 | 19.3 ± 0.8 | 1.31 |
| 28 | 49.5 ± 1.2 | 1.00 |
| 29 | 17.2 ± 0.9 | 1.29 |
| 30 | 0.59 ± 0.04 | 1.62 |
| 31 | 2.3 ± 0.5 | 1.62 |

[a] $IC_{50}$ values were the mean of quadruplicate of each of two independent experiments.
[b] CLogP values were calculated by a fragment-based method (Chou & Jurs (1979) *J. Chem. Inf. Comput. Sci.* 19: 172-178).

Figure 6:
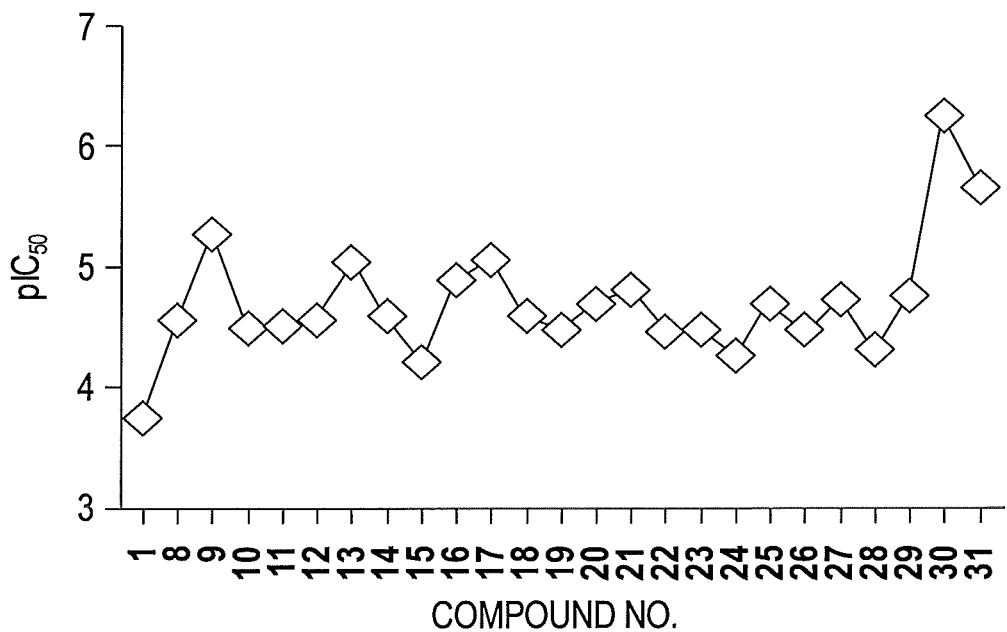
FIG. 6 shows a scatter plot of $pIC_{50}$ ($-Log\ IC_{50}$) for GSK-3β inhibitors 1 and 8-31. The parent compound isoorientin 1 is shown, as is aliphatic amide analogues 8-13, alicyclic amide analogues 14-19, aromatic amide analogues 20-23, and fluorinated amide analogues 24-31.

The tetra-methylated alcohol (5) and tetra-methylated carboxylic acid (6) slightly decreased the potency ($IC_{50}$, 237 and 239 μM, respectively) in comparison with 1, indicating a trivial contribution of the phenolic hydroxyl groups to GSK-3β inhibition. However, a methyl ester (7) ($IC_{50}$, 135 μM) increased the potency by 1.37-fold as compared to 1 ($IC_{50}$, 185 μM), indicating hydrophobic groups at the primary hydroxyl position are preferred for GSK-3β inhibition. Remarkably, transforming the primary alcohol to corresponding hydrophobic amides (8-31) (Table 2) significantly increased the potency against GSK-3β as most analogues displayed $IC_{50}$ values less than 50 μM and ten of them (9, 13, 16, 17, 20, 21, 27, 29, 30 and 31) were less than 20 μM. As shown in FIG. 6, the aliphatic (e.g., 9 and 13) and alicyclic amides (e.g., 16 and 17) exhibited a higher affinity to GSK-3β than the aromatic amides (e.g., 20-23). Small (14 and 15) or large (18 and 19) alicyclic rings showed a less affinity than the cyclopentyl (16) or cyclohexyl (17) analogues, plausibly due to the size of the hydrophobic concave cleft in the substrate site on GSK-3β. A branched isopropyl group (9, 30, and 31) showed a higher affinity than a linear propyl group (8, 28, and 29). Mono-fluorination of phenyl (24), benzyl (25), ethyl (26) or propyl (28) groups did not improve affinity as compared to non-fluorinated counterparts (e.g., 8, 20, and 21). It is interesting that a trifluoromethyl ($CF_3$) group has a significant effect on potency. Compounds 27, 29, 30 and 31 containing a $CF_3$ moiety consistently improved binding affinity to GSK-3β in comparison with no fluorine or mono-fluorinated counterparts (e.g., 8, 9, 26 and 28) (FIG. 6). In particular, 30 ($IC_{50}$, 0.59 μM) with a (S)—$CF_3$ group increased the potency against GSK-3β by 310-fold in comparison with 1, and was about 4-fold more potent than its epimer 31 with a (R)—$CF_3$ group ($IC_{50}$, 2.3 μM). All new analogues were not pan-assay interference compounds to GSK-3β, as determined with a detergent-based assay (Liang, et al. (2016) *ACS Chem. Neurosci.* 7:912-923; Baell (2016) *J. Nat. Prod.* 79:616-628; Feng & Shoichet (2006) *Nat. Protoc.* 1:550-553).

Figure 7:
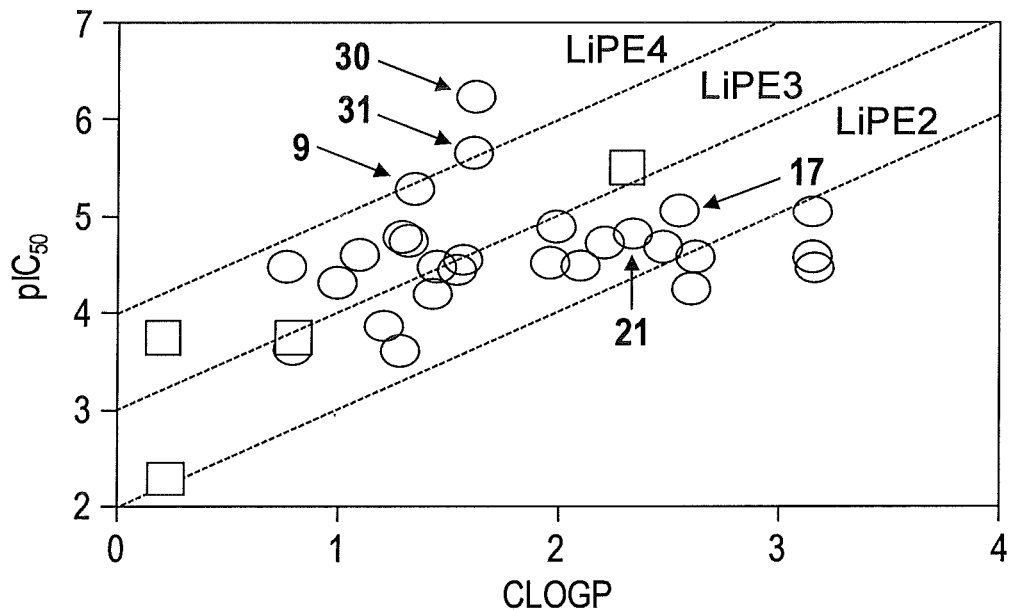
FIG. 7 shows a plot of CLogP versus pIC50 for GSK-3β inhibitors 1-31. Diagonal lines represent areas of the same LiPEs to estimate drug-likeness. LiPE=pIC50–CLogP. Squares: natural flavones; Circles: semi-synthetic flavones.

Ligand-lipophilic efficiency (LiPE) is a parameter commonly used in drug design to assess the quality of compound candidates. Lipophilicity is the most important drug-like physiochemical property that highly correlates to absorption, distribution, metabolism, excretion and toxicity (ADMET) profiles and ultimately to the pharmacological response for oral drugs Wager, et al. (2016) *ACS Chem. Neurosci.* 7:767-775). High potency (large $pIC_{50}$) is a desirable feature in drug candidates, as it reduces the risk of off-target and nonspecific pharmacology. Correlation between lipophilicity (CLogP) and potency ($pIC_{50}$) provides a valuable parameter to estimate drug-likeness (Freeman-Cook, et al. (2013) *Future Med. Chem.* 5:113-115). Many of the semi-synthetic analogues clustered in an upper-right range of the LiPEs between 2 and 4, indicating that both lipophilicity (CLogP) and GSK-3β inhibitory potency ($pIC_{50}$) had increased relative to 1 (FIG. 7). Particularly, 30 has the highest LiPE value (>4) among the analogues, indicating a unique contribution of the $CF_3$ moiety of 30 to improving potency and lipophilicity.

Evaluations of 1, 9, 17, 21, and 30 on Anti-Tau Hyperphosphorylation Mediated by GSK-3g.

Figure 8:
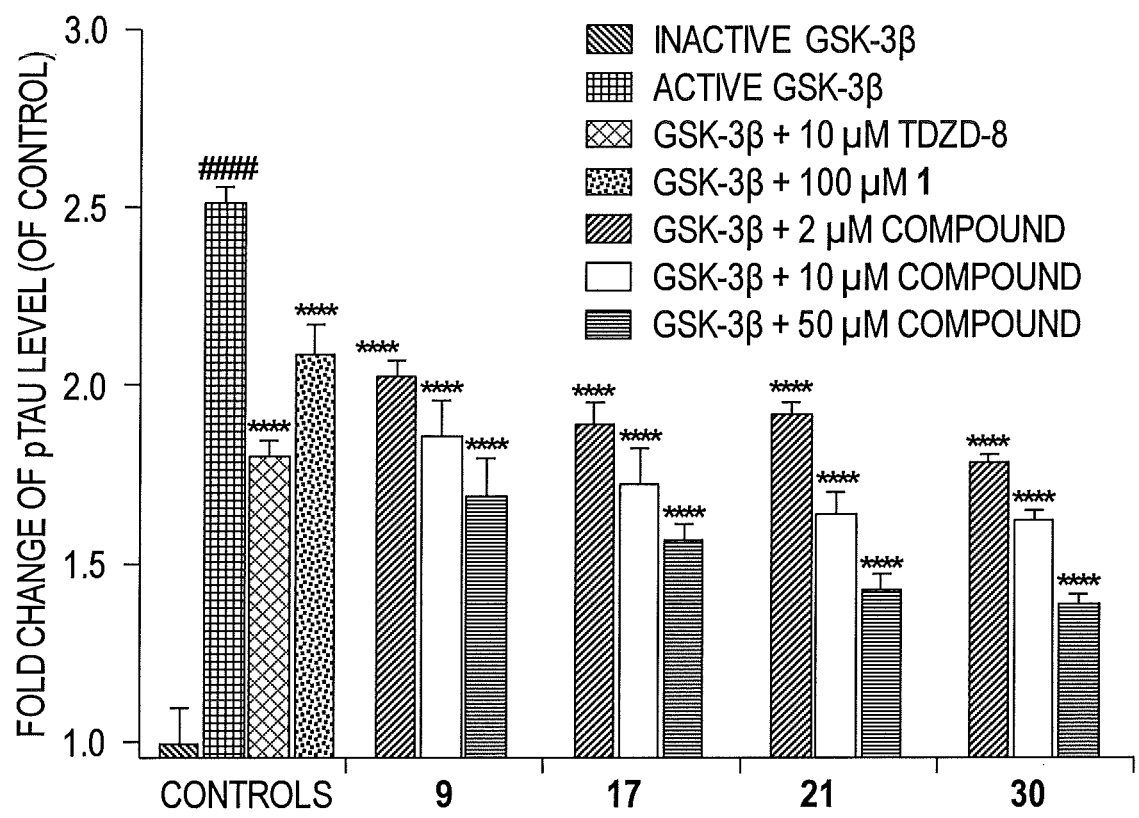
FIG. 8 shows that compounds 9, 17, 21 and 30 attenuate GSK-3β-mediated tau phosphorylation in a SH-SY5Y whole-cell lysate kinase assay. Cell lysate aliquots were fortified with 0.25% (wt/wt) GSK-3β, and incubated with 2 to 50 µM of 9, 17, 21, 30 or 5% DMSO vehicle in a kinase buffer at 37° C. for 2 hours. TDZD-8 (10 µM) and isoorientin (1, 100 µM) were used as reference controls. ELISA analysis was performed with specific antibody against Tau pS396 to quantify tau phosphorylation levels. Fold changes were calculated relative to the control with ±SEM (n=4). #### $p<0.0001$ relative to inactive GSK-3β fortified control; ****$p<0.0001$ relative to the active GSK-3β fortified control.

Compounds 9, 17, and 30 were selected for further evaluation on effect against GSK-3β-mediated tau hyperphosphorylation relative to 1, as they were the most potent GSK-3β inhibitors within each of the aliphatic, alicyclic, aromatic and fluorinated amide analogues, respectively. An in vitro GSK-3β assay using a whole-cell lysate of human SH-SY5Y neuroblastomas has been used to demonstrate that the pS396 site on tau protein is GSK-3β specific (Liang, et al. (2016) *ACS Chem. Neurosci.* 7:912-923). Direct GSK-3β inhibition by isoorientin 1 led to its consequent effect against GSK-3β-mediated tau hyperphosphorylation on the pS396 site in an ex vivo protein matrix of the SH-SY5Y lysate (Liang, et al. (2016) *ACS Chem. Neurosci.* 7:912-923). By analogy, an aliquot of lysate was fortified with GSK-3β (wt/wt 0.25%), and incubated with 9, 17, 21, or 30 at different concentrations (2, 10, and 50 μM) for 2 hours followed by an enzyme linked immunosorbent assay (ELISA) with an anti-tau pS396 antibody. TDZD-8 (10 μM) and 1 (100 μM) were used as reference controls. Quantitative ELISA measurements substantiated that introducing exogenous GSK-3β significantly increased phosphorylation by approximately 2.5-fold (p<0.0001) at the site pS396 on tau proteins as compared to their basal levels (lysate fortified with heat-inactivated GSK-3β) (FIG. 8). In contrast, treatment with compound 9, 17, 21, or 30 effectively attenuated tau hyperphosphorylation in a dose-dependent manner (p<0.0001). Notably, compound 30 at 10 μM showed a better inhibition against tau hyperphosphorylation compared to the known GSK-3l3 inhibitor TDZD-8 ($IC_{50}$, 2 μM) at the same concentration. These results demonstrated that the 6-C-glycosylflavone analogues of this invention indeed alleviate tau hyperphosphorylation.

GSK-3β Kinetic Studies on the Inhibition Mode of 30.

To determine the GSK-3β mechanism, the most potent analogue, compound 30, was assayed to competitively replace ATP or the GSK-3β substrate GS2 (a peptide derived from human muscle glycogen synthase). Under a constant concentration of the substrate GS2 (17 μM), ATP concentrations varied from 2 to 50 μM and 30 concentrations varied from 0 to 5 μM. The Lineweaver-Burk plots showed a convergence of intersecting lines on the x-axis, indicating an unaltered Michaelis-Menten constant ($K_m$) but a reduced GSK-3β activity (increased $1/V_{max}$) when the concentration of 30 increased. This indicated no competition between ATP and 30. In the second set of experiments under a constant concentration of ATP (10 μM), substrate GS2 concentrations varied from 8 to 66 μM and 30 concentrations varied from 0 to 5 μM. The Lineweaver-Burk plots showed that all lines intersected at the same point on the y-axis, indicating an unchanged $1/V_{max}$ but an increase of $K_m$ when the concentration of 30 increased. The data demonstrated that 30 competed with the substrate GS2. The enzyme inhibitory behaviors of 30 are similar to that of the parent compound 1 (Liang, et al. (2016) ACS Chem. Neurosci. 7:912-923) and therefore confirm that the new analogues are indeed substrate-competitive inhibitors of GSK-3β.

Kinase Selectivity Profile of 30.

Figure 9:
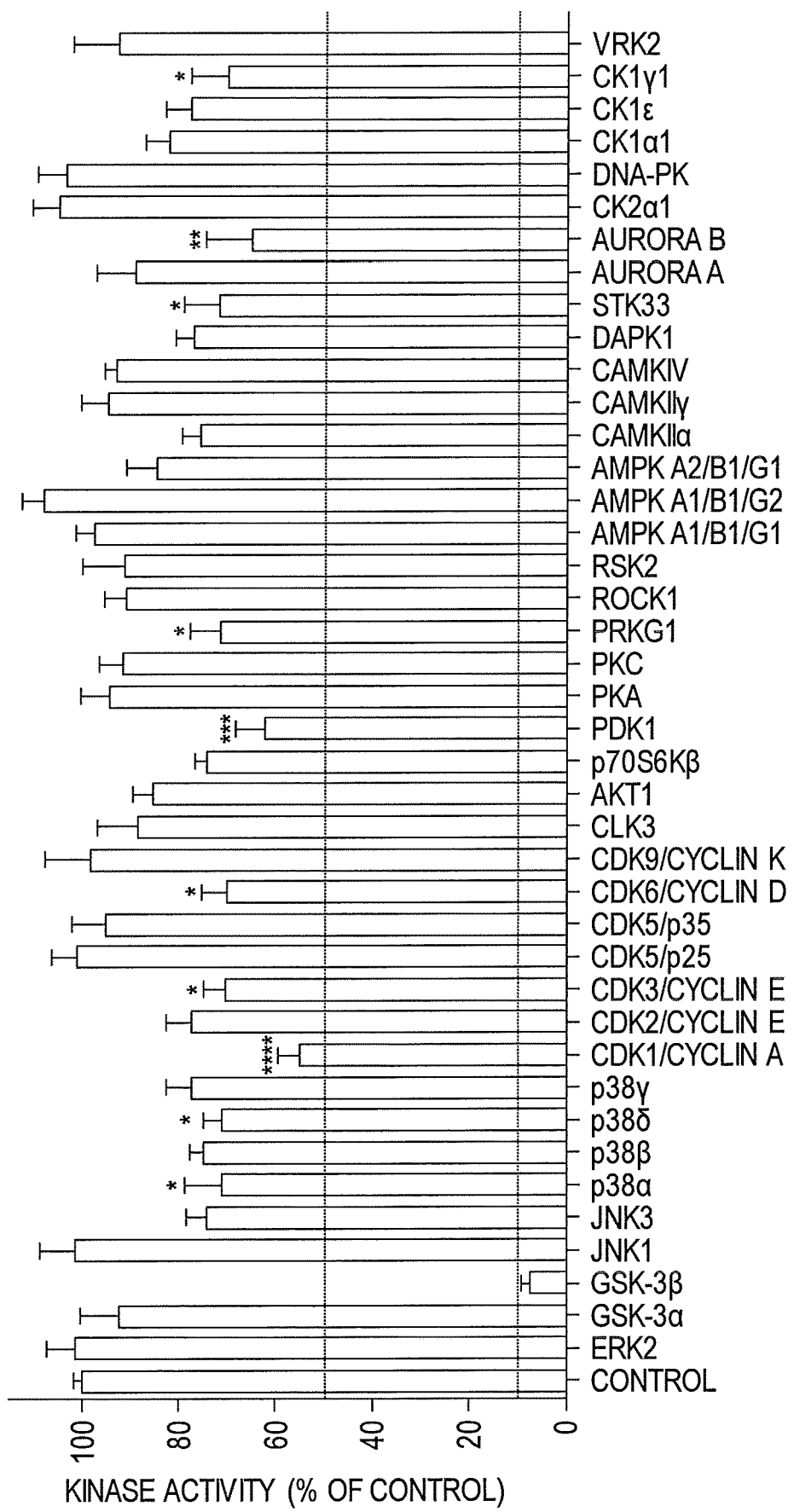
FIG. 9 shows the inhibitory effects of compound 30 on the activities of 41 kinases. Kinases were assayed in the presence of 5 µM 30 or control (5% DMSO vehicle). Data were the mean of quadruplicate of each of two independent experiments with ±SEM. $*p<0.05$, $p<0.01$, $*p<0.001$, $****p<0.0001$ relative to the control.

To assess kinase selectivity, compound 30 was screened against a panel of 41 human protein kinases of relevance to Alzheimer's disease and other CNS disorders (Martin, et al. (2013) Aging Res. Rev. 12:289-309). Compound 30 at 5 μM showed an overall good selectivity as it effectively inhibited GSK-3β by decreasing kinase activity by 92.3% (p<0.0001) in comparison to the control (100% kinase activity). Compound 30 showed only marginal or weak inhibition against 40 out of 41 kinases in the test panel (FIG. 9). Notably, between the two GSK-3 isoforms (GSK-3a and GSK-3β), compound 30 at 5 μM displayed a 12.3-fold specificity for GSK-3β (92.3% inhibition) versus GSK-3a (7.5% inhibition). The exceptional selectivity of compound 30 to GSK-3β can effectively minimize risk of off-target effects.

Evaluation of 30 on Cytotoxicity and Anti-Amyloid Neurotoxicity.

Figure 10:
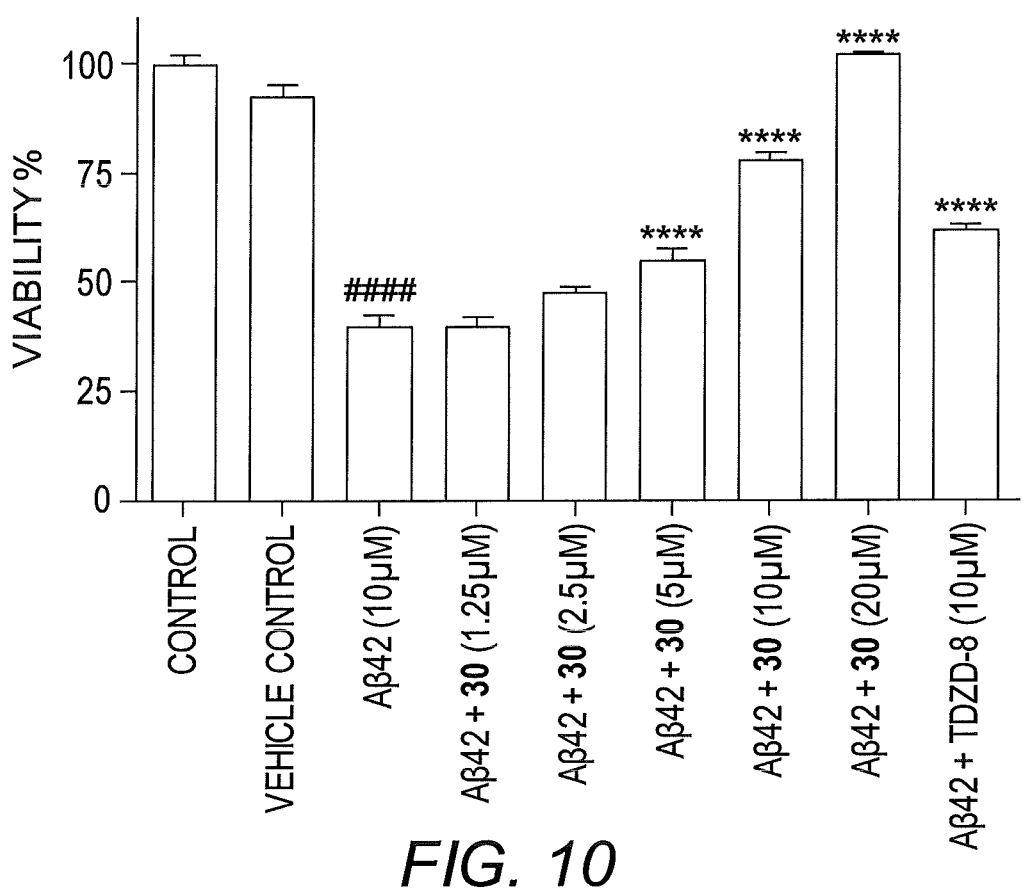
FIG. 10 shows that compound 30 alleviates Aβ42 induced neurotoxicity in SH-SY5Y cells. Cells were pretreated with varying concentrations of compound 30 or 0.2% DMSO vehicle for 1 hour followed by 10 µM Aβ42 treatment and incubated for 72 hours. 10 µM TDZD-8 was used as a reference control.

To investigate whether semi-synthetic 6-C-glycosylflavone analogues exert neuroprotection against Aβ-induced neurotoxicity, compound 30 was assayed in an Alzheimer's disease cellular model where $A\beta_{42}$ oligomers were administrated to human SH-SY5Y neuroblastomas (Liang, et al. (2016) ACS Chem. Neurosci. 7:912-923; Agholme, et al. (2010) J. Alzheimer's Dis. 20:1069-82). Compound 30 displayed a good tolerability profile similar to 1, as a dose of 1000 μM exhibited no observable cytotoxicity. On the other hand, treatment with 10 μM $A\beta_{42}$ oligomers decreased cell viability to 40% compared with the controls (FIG. 10). However, such $A\beta_{42}$ neurotoxicity was prevented, as pretreatment of SH-SY5Y cells with compound 30 at concentrations from 1.25 to 20 μM for 1 hour followed by co-incubation with 10 μM $A\beta_{42}$ for 72 hours resulted in neuroprotection in a dose-dependent manner. The neuroprotective potency of 30 ($EC_{50}$, 8.7 μM) was a 5.4-fold increase in comparison to its parent compound 1 ($EC_{50}$, 47 μM).

Morphological observations also illustrated that pretreatment with compound 30 at 10 μM effectively protected the SH-SY5Y cells from $A\beta_{42}$ intoxication, as the neuronal cells were healthy and well differentiated with extended axons and dendrites. Although a similar neuroprotective activity was observed for isoorientin 1, compound 30 exhibited approximately a 20-fold improvement in effectiveness compared to the parent compound (effective dose: 30 at 10 μM versus 1 at 200 μM). Compound 30 and the other 6-C-glycosylflavone analogues exerted anti-Aβ neurotoxicity through protecting neurite outgrowth and neuronal differentiation, whose functions are constitutively regulated by GSK-3β and tau protein within axonal microtubules (Iqbal, et al. (2016) Nat. Rev. Neurol. 12:15-27).

Evaluations of 1, 4, 9, 17, 21, and 30 on Passive Membrane Permeability.

Oral administration is noninvasive and is preferred for chronical diseases such as Alzheimer's disease and other CNS disorders. The parallel artificial membrane permeability assay (PAMPA) is used to assess passive and transcellular permeability, which is well correlated with in vivo oral absorption rates for drugs that cross the gastrointestinal barrier (Chen, et al. (2008) Pharm. Res. 25:1511-20). In the PAMPA model, the amount of target compounds diffused from a donor compartment to an acceptor compartment through a tri-layer phospholipid pre-coated membrane are measured to assess oral-absorption potential of drug candidates. In the present study, 1, 4, 9, 17, 21 and 30 were evaluated with the PAMPA assay. Theophylline and atenolol, known for their low permeability, were used as negative controls. Desipramine, known for its high permeability, was used as a positive control. The measured $P_e$ values were compared with data in the literature (Chen, et al. (2008) Pharm. Res. 25:1511-20).

Compared to isoorientin 1, compounds 9, 17, 21 and 30 demonstrated a significant increase in permeability during the 5-hour incubation period (Table 3). Methylation of phenolic hydroxyls and transformation of the primary hydroxyl to hydrophobic amides on the C-glycone of 1 increased the PAMPA permeability ($P_e$), i.e., a 2.6- to 4.4-fold increase in $P_e$ relative to 1. Such $P_e$ changes agreed well with the C Log P values (Table 3). The PAMPA permeability of 30 was likely attributed to the $CF_3$ group. Multiple hydroxyl groups in the C-glycone and flavone moieties make 1 poorly permeable. For comparison, luteolin (4), an aglycone flavone, had a medium PAMPA permeability similar to 9, 17, and 21, indicating the liability of the polar C-glycone of 1 with respect to passive diffusion.

TABLE 3

| | PAMPA Permeability | | | |
|---|---|---|---|---|
| Compound No. | $P_e$ ($\times 10^{-6}$ cm/s) [a] | R (%) [b] | Permeability classification [c] | ClogP |
| Isoorientin 1 | 0.51 ± 0.01 | 48 | low | 0.21 |
| Luteolin 4 | 1.42 ± 0.07 | 43 | medium | 2.31 |
| 9 | 1.55 ± 0.06 | 46 | high | 1.35 |
| 17 | 1.77 ± 0.07 | 20 | high | 2.55 |
| 21 | 1.35 ± 0.08 | 30 | medium | 2.34 |
| 30 | 2.23 ± 0.21 | 30 | high | 1.62 |
| Theophylline | 0.04 ± 0.01 | n/a | low | −0.03 |
| Atenolol [d] | 0.29 ± 0.09 | 40 | low | −0.11 |
| Desipramine [d] | 13.43 ± 0.91 | 96 | high | 4.47 |

[a] $P_e$ values were the mean of PAMPA measurements (n = 3-4) with ±SD.
[b] Percent recovery (R %) measures mass retention of compounds trapped inside the PAMPA membrane.
[c] PAMPA permeability classification: high ($P_e \geq 1.5 \times 10^{-6}$ cm/s), medium ($1.0 \times 10^{-6}$ cm/s $\leq P_e \leq 1.5 \times 10^{-6}$ cm/s), low ($P_e < 1.0 \times 10^{-6}$ cm/s).
[d] The measured $P_e$ values were comparable to published data (Chen, et al. (2008) Pharm. Res. 25: 1511-20).

Computational Modeling.

To elucidate the molecular mechanisms by which the new 6-C-glycosylflavones increase the binding affinity and selectivity to GSK-3β relative to 1, compounds 5-31 were docked into GSK-3β enzyme. The AutoDock Vina program was used in the present study because it has shown good accuracies for binding pose prediction and scoring function (Trott & Olson (2010) *J. Comput. Chem.* 31:455-461; Wang, et al. (2016) *Phys. Chem. Chem. Phys.* 18:12964-75; Forli, et al. (2016) *Nat. Protoc.* 11:905-19). This docking tool has been widely used in drug design and applied in many cases of GSK-3β inhibitor discovery.

Two X-ray crystallographic structures of GSK-3β (PDB codes 1PYX and 1H8F) were chosen to take into account for potential induced fit effects upon ligand binding. The GSK-3β in 1PYX contains two $Mg^{2+}$ ions and a ligand ANP, a non-hydrolyzed ATP derivative, at the ATP site. Upon binding of $Mg^{2+}$ ions and an ATP-mimic ligand, it is postulated that GSK-3β undergoes subtle conformational changes in both the ATP and substrate sites for an optimal kinase reaction, a phenomenon known as induced fit effects. The GSK-3β structure in 1PYX hence adopts a conformation that resembles the native enzyme ready for substrate recognition. Docking 5-31 into the substrate site of GSK-3β using 1PYX would give more reliable binding poses. On the other hand, the GSK-3β in 1H8F is by far the only available X-ray crystallographic structure containing the ligand HEPES in the substrate site. HEPES in 1H8F may cause induced fit changes of GSK-3β conformation, particularly for the substrate site. Given the new 6-C-glycosylflavones are substrate competitive, 1PYX and 1H8F were used in molecular docking. The docking method was validated by re-docking and cross-docking experiments using both ATP-competitive and substrate-competitive inhibitors.

The synthetic 6-C-glycosylflavones (5-31) and their parent 1 were thus docked into 1PYX and 1H8F. Docking scores of 1PYX show a better linear fit to the experimental $pIC_{50}$ values ($R^2=0.7844$) than that of 1H8F ($R^2=0.6999$), suggesting more accurate predictions of binding poses using 1PYX than 1H8F. The 1PYX docking dataset was therefore used in the remainder of the study to analyze the molecular interactions responsible for the improved potency and selectivity to GSK-3F3.

The docking results of 1PYX showed that the C-glycone moiety of 5-31 forms hydrogen bonds with GSK-3β residues Gln89, Asn95, Arg96 and Glu97 within the substrate pocket, which is similar to 1. Moreover, the newly introduced hydrophobic groups indeed exhibit a favorable ligand pose to the concave surface comprised of Phe67, Val87, Leu88 and Phe93 on GSK-3β. The most potent compounds 30 and 31 ($IC_{50}$, 0.59 and 2.3 μM, respectively) contain a $CF_3$ moiety, which may form orthogonal multipolar interactions for protein binding. To visualize such molecular interactions, flexible-residue docking was conducted to refine binding poses of 9, 30 and 31 in 1PYX. To prepare the GSK-3β structure, side chains of Ser66, Phe67, Leu88, Gln89, Asp90, Phe93, Asn95 and Lys183 within the substrate site were treated as being flexible. The docking results of 30 indicated formation of orthogonal multipolar interactions. The (S)—$CF_3$ in 30 showed a favorable geometry within typical F . . . C distances to Leu88 (backbone amide carbonyl carbon, 3.3 Å), Gln89 (backbone amide carbonyl carbon, 3.6 Å) and Asp90 (side chain carbonyl carbon, 3.3 and 3.8 Å). It also formed a polar interaction with the backbone NH of Asp90 (F . . . H distance, 2.6 Å). In contrast, the (R)—$CF_3$ group of 31 was absent from these interactions likely owing to the orientation and steric hindrance by switching $CH_3$ and $CF_3$ positions at the stereocenter. Therefore, only hydrophobic interactions with Phe67, Val87 and Leu88 of GSK-3β exist in 31 (improper configuration of $CF_3$ for orthogonal multipolar interactions) as well as 9 (lack of $CF_3$).

Interestingly, the docking results showed that the catechol B-ring of the flavone core in 9, 30 and 31 appeared to have a n-cation interaction with Lys183. The distance between the catechol B-ring center and —$NH_3^+$ cation of Lys183 was 4.1 Å at an angle of 71.5°. In conjunction, the side chain —$NH_3^+$ of Lys183 formed weak hydrogen bonds with two methoxy oxygen atoms of catechol B-ring (distances of 3.1 and 3.2 Å). The orthogonal multipolar and n-cation interactions potentially enhance the binding affinity to GSK-3β.

Isoform-Specificity of 30.

Isoform-specificity of compound 30 for GSK-3β over GSK-3α was assessed with comparative molecular modeling. Given a lack of X-ray crystallographic structures for GSK-3α, a homology model of GSK-3α was built with the SWISS-MODEL server. A full human GSK-3α amino acid sequence (UniProt code: P49840) was searched against protein databases in BLAST and HHblits and 4470 templates were found. A GSK-3β template (PDB code 1PYX) with a top ranking and an overall sequence identity of 82.97% was selected for homology modeling of GSK-3α. A sequence alignment between the two GSK-3 isoforms indicated that GSK-3α had extra amino acid portions flanking the N- and C-termini of GSK-33β. Within the matched sequence portion, most amino acid differences occurred in the N- and C-terminal regions. In contrast, both the ATP and substrate domains of GSK-3α/β isoforms were conserved, with identity as high as 92.37%. The superposition and comparison of GSK-3β structure (PDB code 1PYX) with the GSK-3α homology model implied that those subtle differences in amino acid residues in the kinase catalytic domain (both ATP and substrate pockets) may affect substrate recognition as well as ligand binding. Intriguingly, docking experiment using the GSK-3α homology model showed that compound 30 resides in a similar location of the substrate site in comparison to GSK-3β docking data. However, the resulting binding pose of 30 in GSK-3α favors neither a n-cation interaction of catechol B-ring nor the orthogonal multipolar interaction of the (S)—$CF_3$ group. It is possible that the isoform-specificity of 30 to GSK-3β may be in part due to the lack of these critical molecular interactions in GSK-3α. Instead, the (S)-trifluoroisopropyl group of compound 30 simply exerts hydrophobic affinity with the homologous residues Phe130, Val150, and Leu151 in the substrate site of GSK-3α.

Example 3: Additional Isoorientin Analogs and Related Compounds

Having demonstrated the activity of isoorientin and analogs 5-31, additional analogs having GSK-3β inhibitory activity are contemplated, including, but not limited to, compounds having the structure of Formula III and Formula IV:

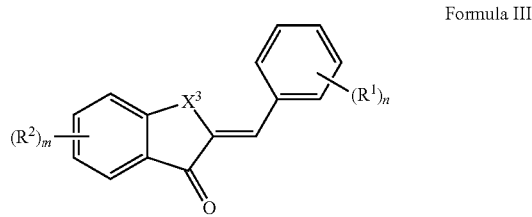

Formula III

-continued
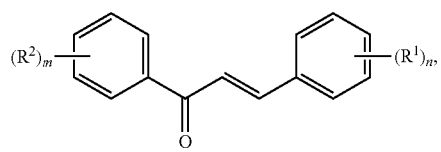
Formula IV
wherein n, m, R¹ and R² are as previously defined in Formula I and X³ is —O—, —NH—, —S— or —O—C—.
Exemplary compounds of Formula III include, but are not limited, compounds 32-35.
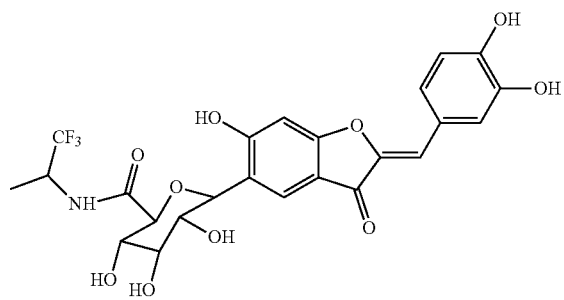
32
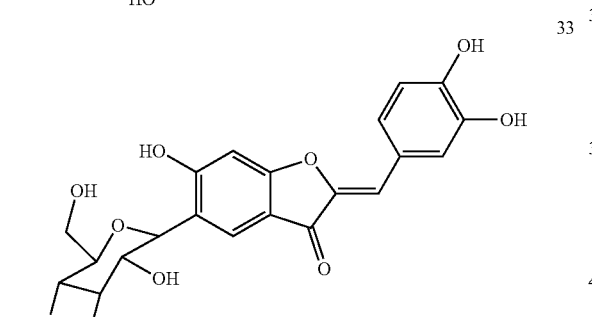
33
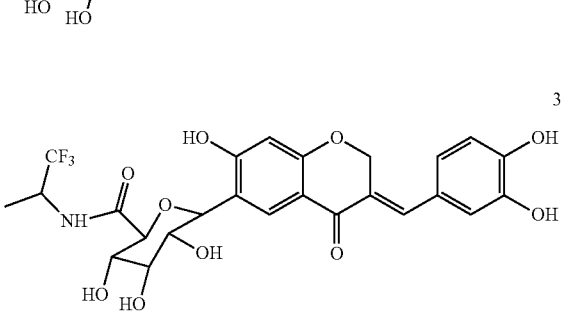
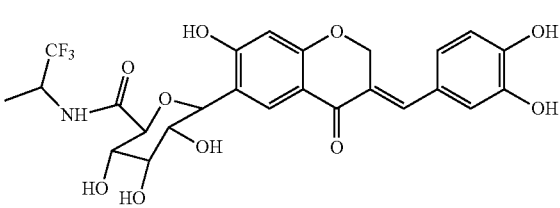
34
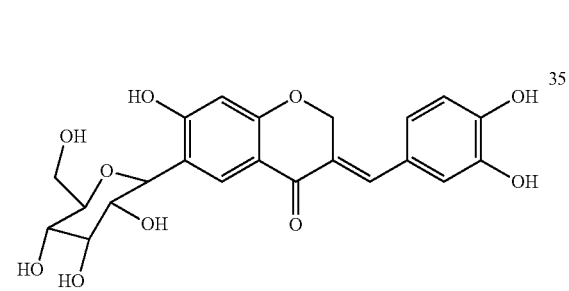
35
Exemplary compounds of Formula IV include, but are not limited to compounds 36-41:
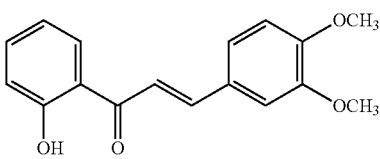
36
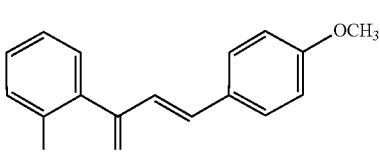
37
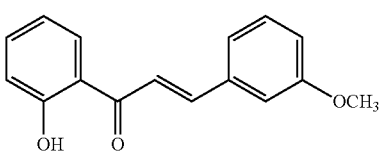
38
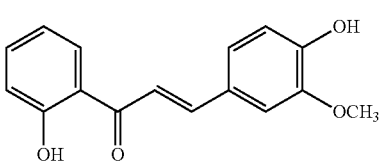
39
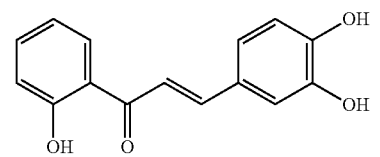
40
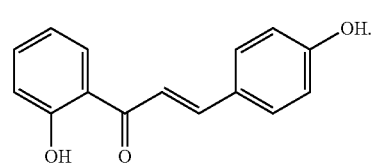
41
What is claimed is:
1. A compound of Formula II, or a pharmaceutically acceptable salt or solvate thereof:
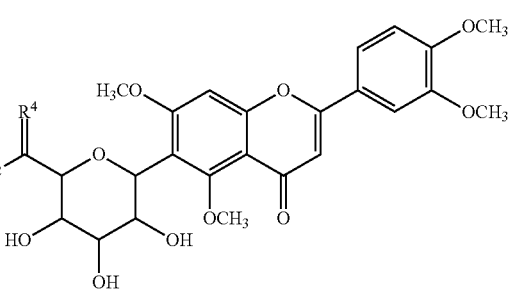
Formula II wherein R³ is a hydrogen, substituted or unsubstituted alkyl, substituted or unsubstituted alkoxyl, substituted or unsubstituted cycloalkyl, substituted or unsubstituted heterocyclyl, substituted or unsubstituted aryl, or substituted or unsubstituted heteroaryl group;

R⁴ is O; and

X² is O, CH₂ or NH.

2. The compound of claim 1, wherein R³ is a substituted or unsubstituted alkyl, substituted or unsubstituted alkoxyl, substituted or unsubstituted cycloalkyl, or substituted or unsubstituted heterocyclyl; R⁴ is O; and X² is NH.

3. A compound of Formula III, or a pharmaceutically acceptable salt or solvate thereof:

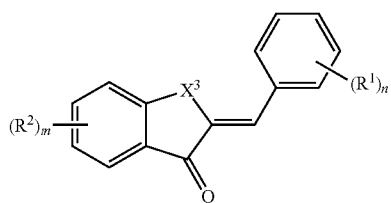

Formula III wherein n is 2;

m is 2;

each R¹ is independently a hydroxyl or alkoxyl group;

at least one R² is a substituted heterocyclyl group and each other R² is a hydroxyl group; and X³ is —O—, —NH—, —S— or —O—C—.

4. The compound of claim 3, wherein said compound has the structure of Formula IIIa:

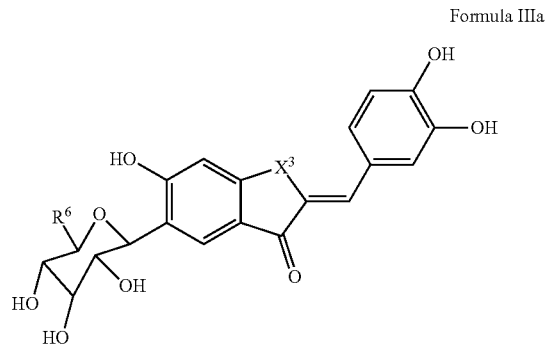

Formula IIIa wherein

X³ is —O—, —NH—, —S— or —O—C—; and R⁶ is a substituted alkyl group.

5. A pharmaceutical composition comprising a compound of claim 1 or 3 and at least one pharmaceutically acceptable carrier, adjuvant, or vehicle.

6. A method for treating a cognitive, neurodegenerative or neurological disease or condition comprising administering to a subject in need of treatment a therapeutically effective amount of a pharmaceutical composition of claim 5 thereby treating the subject's cognitive, neurodegenerative or neurological disease or condition.

7. The method of claim 6, wherein the cognitive, neurodegenerative or neurological disease or condition is Alzheimer's disease.

8. A method for treating cancer, obesity, diabetes, an inflammatory or autoimmune disease, cardiovascular disorder, metabolic syndrome X, hair loss, severe acute respiratory syndrome coronavirus, cocaine addiction, dental caries, bone loss or glaucoma comprising administering to a subject in need of treatment a therapeutically effective amount of a pharmaceutical composition of claim 5 thereby treating the subject's diabetes, inflammatory or autoimmune disease, cardiovascular disorder, metabolic syndrome X, hair loss, severe acute respiratory syndrome coronavirus, cocaine addiction, dental caries, bone loss or glaucoma.

* * * * *